(12) United States Patent
Izuhara et al.

(10) Patent No.: US 9,126,908 B2
(45) Date of Patent: Sep. 8, 2015

(54) AROMATIC SULFONIC ACID DERIVATIVE, SULFONIC ACID GROUP-CONTAINING POLYMER, BLOCK COPOLYMER, POLYMER ELECTROLYTE MATERIAL, POLYMER ELECTROLYTE FORM ARTICLE, AND POLYMER ELECTROLYTE FUEL CELL

(75) Inventors: Daisuke Izuhara, Otsu (JP); Hiroaki Umeda, Otsu (JP); Emi Amano, Otsu (JP); Tomoyuki Kunita, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/130,300

(22) PCT Filed: Jun. 27, 2012

(86) PCT No.: PCT/JP2012/066415
§ 371 (c)(1),
(2), (4) Date: Apr. 4, 2014

(87) PCT Pub. No.: WO2013/002274
PCT Pub. Date: Jan. 3, 2013

(65) Prior Publication Data
US 2014/0213671 A1   Jul. 31, 2014

(30) Foreign Application Priority Data

Jun. 28, 2011 (JP) .................. 2011-142613
Sep. 13, 2011 (JP) .................. 2011-199327

(51) Int. Cl.
| C08G 75/24 | (2006.01) |
| C08G 65/40 | (2006.01) |
| C07C 317/22 | (2006.01) |
| H01B 1/12 | (2006.01) |
| C07C 309/60 | (2006.01) |
| H01B 1/06 | (2006.01) |
| H01M 4/86 | (2006.01) |
| H01M 8/02 | (2006.01) |
| H01M 8/10 | (2006.01) |

(52) U.S. Cl.
CPC ............. *C07C 317/22* (2013.01); *C07C 309/60* (2013.01); *C08G 65/40* (2013.01); *H01B 1/122* (2013.01); *H01M 8/1025* (2013.01); *H01M 8/1027* (2013.01); *H01M 8/1032* (2013.01); *H01M 8/1039* (2013.01); *H01M 2008/1095* (2013.01)

(58) Field of Classification Search
CPC ....................................... C08G 75/24
USPC .................................. 528/391, 373
See application file for complete search history.

(56) References Cited

PUBLICATIONS

Yoo, D.J. et al "Synthesis, and structural—electrolytes", Bulletin of the Korean chemicla society; 2011, vol. 32, No. 11, pp. 4041-4048.*
Dong-Jin-Yu; KR-10-2012-0060965, "Sulfonated—their manufacturing methods", Jun. 2012.*
Sakaguchi et al; "Sulfonated acid group—fuel cells", 2008; Toyobo Co. Ltd., Japan; 2008; Chem Abstract 148:541955.*

* cited by examiner

*Primary Examiner* — Duc Truong
(74) *Attorney, Agent, or Firm* — Pillsbury Winthrop Shaw Pittman LLP

(57) ABSTRACT

Provided are an aromatic sulfonic acid derivative and a sulfonic acid group-containing polymer, each of which has excellent proton conductivity even under low humidification conditions, while having excellent mechanical strength and chemical stability, and enables a solid polymer fuel cell to achieve high output and excellent physical durability when used therein. This aromatic sulfonic acid derivative has a specific structure and is characterized in that a sulfonic acid group is introduced into more than 50% of all the phenyl groups. This sulfonic acid group-containing polymer is characterized by being obtained by polymerization using the aromatic sulfonic acid derivative, and is also characterized by having a specific structure.

7 Claims, No Drawings

AROMATIC SULFONIC ACID DERIVATIVE, SULFONIC ACID GROUP-CONTAINING POLYMER, BLOCK COPOLYMER, POLYMER ELECTROLYTE MATERIAL, POLYMER ELECTROLYTE FORM ARTICLE, AND POLYMER ELECTROLYTE FUEL CELL

CROSS-REFERENCE TO RELATED APPLICATIONS

The present application is the U.S. National Stage application to International Patent Application No. PCT/JP2012/066415, filed Jun. 27, 2012, which claims priority to Japanese Patent Application Nos. 2011-142613, filed Jun. 28, 2011 and 2011-199327, filed Sep. 13, 2011, which are being incorporated by reference herein in their entireties.

TECHNICAL FIELD

The present invention relates to aromatic sulfonic acid derivatives, sulfonic acid group-containing polymers, block copolymers, polymer electrolyte materials, polymer electrolyte form article, and polymer electrolyte fuel cells

BACKGROUND ART

The fuel cell is a power generation device that derives electric energy by electrochemically oxidizing fuel such as hydrogen and methanol, and in recent years, it has attracted attention as a clean energy source. Among others, the polymer electrolyte fuel cell, which normally works at a low operating temperature around 100° C. and has a high energy density, is expected to serve in a wide variety of fields as relatively small distributed power generation facilities and power generation equipment for movable bodies such as automobiles and ships. Furthermore, it has attracted attention as power source for small movable devices and portable appliances, and in particular it is expected to replace secondary batteries such as nickel hydrogen batteries and lithium ion batteries incorporated in portable telephones and personal computers.

A fuel cell commonly includes cells as units, each composed mainly of a membrane electrode assembly (hereinafter occasionally abbreviated as MEA) sandwiched between separators. A MEA consists mainly of electrodes, i.e., an anode and a cathode where the power generating reaction takes place, and a polymer electrolyte membrane that works to conduct protons between the anode and the cathode. A polymer electrolyte membrane is formed primarily of a polymer electrolyte material. Polymer electrolyte materials have been used also as, for example, binders for electrode catalyst layers. Polymer electrolyte membranes are required primarily to have high proton conductivity, and in particular, they must have high proton conductivity even under high temperature, low humidify conditions. Furthermore, polymer electrolyte membranes are required to be low in permeability to fuels so as to function as a barrier to prevent direct reaction between fuels and oxygen. Other required characteristics include chemical stability for resisting an oxidizing atmosphere during fuel cell operation, as well as mechanical strength and physical durability for resisting thin film formation and repeated swelling-drying cycles.

Conventionally, Nafion (registered trademark) (manufactured by DuPont), which is a perfluorosulfonic acid based polymer, has been used as material for polymer electrolyte membrane. Being manufactured through a multi-stage synthesis process, Nafion (registered trademark) is very high in price and it also has the problem of large fuel crossover (fuel permeability). It has been also pointed out that the product has other problems such as a decrease in film's mechanical strength and physical durability caused by swelling-drying cycles, inability to work at high temperatures due to low softening point, necessity of disposal treatments after use, and difficulty in recycling of materials.

Under such circumstances, active studies have been carried out in recent years to develop hydrocarbon based electrolyte membranes as polymer electrolyte materials that are so low in price and good in film characteristics as to replace Nafion (registered trademark).

For instance, some studies have proposed the use of a block copolymer composed mainly of hydrophobic segments virtually free of sulfonic acid groups and hydrophilic segments containing sulfonic acid group in which the hydrophobic segments include polyethersulfone (PES) or polyether ketone while the hydrophilic segments include sulfonated polyethersulfone or sulfonated polyether ketone (patent documents 1 and 2).

Patent document 3 describes an attempt of block copolymerization incorporating a small amount of 4,4'-dihydroxy benzophenone which contains two sulfonic acid groups. Non-patent document 1 describes the use of a block copolymer composed mainly of polyethersulfone (PES) as hydrophobic segment and sulfonated polyethersulfone in which phenyl groups contain a sulfonic acid group as hydrophilic segment.

PRIOR ART DOCUMENTS

Patent Documents

Patent document 1: Japanese Unexamined Patent Publication (Kokai) No. 2009-235158
Patent document 2: International Publication WO 08/018,487
Patent document 3: Japanese Unexamined Patent Publication (Kokai) No. 2011-132388

Non-Patent Documents

Non-patent document 1: Journal of Polymer Science A Polymer Chemistry, 48, 2757, 2010.

SUMMARY OF THE INVENTION

Problems to be Solved by the Invention

The block copolymers used as hydrophilic segment in patent documents 1 and 2 are alternating copolymers composed of constituent units in which 50% of the phenyl groups contains a sulfonic acid group, namely, an aromatic dihalide in which two sulfonic acid groups are introduced for every two phenyl groups, and a bisphenol in which sulfonic acid groups are not introduced for any pair of phenyl groups. Commonly, these PES's and polyether ketones are synthesized through an aromatic nucleophilic substitution reaction of an electron-withdrawing aromatic dihalide and an electron-releasing bisphenol, and therefore, an electron-withdrawing sulfonic acid group can be introduced only into the aromatic dihalide from the viewpoint of polymerization reaction activity, making it difficult to introduce sulfonic acid groups into more than 50% of the total phenyl groups. Accordingly, there have been limitations on the conventional techniques in further increasing the local density of sulfonic acid groups in the hydrophilic domains and improving the proton conductivity under low humidify conditions.

For the bisphenol compound proposed in patent document 3, furthermore, the present inventors have found that the existence of an electron-withdrawing ketone group and two sulfonic acid groups works to decrease the nucleophilicity so largely that the compound remains completely unreacted with a dihalide compound.

For the block copolymer proposed in non-patent document 1, the present inventors have also found that a polymer similar to the one described in patent document 1 is prepared first and a sulfonic acid group is then introduced into a phenyl group with a high electronic density located adjacent to an ether group, easily leading to desulfonation through the reverse reaction. In addition to insufficient chemical stability, another problem is the necessity of post-sulfonation reaction and reprecipitation for refinement, leading to an increased number of production steps and, in turn, increased prices.

Thus, polymer electrolyte materials manufactured by conventional techniques cannot work sufficiently for improving economic efficiency, processability, proton conductivity, mechanical strength, chemical stability, and physical durability and therefore cannot serve as useful polymer electrolyte materials for industrial applications.

In view of such a background associated with the conventional techniques, the present invention aims to provide a sulfonic acid group-containing polymer, a block copolymer, and an aromatic sulfonic acid derivative that are useful to produce a polymer electrolyte material that has high proton conductivity under low humidify conditions, shows high mechanical strength and chemical stability, and furthermore, serves to produce polymer electrolyte fuel cells with high output and excellent physical durability.

Means of Solving the Problems

The present invention adopts the following measures to solve these problems. Specifically, the aromatic sulfonic acid derivatives according to the present invention are aromatic sulfonic acid derivatives as represented by the general formula (M1) given below in which sulfonic acid groups are contained in more than 50% of all phenyl groups.

[Chemical formula 1]

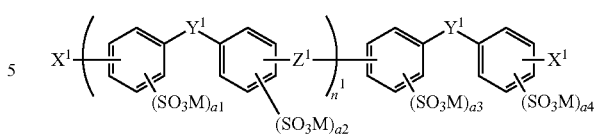
(M1)

(In the general formula (M1), $n^1$ is an integer of 1 or greater and $a_1$ to $a_4$ are each an integer of 0 or greater. M's are independently a hydrogen, a metal cation, ammonium cation, or a hydrocarbon group with a carbon number of 1 to 20 and $X^1$'s are independently a halogen atom. Furthermore, $Y^1$ is an electron-withdrawing group and $Z^1$ is an electron-withdrawing group, —O—, —S—, or direct bonding.)

The sulfonic acid group-containing polymers according to the present invention are characterized by being produced by polymerization involving the aromatic sulfonic acid derivative as described above and also characterized by containing a constituent unit as represented by either the general formula (P1) or (P2) given below with a content of 20 wt % or more.

[Chemical formula 2]

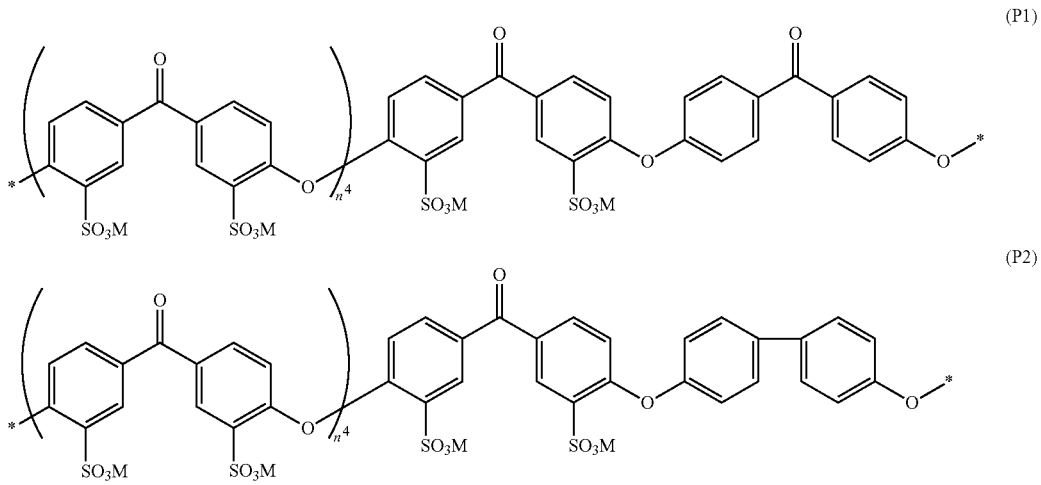

(In the general formulae (P1) and (P2), $n^4$ is an integer of 1 to 3, and M's are independently a hydrogen, a metal cation, an ammonium cation, or a hydrocarbon group with a carbon number of 1 to 20. Here, * indicates bonding sites to constituent units as represented by either the general formula (P1) or (P2) or to other constituent units.)

The block copolymers according to the present invention are block copolymers including one or more ionic group-containing segments (A1) and one or more ionic group-free segments (A2), wherein the ionic group-containing segments (A1) include a constituent unit as represented by the general formula (S1) given below.

[Chemical formula 3]

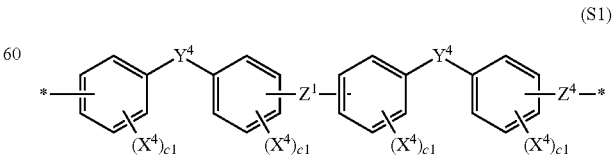
(S1)

(In the general formula (S1), independently, $X^4$ is an ionic group; $c_1$ is an integer of 1 or greater; $Y^4$ is an electron-withdrawing group; $Z^4$ is an electron-withdrawing group, —O—, —S—, or direct bonding. $X^4$, $c_1$, $Y^4$, and $Z^4$ may represent two or more different groups or numbers. Here, * indicates bonding sites to constituent units as represented by the general formula (S1) or to other constituent units.)

Furthermore, the polymer electrolyte materials, polymer electrolyte form article, and polymer electrolyte fuel cells according to the present invention are characterized by produced from sulfonic acid group-containing polymers and block copolymers as described above.

Effect of the Invention

A sulfonic acid group-containing polymer and block copolymer polymerized from an aromatic sulfonic acid derivative according to the present invention and a polymer electrolyte material produced from the sulfonic acid group-containing polymer and block copolymer according to the present invention can have high proton conductivity under low humidify conditions, show high mechanical strength and chemical stability, and furthermore, serve to produce polymer electrolyte fuel cells with high output and excellent physical durability, and they also can provide polymer electrolyte form article and polymer electrolyte fuel cells formed thereof.

DESCRIPTION OF EMBODIMENTS

The invention is described in more detail below.

As a result of intensive studies aiming to solve the above problems, the present inventors successfully invented aromatic sulfonic acid derivatives in which electron-withdrawing groups work to chemically stabilize all arylene groups while locally increasing the density of sulfonic acid groups, as well as sulfonic acid group-containing polymers polymerized therefrom and sulfonic acid group-containing polymers having a specific structure. They found that these sulfonic acid group-containing polymers can serve as polymer electrolyte materials, particularly as electrolyte membranes for fuel cells, that exhibits excellent performance in terms of high proton conductivity and power generation characteristics under low-humidify or other various conditions, processability, such as for film production, chemical stability properties such as oxidation resistance, radical resistance, and hydrolysis resistance, and physical durability properties such as film's mechanical strength and hot water resistance, making it possible to solve all the above problems, and then they arrived at the present invention after various additional studies.

Specifically, the aromatic sulfonic acid derivatives according to the present invention are aromatic sulfonic acid derivatives as represented by the general formula (M1) given below in which sulfonic acid groups are contained in more than 50% of all phenyl groups.

[Chemical formula 4]

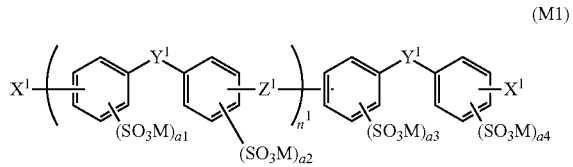

(M1)

(In the general formula (M1), $n^1$ is an integer of 1 or greater and $a_1$ to $a_4$ are each an integer of 0 or greater. M's are independently a hydrogen, metal cation, ammonium cation, or hydrocarbon group with a carbon number of 1 to 20 and $X^1$'s are independently a halogen atom. Furthermore, $Y^1$ is an electron-withdrawing group and $Z^1$ is an electron-withdrawing group, —O—, —S—, or direct bonding.)

Here, specific examples of $X^1$ include fluorine, chlorine, bromine, and iodine, of which fluorine and chlorine are more preferable in terms of reactivity and fluorine is the most preferable. Specific examples of the electron-withdrawing group $Y^1$ include —CO—, —CONH—, —(CF$_2$)$_n$— (n is an integer from 1 to 10), —C(CF$_3$)$_2$—, —COO—, —SO$_2$—, —SO—, and —PO(R$^1$)— (R$^1$ is an arbitrarily selected organic group). In particular, —CO— and —SO$_2$— are more preferable in terms of chemical stability and cost, and —CO— is the most preferable in terms of physical durability.

Specific examples of $Z^1$ include —CO—, —CONH—, —(CF$_2$)$_n$— (n is an integer from 1 to 10), —C(CF$_3$)$_2$—, —COO—, —SO$_2$—, —SO—, —PO(R$^1$)— (R$^1$ is an arbitrarily selected organic group), and other electron-withdrawing groups, as well as —O—, —S—, and direct bonding, of which —O—, —S—, and direct bonding are more preferable and —O— is the most preferable in terms of cost and physical durability. Furthermore, $n^1$ is more preferably an integer from 1 to 10, still more preferably from 1 to 3, and most preferably 1 or 2, in terms of easiness of synthesis.

The aromatic sulfonic acid derivatives according to the present invention are high in chemical stability due to the effect of the electron-withdrawing group $Y^1$ and can form a sulfonic acid group-containing polymer with a locally increased density of sulfonic acid groups, leading to high proton conductivity even under low humidify conditions.

Various characteristics of a sulfonic acid group-containing polymer, including processability, domain size, crystalline/amorphism, mechanical strength, proton conductivity, and dimensional stability can be controlled by adopting an aromatic sulfonic acid derivative according to the present invention having appropriate properties including chemical structure, $n^1$, content of sulfonic acid groups.

The proportion of the phenyl groups containing a sulfonic acid group to all phenyl groups, that is the proportion of the phenyl groups containing the —SO$_3$M group in the formula (M1), should be as high as possible from the viewpoint of the proton conductivity under low humidify conditions. Specifically, it is required to be more than 50%, and it is preferably 60% or more, more preferably 75% or more, particularly preferably 90% or more, and most preferably 100%.

The aromatic sulfonic acid derivatives according to the present invention preferably have a structure as represented by the general formula (M2) given below from the viewpoint of the easiness of synthesis and physical durability. They are more preferably aromatic sulfonic acid derivatives as represented by the general formula (M3) given below.

[Chemical formula 5]

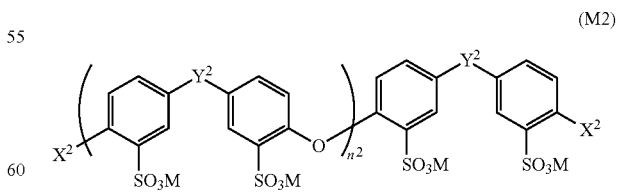

(M2)

(In the general formula (M2), $n^2$ is an integer of 1 or greater, and M's are independently a hydrogen, a metal cation, an ammonium cation, or a hydrocarbon group with a carbon number of 1 to 20. $X^2$'s are independently F or Cl, and $Y^2$ is —CO— or —SO$_2$—.

[Chemical formula 6]

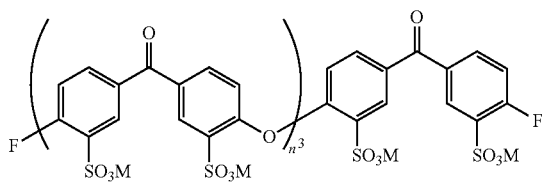

(M3)

(In the general formula (M3), $n^3$ is an integer from 1 to 3, and M's are independently a hydrogen, a metal cation, an ammonium cation, or a hydrocarbon group with a carbon number of 1 to 20.

Described below are the sulfonic acid group-containing polymers according to the present invention.

The sulfonic acid group-containing polymers according to the present invention are characterized by being polymerized from an aromatic sulfonic acid derivative as represented by the general formula (M1) given above. Or, they may be characterized by having a specific structure, as found by the present inventors from results of polymerization from an aromatic sulfonic acid derivative as represented by the general formula (M1) given above.

Their specific examples include aromatic polymers such as sulfonic acid group-containing aromatic polyether ketones, sulfonic acid group-containing aromatic polyethersulfones, sulfonic acid group-containing aromatic polyether phosphine oxides, sulfonic acid group-containing aromatic polysulfide ketones, sulfonic acid group-containing aromatic polysulfide sulfones, sulfonic acid group-containing aromatic polysulfide phosphine oxides, and sulfonic acid group-containing polyarylenes.

Of these, from the viewpoint of cost, sulfonic acid group-containing aromatic polyether ketones, sulfonic acid group-containing aromatic polyethersulfones, sulfonic acid group-containing aromatic polyether phosphine oxides, and sulfonic acid group-containing polyarylenes are preferable, of which sulfonic acid group-containing aromatic polyether ketones and sulfonic acid group-containing aromatic polyethersulfones are more preferable, of which sulfonic acid group-containing aromatic polyether ketones are the most preferable.

These sulfonic acid group-containing aromatic polyethers can be synthesized through an aromatic nucleophilic substitution reaction involving an aromatic sulfonic acid derivative (dihalide compound) as represented by the general formula (M1) and an arbitrarily selected divalent phenol compound. There are no specific limitations on the divalent phenol compound, and an appropriate one may be selected taking its chemical stability, physical durability, cost, etc. into consideration. Here, such a divalent phenol compound containing a sulfonic acid group may be used as a monomer unless it has adverse influence on the advantageous effect of the invention, but it is preferable to use one that contains no sulfonic acid group from the viewpoint of reactivity.

Preferred examples of the divalent phenol compounds that can be used for the present invention include those divalent phenol compounds as represented by any of the general formulae (Y-1) to (Y-30) given below. Here, preferred examples also include divalent thiol compounds in the form of heteroatom derivatives of these divalent phenol compounds. In particular, from the viewpoint of high electronic density and high polymerization reactivity, divalent phenol compounds as represented by any of the general formulae (Y-1) to (Y-5) are more preferable, and divalent phenol compounds as represented by any of (Y-1) to (Y-3) are still more preferable.

Divalent phenol compounds having an electron-withdrawing group and high chemical stability include those as represented by any of the formulae (Y-10) to (Y-11) and (Y-13) to (Y-15) given below. Of these, divalent phenol compounds as represented by (Y-10), (Y-14), or (Y-15) are preferable from the viewpoint of crystallizability and dimensional stability.

Of the divalent phenol compounds as represented by any of the general formulae (Y-1) to (Y-30) given below, those divalent phenol compounds as represented by any of the general formulae (Y-1) and (Y-14) given below are the most preferable from the viewpoint of chemical stability and physical stability.

[Chemical formula 7]

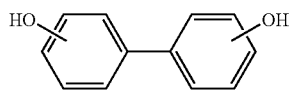

(Y-1)

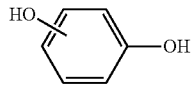

(Y-2)

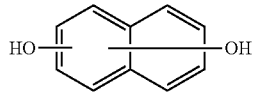

(Y-3)

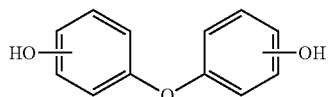

(Y-4)

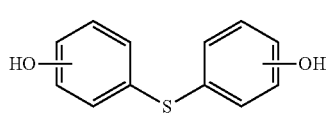

(Y-5)

(The divalent phenol compounds as represented by any of the general formulae (Y-1) to (Y-5) may be substituted appropriately, but do not contain a sulfonic acid group.)

[Chemical formula 8]

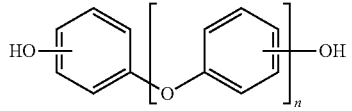

(Y-6)

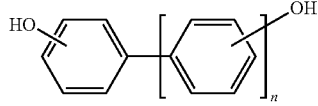

(Y-7)

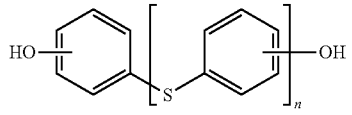

(Y-8)

(Y-9)

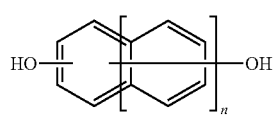

(The divalent phenol compounds as represented by any of the general formulae (Y-6) to (Y-9) may be substituted appropriately. Here, n is an integer of 1 or greater.)

[Chemical formula 9]

(Y-10)

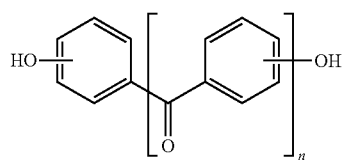

(Y-11)

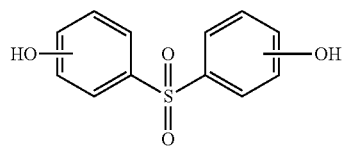

(Y-12)

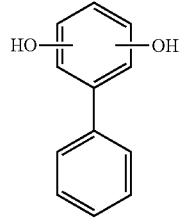

(Y-13)

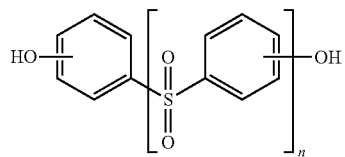

(Y-14)

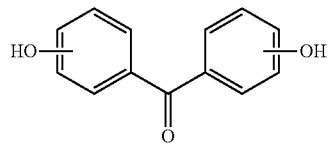

(Y-15)

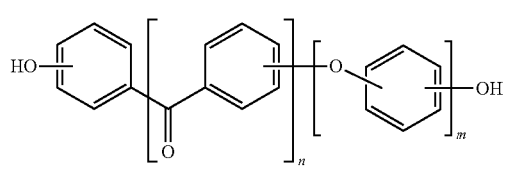

(Y-16)

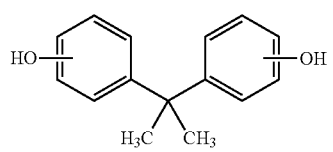

(Y-17)

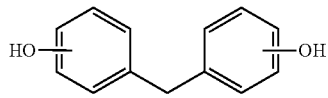

(Y-18)

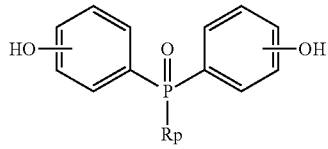

(Y-19)

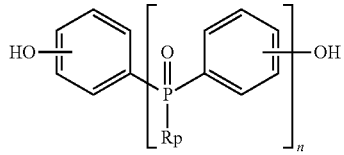

(The divalent phenol compounds as represented by any of the general formulae (Y-10) to (Y-19) may be substituted appropriately. Here, n and m are each an integer of 1 or greater, and Rp is an arbitrarily selected organic group.)

[Chemical formula 10]

(Y-20)

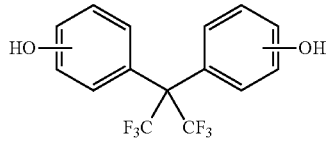

(Y-21)

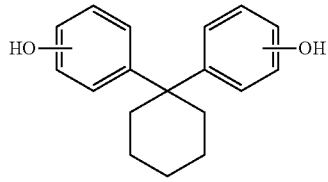

(Y-22)

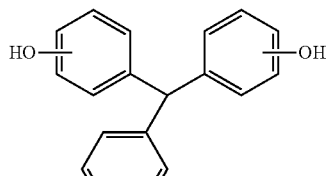

(Y-23)

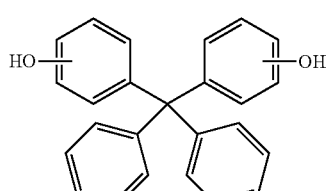

(Y-24)

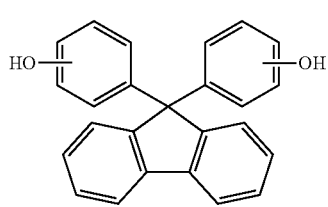

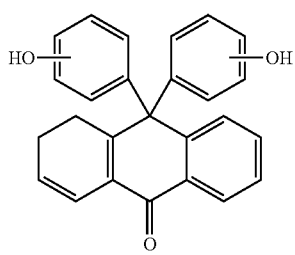

(Y-25)

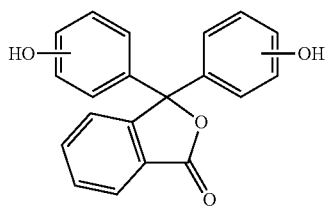

(Y-26)

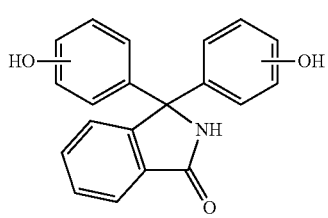

(Y-27)

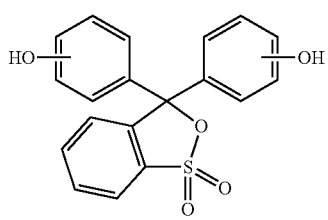

(Y-28)

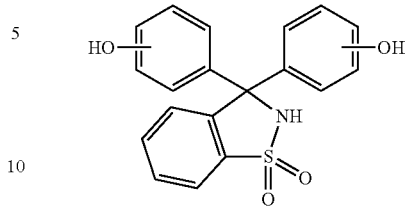

(Y-29)

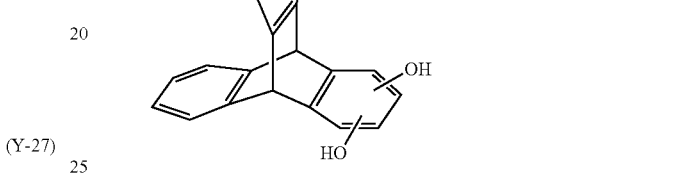

(Y-30)

(The divalent phenol compounds as represented by any of the general formulae (Y-20) to (Y-30) may be substituted appropriately.)

For example, a constituent unit produced through an aromatic nucleophilic substitution reaction of an aromatic sulfonic acid derivative (dihalide compound) as represented by the general formula (M1) and a divalent phenol compound as represented by the general formula (Y-1) or (Y-14) has a structure as represented by the general formula (P1) or (P2) given below, and it is a particularly preferable constituent unit for the sulfonic acid group-containing polymers according to the present invention.

[Chemical formula 11]

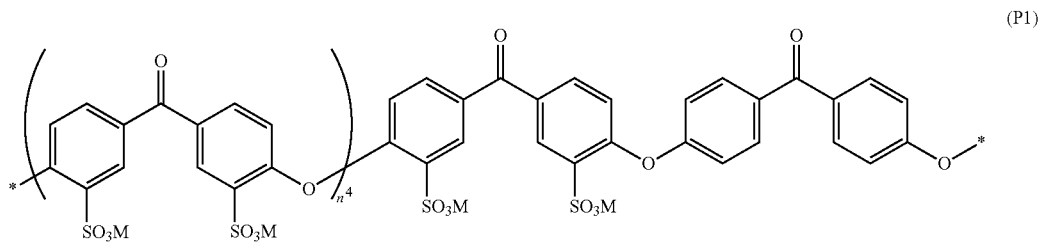

(P1)

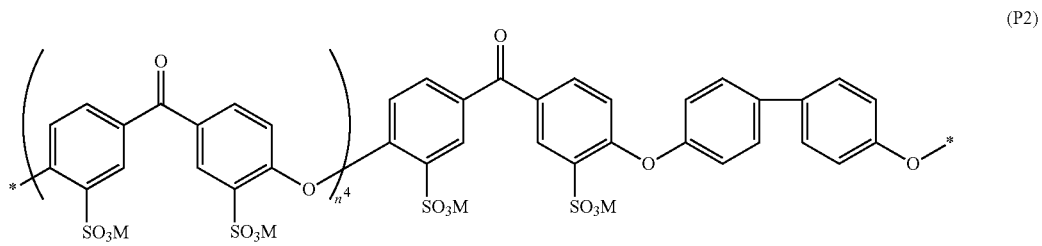

(P2)

(in the general formulae (P1) and (P2), $n^4$ is an integer of 1 to 3, and M's are independently a hydrogen, a metal cation, an ammonium cation, or a hydrocarbon group with a carbon number of 1 to 20.)

In the formula, $n^4$ is more preferably an integer of 1 or 2, most preferably an integer of 1, from the viewpoint of the easiness of synthesis.

Preferable examples of the sulfonic acid group-containing polymers according to the present invention include sulfonic acid group-containing polymers in which constituent units as represented by the general formula (P1) or (P2) account for 20 wt % or more. If the constituent units as represented by the general formula (P1) or (P2) account for only less than 20 wt %, it is not preferable because in that case, the proton conductivity under low humidify conditions will not be high enough to achieve the advantageous effect of the invention. For the present invention, a constituent unit as represented by the general formula (P1) or (P2) may be used simultaneously.

For the present invention, it is also preferable to prepare a sulfonic acid group-containing polymer as represented by the general formula (P1) by introducing a protective group into a divalent phenol compound and performing a deprotection method after polymerization or molding to achieve its conversion into a structure as represented by the general formula (P1). From the viewpoint of reactivity and chemical stability, preferred examples of such divalent phenol compounds containing a protective group include compounds as represented by any of the general formulae (r1) to (r10) given below and derivatives of these divalent phenol compounds.

[Chemical formula 12]

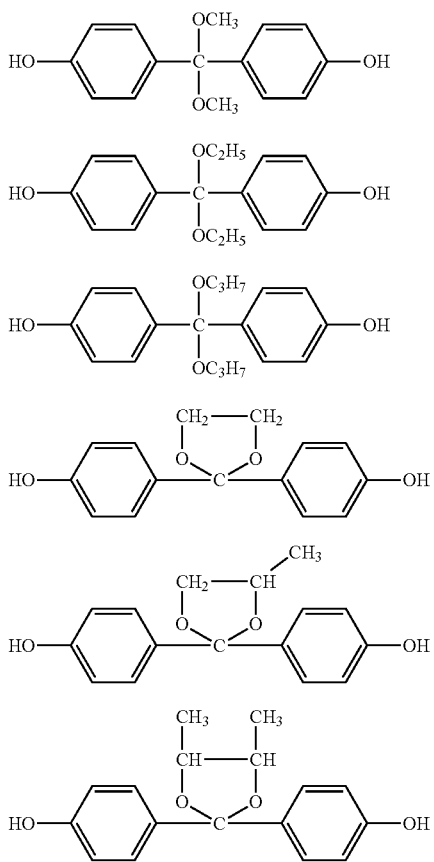

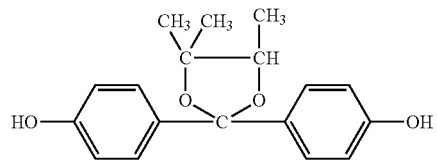

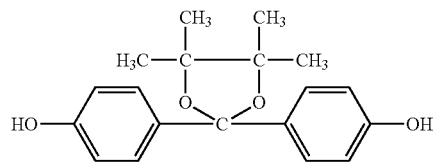

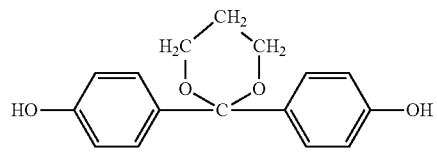

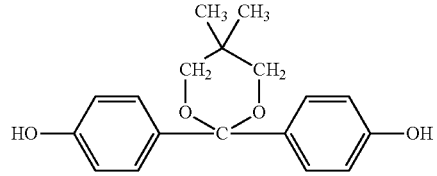

Of these divalent phenol compounds, those compounds as represented by any of the general formulae (r4) to (r10) are more preferable; those as represented by any of the general formula (r4), (r5), and (r9) are still more preferable; and those as represented by any of the general formula (r4) are the most preferable.

Another embodiment of the present invention is block copolymers having a specific preferable structure. Described below are these block copolymers.

As a result of intensive studies aiming to solve the above problems, the present inventors successfully invented block copolymers in which a proton conduction channel can be formed, by adding electron-withdrawing groups to decrease the electronic density in all benzene rings so that they are chemically stabilized to prevent the elimination reaction of sulfonic acid groups and the electrophilic reaction of hydroxyradicals and also by locally increasing the density of sulfonic acid groups. They found that these block copolymers can serve as polymer electrolyte material, particularly as electrolyte membrane for fuel cells, that exhibits excellent performance in terms of high proton conductivity and power generation characteristics under low-humidify or other various conditions, processability such as for film production, chemical stability properties such as oxidation resistance, radical resistance, and hydrolysis resistance, and physical durability properties such as film's mechanical strength and hot water resistance, making it possible to solve all the above problems, and then they arrived at the present invention after various additional studies.

Specifically, the block copolymers according to the present invention are block copolymers including one or more ionic group-containing segments (A1) and one or more ionic group-free segments (A2), wherein the ionic group-containing segments (A1) include a constituent unit as represented by the general formula (S1) given below.

[Chemical formula 13]

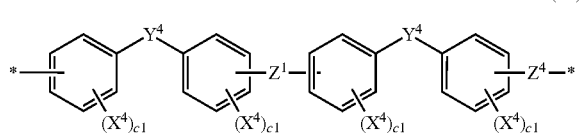

(S1)

(In the general formula (S1), independently, $X^4$ is an ionic group; $c_1$ is a an integer of 1 or greater; $Y^4$ is and electron-withdrawing group; $Z^4$ is an electron-withdrawing group, —O—, —S—, or direct bonding. $X^4$, $c_1$, $Y^4$, and $Z^4$ may represent two or more different groups or numbers. Here, * indicates bonding sites to constituent units as represented by the general formula (S1) or to other constituent units.)

Specific examples of the electron-withdrawing group $Y^4$ include —CO—, —CONH—, —(CF$_2$)$_n$— (n is an integer from 1 to 10), —C(CF$_3$)$_2$—, —COO—, —SO$_2$—, —SO—, and —PO(R$^1$)— (R$^1$ is an arbitrarily selected organic group). In particular, —CO— and —SO$_2$— are more preferable in terms of chemical stability and cost, and —CO— is the most preferable in terms of physical durability.

Specific examples of $Z^4$ include —CO—, —CONH—, —(CF$_2$)$_n$— (n is an integer from 1 to 10), —C(CF$_3$)$_2$—, —COO—, —SO$_2$—, —SO—, —PO(R$^1$)— (R$^1$ is an arbitrarily selected organic group), and other electron-withdrawing groups, as well as —O—, —S—, and direct bonding, of which —O— and —S— are more preferable, of which —O— is the most preferable, in terms of cost and physical durability. Here, $c_1$ is an integer of 1 or greater, more preferably 1 or 2, and most preferably 1, from the viewpoint of production cost.

The constituent units represented by the general formula (S1) are high in chemical stability due to the effect of the electron-withdrawing group $Y^4$ and can form a block copolymer with a locally increased density of sulfonic acid groups, so that a proton conduction channel is formed, leading to high proton conductivity even under low humidify conditions.

In the ionic group-containing segments, the content of the constituent units represented by the general formula (S1) is preferably as high as possible from the viewpoint of the proton conductivity under low humidify conditions. It is preferably more than 50 mol %, more preferably 60 mol % or more, particularly preferably 65 mol % or more, and most preferably 75 mol % or more. For the present invention, a constituent unit is defined as one including four benzene rings connected in the backbone chain direction as represented by the general formula (S1).

For the present invention, a segment is a partial structure of a block copolymer, includes of one type of repeating units or combinations of a plurality of types of repeating units, and has a molecular weight of 2,000 or more. A block copolymer according to the present invention includes both an ionic group-containing segment (A1) and an ionic group-free segment (A2). For the present invention, though referred to as an "ionic group-free segment", the segment (A2) may actually contain an ionic group in a small amount unless it has adverse influence on the advantageous effect on the invention. Hereinafter, the expression "ionic group-free" may be used in some cases in the same meaning as above.

A block copolymer according to the present invention includes at least two types of mutually incompatible segment chains, namely, a hydrophilic segment containing an ionic group and a hydrophobic segment containing no ionic group, that are connected to each other to form a polymer chain. In a block copolymer, chemically different segment chains undergo short distance interaction due to repulsion against each other, leading to phase separation into nano- or microdomains containing either segment chains. Being connected through covalent bonds, the segment chains undergo long distance interaction, leading to an arrangement of the domains in a specific orderly manner. The higher-order structures formed through aggregation of domains containing these segment chains are referred to as nano- or micro-phase-separated structures. For ion conduction in polymer electrolyte membrane, the spatial arrangement of ion-conducting segments in the film, that is, nano- or micro-phase-separated structures, have an important role. Here, a domain is a coagulated cluster of similar segments belonging to one polymer chain or a plurality of polymer chains.

The block copolymers according to the present invention can exhibit high proton conductivity even under low humidify conditions because they have a characteristic chemical structure in which the ionic group-containing segment (A1) contains a constituent unit as represented by the general formula (S1) while the polymer higher-order structures, that is, the nano- or micro-phase-separated structures, are controlled to form a proton conduction channel that has chemical durability, physical durability, high ion conductivity, and in particular, a locally increased density of sulfonic acid groups.

Various characteristics of a polymer electrolyte, including processability, domain size, crystallizability/amorphism, mechanical strength, proton conductivity, and dimensional stability can be controlled by adopting a block copolymer according to the present invention having appropriate properties including chemical structure, segment chain length, molecular weight, and ion exchange capacity.

In the block copolymers according to the present invention, the ionic group-containing segment (A1) forms a domain, allowing the formation of a polymer electrolyte material and polymer electrolyte membrane that have a high degree of proton conduction even under low humidify conditions.

The ionic groups contained in the block copolymers according to the present invention are preferably in the form of negatively charged atom groups and preferably have proton exchange ability. Preferred examples of these functional groups include sulfonic acid group, sulfonimide group, sulfuric acid group, phosphonate acid group, phosphoric acid group, and carboxylic acid group. Here, a sulfonic acid group is a group as represented by the general formula (f1) given below; a sulfonimide group is a group as represented by the general formula (f2) given below (in the general formula (f2), R represents an arbitrarily selected organic group); a sulfuric acid group is a group as represented by the general formula (f3) given below; a phosphonate acid group is a group as represented by the general formula (f4) given below; a phosphoric acid group is a group as represented by either the general formula (f5) or (f6) given below; and a carboxylic acid group is a group as represented by the general formula (f7) given below.

[Chemical formula 14]

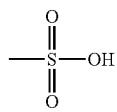

(f1)

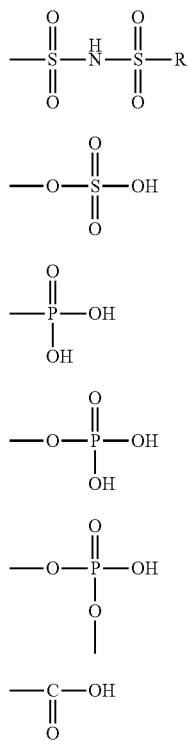

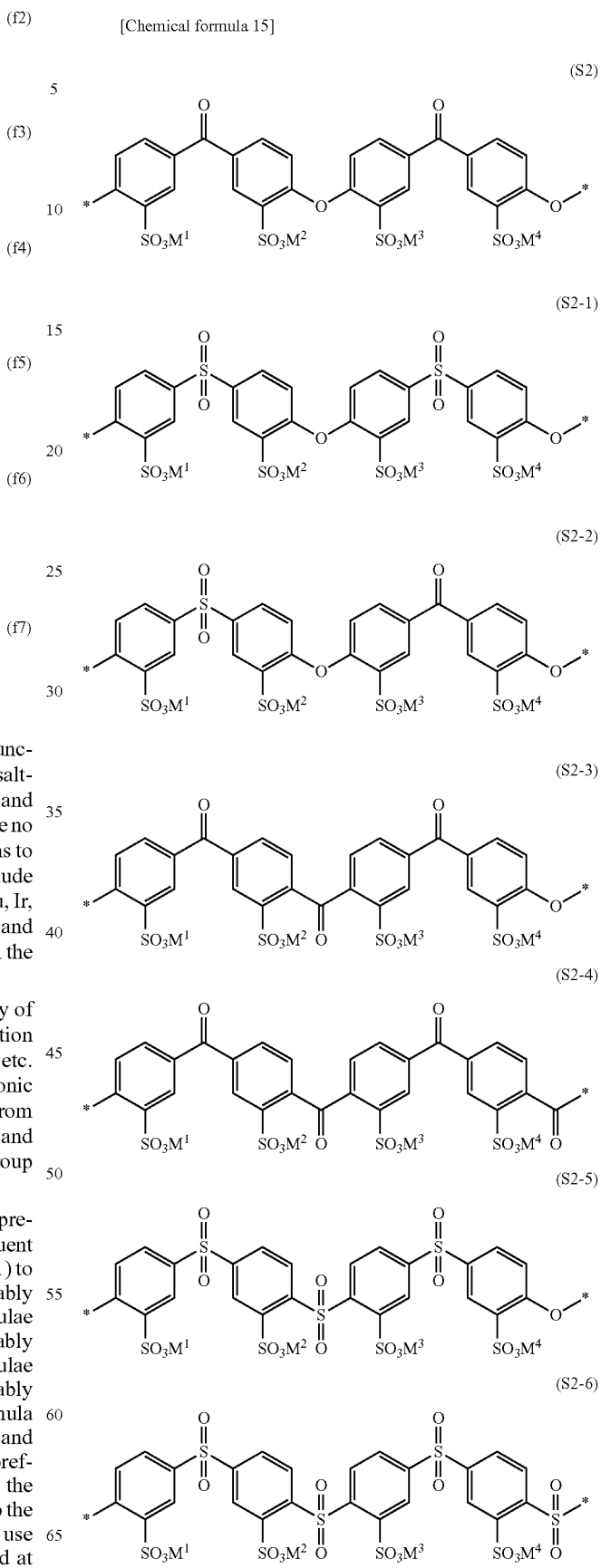

These ionic groups include those in which the above functional groups (f1) to (f7) are in the form of salts. Such salt-forming cations include arbitrarily selected metal cations and $NR_4^+$ (R is an arbitrarily selected organic group). There are no specific limitations on the valence etc. of the metal cations to be used. Specific examples of preferable metal ions include the ions of Li, Na, K, Rh, Mg, Ca, Sr, Ti, Al, Fe, Pt, Rh, Ru, Ir, and Pd. In particular, Na, K, and Li, which are low in price and easily proton-substitutable, are more preferable for use in the block copolymers according to the present invention.

A polymer electrolyte material may contain a plurality of types of these ionic groups, and an appropriate combination of them may be adopted in view of the polymer structure etc. In particular, it is more preferable to contain at least a sulfonic acid group, sulfonimide group, or sulfuric acid group from the viewpoint of their high degree of proton conductivity, and it is most preferable to contain at least a sulfonic acid group from the viewpoint of input material cost.

Specific examples of preferred constituent units as represented by the general formula (S1) include those constituent units as represented by any of the formulae (S2) and (S2-1) to (S2-8) given below. In particular, they are more preferably those constituent units as represented by any of the formulae (S2) and (S2-1) to (S2-4) given below, still more preferably those constituent units as represented by any of the formulae (S2) and (S2-1) to (S2-2) given below, and most preferably those constituent units as represented by any of the formula (S2) given below, from the viewpoint of production cost and physical durability. For the present invention, it is also preferable to use a plurality of these constituent units. Here, the position of the sulfonic acid group may differ according to the type of sulfonation agent used. It is also preferable to use constituent units having sulfonic acid groups introduced at different positions.

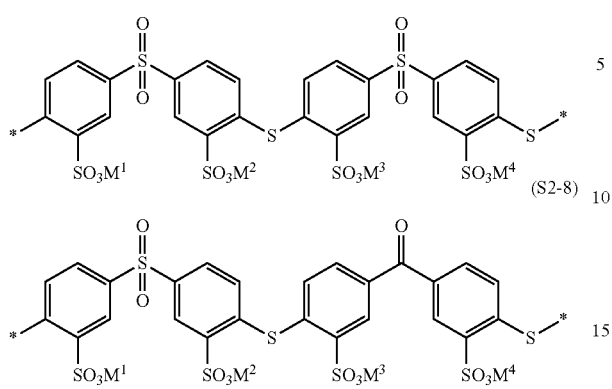

(S2-7)

(S2-8)

(In the formulae (S2) and (S2-1) to (S2-8), $M^1$ to $M^4$ represent a hydrogen, a metal cation, an ammonium cation, or a hydrocarbon group with a carbon number of 1 to 20, and each of $M^1$ to $M^4$ may be a plurality of groups. Here, * bonding sites to constituent units as represented by any of the general formulae (S2) and (S2-1) to (S2-8) or to other constituent units.)

Next, the ionic group-containing segments (A1) are described.

The ionic group-containing segments (A1) are characterized by containing a constituent unit as represented by the general formula (S1), and they preferably have chemical stability, an increased acidity due to electron-withdrawing effect, and a high density of introduced sulfonic acid groups so as to form a block copolymer having high proton conductivity under low humidify conditions.

Specific examples of the ionic group-containing segments (A1) include those which contain at least a constituent unit as represented by the general formula (Q1) and/or (Q2) and a constituent unit as represented by the general formula (Q4), and may arbitrarily contain a constituent unit as represented by the general formula (Q3). Furthermore, it is preferable that the constituent units as represented by the general formula (Q1), (Q2), (Q3), or (Q4) have a molar fraction relation as represented by the formula (T1) given below:

$$0 \leq Y < X < Z < 1 \quad (T1)$$

where, relative to the total molar quantity of the constituent units as represented by the general formulae (Q1) to (Q4), X is the sum of the molar fractions of the constituent units represented by the general formula (Q1) and (Q2) while Y and Z are respectively the molar fractions of the constituent units represented by the general formula (Q3) or (Q4), and where the relation X+Y+Z=1 is met.

[Chemical formula 17]

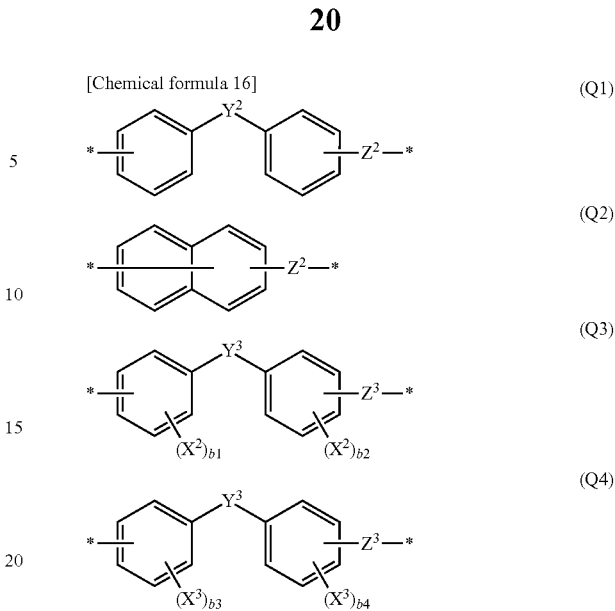

(In the general formulae (Q1) to (Q4), $X^2$'s and $X^3$'s are independently an ionic group; $Y^2$ is an electron-withdrawing group or direct bonding; $Y^3$ is electron-withdrawing group; and $Z^2$ and $Z^3$ are each an electron-withdrawing group, —O—, or —S—. Furthermore, $b_1$ and $b_2$ are integers that meet the relation $b_1+b_2=1$, and $b_3$ and $b_4$ are integers that meet the relation $2 \leq b_3+b_4 \leq 8$. In the general formulae (Q1) to (Q4), each phenylene group may be substituted with an arbitrarily selected group other than an ionic group. Here, * indicates bonding sites to constituent units as represented by any of the general formulae (Q1) to (Q4) or to other constituent units.)

The content of the constituent units represented by any of the general formulae (Q1) to (Q4) should preferably be as high as possible from the viewpoint of chemical stability and low-humidify proton conductivity. Relative to the total quantity of the ionic group-containing segments (A1), it is preferably 50 mol % or more, more preferably 70 mol % or more, and most preferably 90 mol % or more. An ionic group-containing segment (A1) preferably consists only of constituent units as represented by any of these general formulae (Q1) to (Q4), but may be copolymerized with other appropriate constituent units as required.

In an ionic group-containing segment (A1), the molar fraction Y of the constituent units represented by the general formula (Q3) should preferably be low from the viewpoint of low-humidify proton conductivity and physical durability, and it is more preferably 10 mol % or less, and most preferably 0 mol %.

In the case where the molar fraction Y of the constituent units represented by the general formula (Q3) is 0 mol %, specific examples of the ionic group-containing segments (A1) include those as represented by any of the general formulae (Q5-1) to (Q5-10) given below.

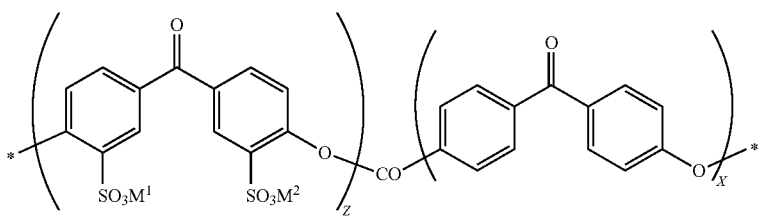

(Q5-1)

-continued
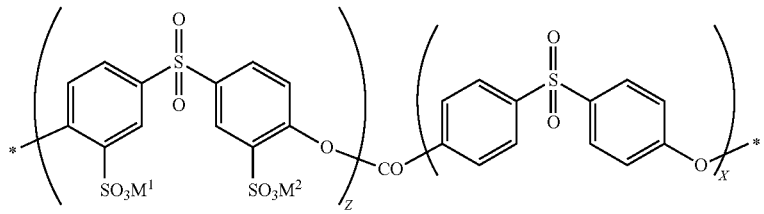
(Q5-2)
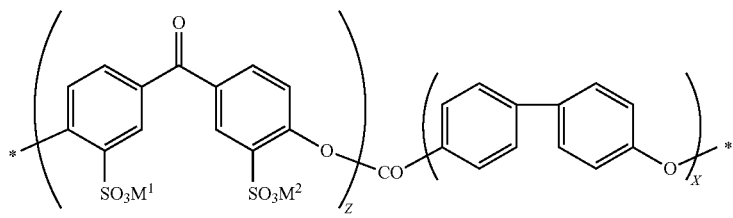
(Q5-3)
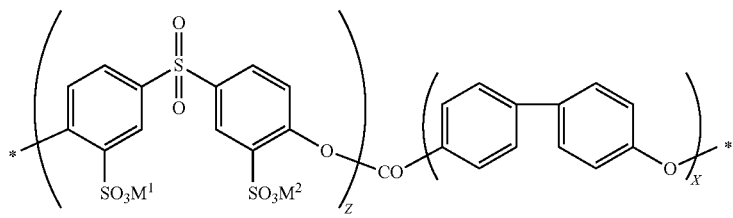
(Q5-4)
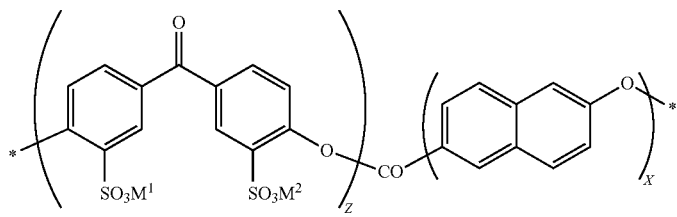
(Q5-5)
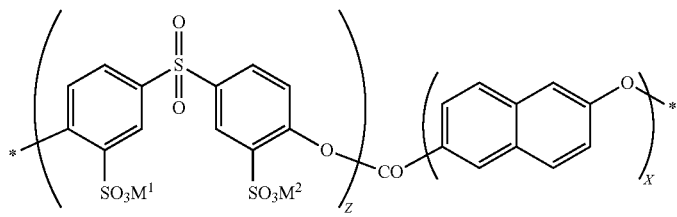
(Q5-6)
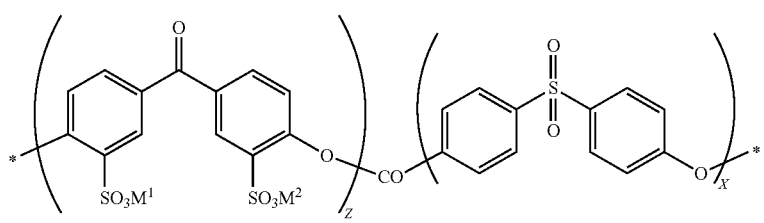
(Q5-7)
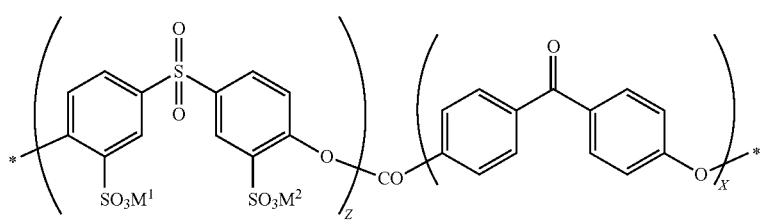
(Q5-8)

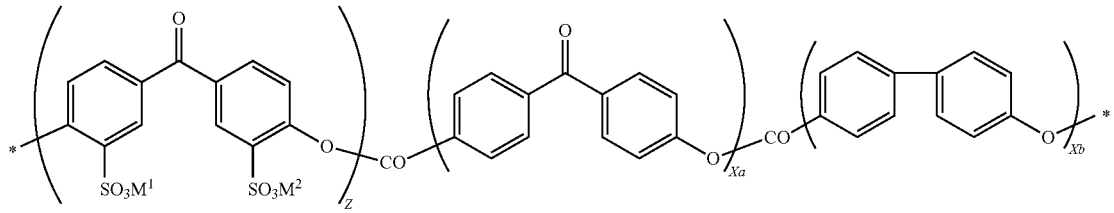

(Q5-9)

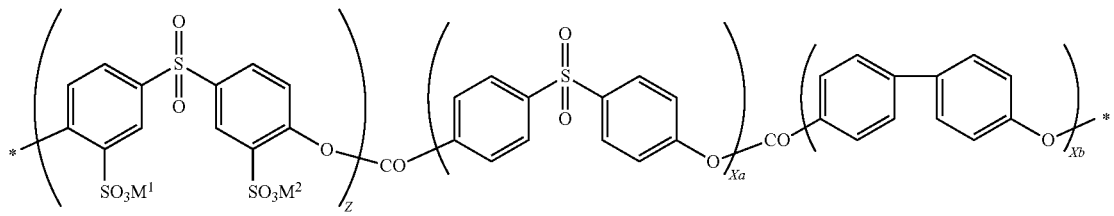

(Q5-10)

(Here, X, Xa, Xb, and Z are molar fractions and meet the relation 0<X<Z<1. The relation X=($X_a$+$X_b$) is met in formulae (Q5-9) and (Q5-10). Furthermore, $M^1$ and $M^2$ are a cation selected from the group consisting of a hydrogen, a metal cation, an ammonium cation, or a hydrocarbon group with a carbon number of 1 to 20.)

To meet the relation 0<X<Z<1, the molar fraction Z of the constituent units represented by the general formula (Q4) is required to be more than 50 mol % (0.5<Z), and it is preferably 60 mol % or more (0.6≤Z) and more preferably 70 mol % or more (0.7≤Z) from the viewpoint of low-humidify proton conductivity.

Described next are specific synthesis methods for the ionic group-containing segments (A1) used for the present invention. There are no specific limitations on the synthesis method to be used for producing an ionic group-containing segment (A1) as long as a substantially adequate molecular weight can be obtained, and specific examples include, for example, synthesis through an aromatic nucleophilic substitution reaction of an aromatic active dihalide compound and a divalent phenol compound, and synthesis through an aromatic nucleophilic substitution reaction of a halogenated aromatic phenol compound.

To synthesize a constituent unit as represented by the above formula (S1), namely, a constituent unit composed mainly of a sulfonic acid group introduced into each of four or more continuously connected benzene rings, there are two typical methods as follows: (i) copolymerization of a multi-sulfonated dihalide as represented by the formula (SM1) given below and a bisphenol compound, and (ii) polymerization of an oligomer containing no sulfonic acid group as represented by the formula (S3-0) given below, followed by its post-sulfonation. However, note that the present invention is not limited to these examples.

[Chemical formula 18]

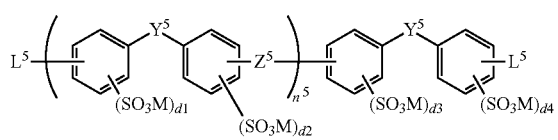

(SM1)

(In the general formula (SM1), $n^5$ is an integer of 1 or greater and not greater than 10, $d_1$ to $d_4$ are each an integer of 1 or greater. M's are independently a hydrogen, a metal cation, an ammonium cation, or a hydrocarbon group with a carbon number of 1 to 20 and $L^5$'s are independently a halogen atom. Furthermore, $Y^5$ is an electron-withdrawing group and $Z^5$ is an electron-withdrawing group, —O—, —S—, or direct bonding.) Here, $d_1$ to $d_4$, $Y^5$, and $Z^5$ may represent two or more different groups or numbers.)

[Chemical formula 19]

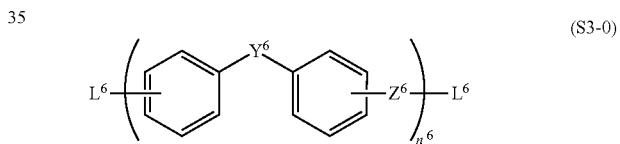

(S3-0)

(In the general formula (S3-0), $n^6$ represents the number of repetitions that is greater than 10, and independently $Y^6$ is an electron-withdrawing group and $Z^6$ is an electron-withdrawing group, —O—, —S—, or direct bond. $L^6$'s are independently a halogen atom. $Y^6$ and $Z^6$ may represent two or more different groups.)

Of the above two methods, method (i) is more preferable in terms of production cost while method (ii) is more preferable in terms of the density of sulfonic acid group.

Here, specific examples of $L^5$ and $L^6$ include fluorine, chlorine, bromine, and iodine, of which fluorine and chlorine are more preferable in terms of reactivity, of which fluorine is the most preferable. Specific examples of the electron-withdrawing groups $Y^5$ and $Y^6$ include —CO—, —CONH—, —($CF_2$)$_n$— (n is an integer from 1 to 10), —C($CF_3$)$_2$—, —COO—, —$SO_2$—, —SO—, and —PO($R^1$)— ($R^1$ is an arbitrarily selected organic group). In particular, —CO— and —$SO_2$— are more preferable in terms of chemical stability and cost, and —CO— is the most preferable in terms of physical durability.

Specific examples of $Z^5$ and $Z^6$ include —CO—, —CONH—, —($CF_2$)$_n$— (n is an integer from 1 to 10), —C($CF_3$)$_2$—, —COO—, —$SO_2$—, —SO—, —PO($R^1$)— ($R^1$ is an arbitrarily selected organic group), and other electron-withdrawing groups, as well as —O—, —S—, and direct bonding, of which —O—, —S—, and direct bonding are more preferable, of which —O— is the most preferable, in terms of cost and physical durability. Furthermore, $n^5$ is more preferably an integer from 1 to 10, still more preferably from 1 to 3, and most preferably 1 or 2, in terms of easiness of synthesis. The number $n^6$ is more preferably an integer of greater than 10 from the viewpoint of proton conductivity under low humidify conditions and still more preferably an integer of greater than 10 and not greater than 300 from the viewpoint of production cost and physical durability.

The multi-sulfonated dihalide represented by the above formula (SM1) is more preferably one as represented by the general formula (M2) given below from the viewpoint of production cost and chemical stability. It is still more preferably an aromatic sulfonic acid derivative as represented by the general formula (M3) given below.

[Chemical formula 20]

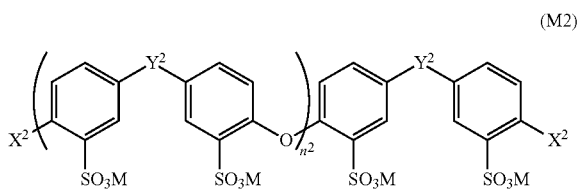

(M2)

(In the general formula (M2), $n^2$ is an integer of 1 or greater, and M's are independently a hydrogen, a metal cation, an ammonium cation, or a hydrocarbon group with a carbon number of 1 to 20. $X^2$'s are independently F or Cl, and $Y^2$ is —CO— or —SO$_2$—.)

[Chemical formula 21]

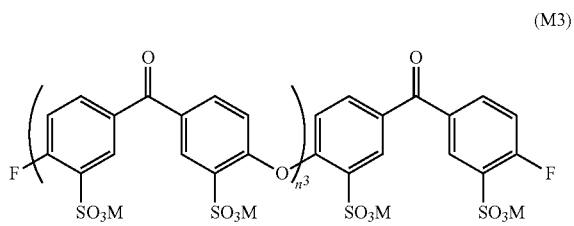

(M3)

(In the general formula (M4), $n^3$ is an integer from 1 to 3, and M's are independently a hydrogen, a metal cation, an ammonium cation, or a hydrocarbon group with a carbon number of 1 to 20.)

In addition to those represented by the formula (SM1) given above to be used as monomers, preferable aromatic active dihalide compounds to be copolymerized in an ionic group-containing segment (A1) also include compounds produced by introducing an ionic acid group into an aromatic active dihalide compound. Specific examples of preferred monomers that contain a sulfonic acid group as ionic group include, but not limited to, 3,3'-disulfonate-4,4'-dichlorodiphenyl sulfone, 3,3'-disulfonate-4,4'-difluorodiphenyl sulfone, 3,3'-disulfonate-4,4'-dichlorodiphenyl ketone, 3,3'-disulfonate-4,4'-difluorodiphenyl ketone, 3,3'-disulfonate-4,4'-dichlorodiphenyl phenyl phosphine oxide, and 3,3'-disulfonate-4,4'-difluorodiphenyl phenyl phosphine oxide.

The density of ionic groups in the aromatic active dihalide compounds can also be controlled by copolymerizing those containing an ionic group and those containing no ionic group. For a block (A1) which contains an ionic group according to the present invention, however, it is more pref-erable to avoid the copolymerization with an aromatic active dihalide compound containing no ionic group from the viewpoint of securing continuous proton conduction paths.

Specific examples of preferred aromatic active dihalide compounds that contain no ionic group include 4,4'-dichlorodiphenyl sulfone, 4,4'-difluorodiphenyl sulfone, 4,4'-dichlorodiphenyl ketone, 4,4'-difluorodiphenyl ketone, 4,4'-dichlorodiphenyl phenyl phosphine oxide, 4,4'-difluorodiphenyl phenyl phosphine oxide, 2,6-dichlorobenzo nitrile, and 2,6-difluoro benzonitrile. Of these, 4,4'-dichlorodiphenyl ketone and 4,4'-difluorodiphenyl ketone are more preferable from the viewpoint of crystallizability improvement, mechanical strength, physical durability, and hot water resistance, and 4,4'-difluorodiphenyl ketone is the most preferable from the viewpoint of polymerization activity. These aromatic active dihalide compounds can be used singly, but it is also possible to use a plurality of these aromatic active dihalide compounds in combination.

Copolymerizable compounds that contain no ionic group include halogenated aromatic hydroxyl compounds. There are no specific limitations on these halogenated aromatic hydroxyl compounds, and usable examples include 4-hydroxy-4'-chlorobenzophenone, 4-hydroxy-4'-fluorobenzophenone, 4-hydroxy-4'-chlorodiphenyl sulfone, 4-hydroxy-4'-fluorodiphenyl sulfone, 4-(4'-hydroxybiphenyl) (4-chlorophenyl) sulfone, 4-(4'-hydroxybiphenyl) (4-fluorophenyl) sulfone, 4-(4'-hydroxybiphenyl) (4-chlorophenyl) ketone, 4-(4'-hydroxybiphenyl) (4-fluorophenyl) ketone. These compounds can be used singly, but it is also possible to use mixtures of a plurality thereof. Furthermore, in the reaction of an activated dihalogenated aromatic compound and an aromatic dihydroxy compound, these halogenated aromatic hydroxyl compounds may be added to the reaction to synthesize an aromatic polyether compound.

A ionic group-containing segment (A1) that includes at least a constituent unit as represented by the general formula (Q1) and/or (Q2) and a constituent unit as represented by the general formula (Q4) can be synthesized through aromatic nucleophilic substitution reaction of an aromatic sulfonic acid derivative (dihalide compound) as represented by the general formula (M2) and a divalent phenol compound as represented by any of the general formulae (Y-1), (Y-3), (Y-11), and (Y-14). Here, preferred examples also include divalent thiol compounds in the form of heteroatom derivatives of these divalent phenol compounds.

In particular, divalent phenol compounds as represented by the general formula (Y-11) or (Y-14) are more preferable from the viewpoint of a low electronic density in the benzene rings and electrophilic reaction depression effect of the hydroxyradicals, and divalent phenol compounds as represented by the general formula (Y-14) are the most preferable from the viewpoint of water resistance and crystallizability.

There are no specific limitations on the divalent phenol compound to be used as a block copolymer for the present invention, and an appropriate one may be selected taking its chemical stability, physical durability, cost, etc. into consideration. Here, such a divalent phenol compound containing a sulfonic acid group may be used as a monomer unless it is introduced within a range or at a position that has adverse influence on the advantageous effect of the invention, but it is preferable to use one that contains no sulfonic acid group from the viewpoint of reactivity. Specific examples of other divalent phenols include those divalent phenol compounds as represented by any of the general formulae (Y-2), (Y-4) to (Y-10), (Y-12), (Y-13), and (Y-15) to (Y-30).

For example, a constituent unit produced through an aromatic nucleophilic substitution reaction of an aromatic sulfonic acid derivative (dihalide compound) as represented by the general formula (M3) and a divalent phenol compound as represented by the general formula (Y-14) or (Y-1) has a structure as represented by the general formula (P1) or (P2) given below, and it serves as a particularly preferable constituent unit of an ionic group-containing segment (A1) in a block copolymer according to the present invention. Here again, if the constituent units as represented by the general formula (P1) or (P2) account for only less than 20 wt %, it is not preferable because in that case, the proton conductivity under low humidify conditions will not be high enough to achieve the advantageous effect of the invention.

should be contained. $Y^7$ is an electron-withdrawing group and $Z^7$ is an electron-withdrawing group, —O—, —S—, or direct bonding. Here, * indicates bonding sites to constituent units as represented by the general formula (NP1) or to other constituent units.)

Here, specific examples of the electron-withdrawing group $Y^7$ include —CO—, —CONH—, —$(CF_2)_n$— (n is an integer from 1 to 10), —$C(CF_3)_2$—, —COO—, —$SO_2$—, —SO—, and —$PO(R^1)$— ($R^1$ is an arbitrarily selected organic group). In particular, —CO— and —$SO_2$— are more preferable in terms of chemical stability and cost, and —CO— is the most preferable in terms of physical durability.

[Chemical formula 22]

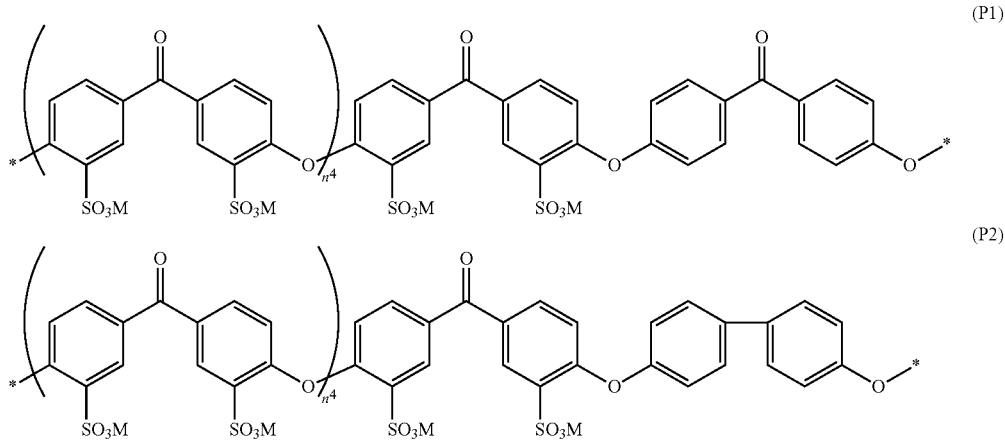

(in the general formulae (P1) and (P2), $n^4$ is an integer of 1 to 3, and M's are independently a hydrogen, a metal cation, an ammonium cation, or a hydrocarbon group with a carbon number of 1 to 20. Here, * indicates bonding sites to constituent units as represented by either the general formula (P1) or (P2) or to other constituent units.)

Furthermore, $n^4$ is more preferably an integer from 1 to 5, still more preferably 1 or 2, and most preferably 1, in terms of easiness of synthesis.

Next, ionic group-free segments (A2) are described in detail.

The ionic group-free segment (A2) is preferably a constituent unit that has chemical stability and crystallizability due to strong intermolecular coagulation because such a constituent unit serves to produce a block copolymer that is high in mechanical strength, dimensional stability, and physical durability.

In the block copolymers according to the present invention, the ionic group-free segment (A2) preferably contains a constituent unit as represented by the general formula (NP1) given below.

[Chemical formula 23]

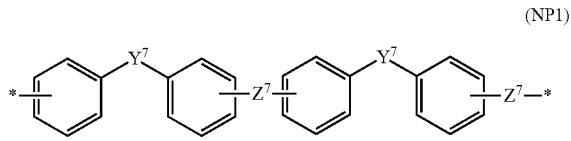

(Arbitrary substitution may be performed at the positions shown in the general formula (NP1), but no ionic groups Specific examples of $Z^7$ include —CO—, —CONH—, —$(CF_2)_n$— (n is an integer from 1 to 10), —$C(CF_3)_2$—, —COO—, —$SO_2$—, —SO—, —$PO(R^1)$— ($R^1$ is an arbitrarily selected organic group), and other electron-withdrawing groups, as well as —O—, —S—, and direct bonding, of which —O— and —S— are more preferable, of which —O— is the most preferable, in terms of cost and physical durability.

The constituent units represented by the general formula (NP1) are high in chemical stability due to the effect of the electron-withdrawing group $Y^7$ and can form a block copolymer with an increased mechanical strength and water resistance, so that three dimensional reinforcing network is formed, leading to high physical durability.

In the ionic group-free segment (A2), the content of the constituent units represented by the general formula (NP1) should be high from the viewpoint of physical durability and chemical stability. It is preferably more than 50 mol %, more preferably 60 mol % or more, particularly preferably 65 mol % or more, and most preferably 75 mol % or more.

Specific examples of preferable constituent units as represented by the general formula (NP1) contained in an ionic group-free segment (A2) include those constituent units as represented by any of the general formulae (NP2), (NP3), and (NP4-1) to (NP4-8) given below from the viewpoint of material availability. In particular, from the viewpoint of mechanical strength, dimensional stability, and physical durability that are high due to high crystallizability, constituent units as represented by the formulae (NP3), (NP4-1), or (NP4-2) given below are still more preferable, of which constituent units as represented by the formula (NP3) given below are the most preferable. In the ionic group-free segment (A2), the content of the constituent units represented by the general formula (NP2) should be high. It is preferably more than 20 mol %, more preferably 50 mol % or more, and most preferably 80 mol % or more. A content of less than 20 mol % is not preferable because in that case, the mechanical strength, dimensional stability, and physical durability developed by crystallizability will not be high enough to achieve the advantageous effect of the invention.

[Chemical formula 24]

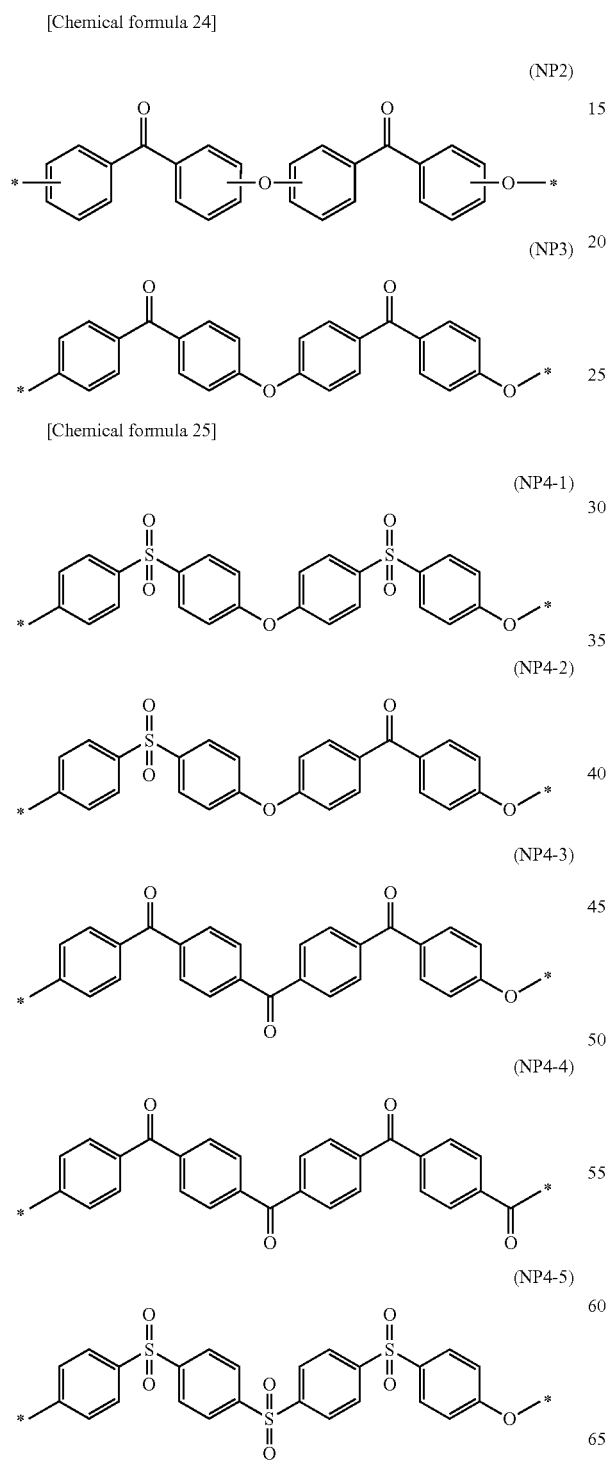

[Chemical formula 25]

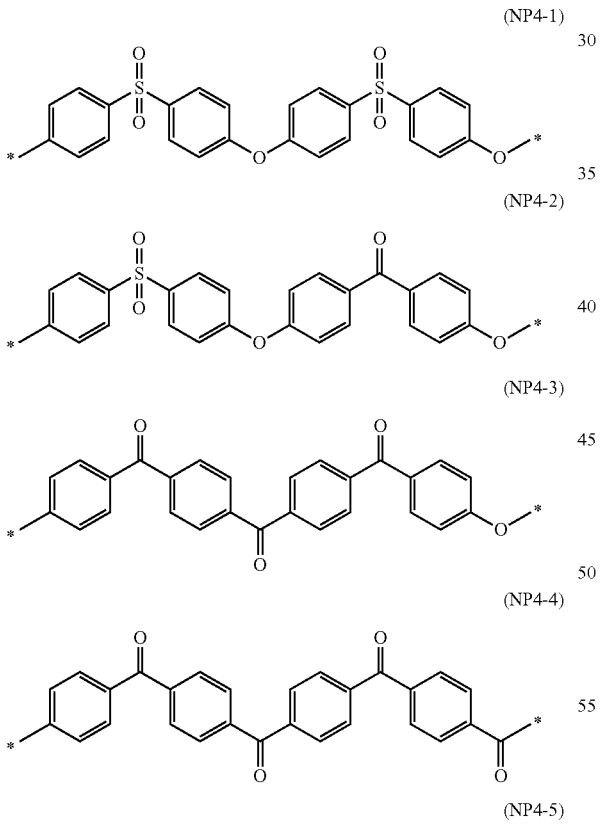

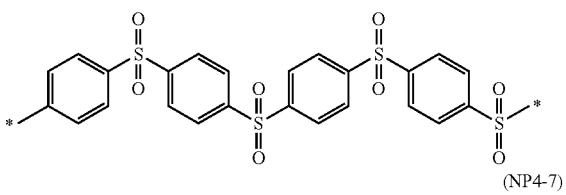

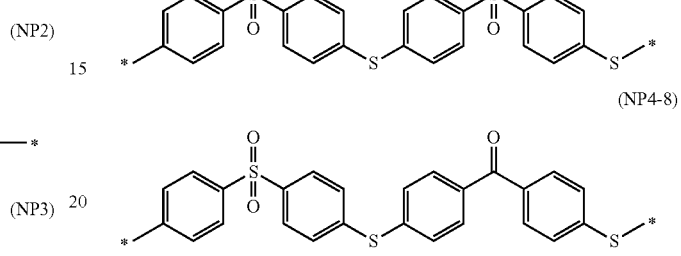

For the ionic group-free segment (A2), preferable constituent units, other than the constituent units represented by the general formula (NP1), to be used for copolymerization include aromatic polyether based polymers containing a ketone group, that is, constituent units as represented by the general formula (NQ1) given below, that contain no ionic group.

[Chemical formula 26]

(In the general formula (NQ1), $Z^1$ and $Z^2$ each represent a divalent organic group or a plurality of divalent organic groups containing an aromatic ring but containing no ionic group. Here, a and b independently represent a positive integer.)

With respect to preferable organic groups to be used as $Z^1$ and $Z^2$ in the general formula (NQ1), it is more preferable that $Z^1$ be a phenylene group while at the same time, $Z^2$ be at least one represented by any of the general formula (X-1), (X-2), (X-4), and (X-5) given below. Furthermore, they may be substituted with a group other than an ionic group, but they are preferably non-substituted from the viewpoint of crystallizability improvement. $Z^1$ and $Z^2$ are more preferably a phenylene group and most preferably a p-phenylene group.

[Chemical formula 27]

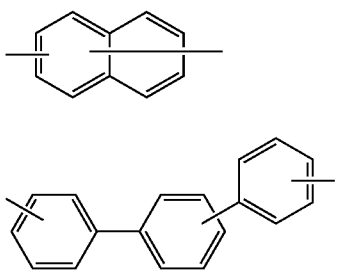

(X-4)

(X-5)

(The divalent phenol compounds represented by any of the general formula (X-1), (X-2), (X-4), and (X-5) may be substituted appropriately, but no ionic groups should be contained.)

Specific examples of preferred constituent units as represented by the general formula (NQ1) include those constituent units as represented by any of the general formulae (NQ2) to (NQ7) given below, but they are not limited thereto, and others may be adopted appropriately taking crystallizability and mechanical strength into consideration. In particular, from the viewpoint of crystallizability and production cost, constituent units as represented by the general formula (NQ1) are more preferably in a form as represented by the general formula (NQ2), (NQ3), (NQ6), or (NQ7) and most preferably in a form as represented by the general formula (NQ2) or (NQ7).

[Chemical formula 28]

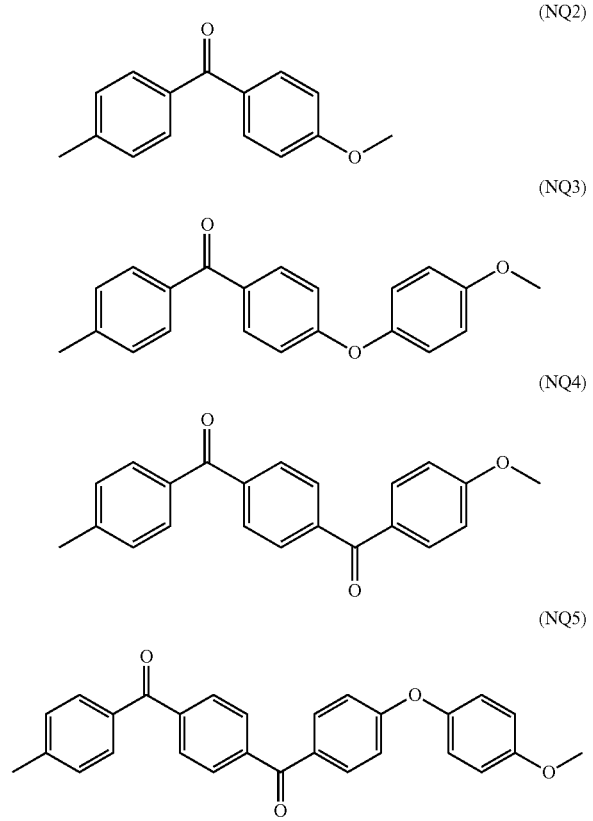

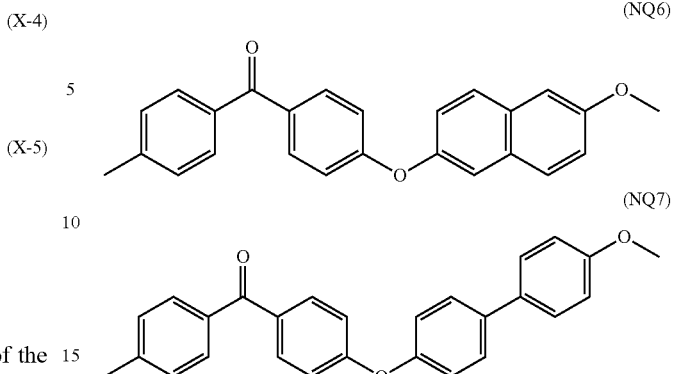

In the general formulae (NQ2) to (NQ7), all bonds are at the para position, but these bonds may occur at other positions, namely, ortho or meta, as long as the constituent units have crystallizability. However, the para position is preferable from the viewpoint of crystallizability.

In addition, it is preferable for the block copolymers according to the present invention to further contain one or more linker portions for connection between ionic group-containing segments (A1) and ionic group-free segments (A2).

Here, a linker for the present invention is defined as a portion that acts for connection between an ionic group-containing segment (A1) and an ionic group-free segment (A2) and has a chemical structure different from that of the ionic group-containing segment (A1) or from that of the ionic group-free segment (A2). This linker acts particularly favorably to obtain a block copolymer according to the present invention because it serves for connection between different segments while depressing randomization, segment severance, or side reaction caused by ether exchange reaction. If such a linker does not exist, segment severance, such as by randomization, may take place in some cases, preventing adequate achievement of the advantageous effect of the present invention.

A linker to be used for the present invention is required to be a highly reactive compound that can connect different segments together while depressing randomization and segment severance caused by ether exchange reaction, and specific examples preferred for the present invention include decafluorobiphenyl, hexafluorobenzene, 4,4'-difluorodiphenyl sulfone, and 2,6-difluorobenzonitrile, though the present invention is not limited thereto. Using a polyfunctional linker, such as decafluorobiphenyl and hexafluorobenzene, while controlling the reaction conditions serves to produce a branched block copolymer. In that case, either a linear structured block copolymer or a branch structured block copolymer can be produced as desired by controlling the feed ratio between a polymer that has an unsulfonated segment as represented by the formula (NP1) and a polymer that has a sulfonated segment as represented by the formula (S1).

If a block copolymer according to the present invention has a sulfonic acid group, its ion exchange capacity is preferably 0.1 to 5 meq/g, more preferably 1.5 meq/g or more, and most preferably 2 meq/g or more, from the viewpoint of the balance between proton conductivity and water resistance. On the other hand, it is preferably 3.5 meq/g or less and most preferably 3 meq/g or less. The proton conductivity may not be sufficiently high if the ion exchange capacity is less than 0.1 meq/g while the water resistance may not be sufficiently high if it is more than 5 meq/g.

For the block copolymers according to the present invention, the molar content ratio (A1/A2) between an ionic group-containing segment (A1) and an ionic group-free segment (A2) is more preferably 0.2 or more, still more preferably 0.33 or more, and most preferably 0.5 or more. On the other hand, the molar content ratio (A1/A2) is more preferably 5 or less, still more preferably 3 or less, and most preferably 2 or less. A molar ratio A1/A2 of less than 0.2 or more than 5 is not preferable because in those cases, the advantageous effect of the invention may not be achieved sufficiently, leading to insufficient proton conductivity under low humidify conditions, insufficient hot water resistance, or insufficient physical durability.

Here, the molar content ratio (A1/A2) is defined as the ratio between the number of moles of the constituent units existing in the segment (A1) and the number of moles of the constituent units existing in the segment (A2). For the present invention, as described previously, a constituent unit is defined as one including four benzene rings connected in the backbone chain direction as seen in the constituent units represented by the general formulae (S1) and (NP1). For example, in the case where the segment (A1) includes a constituent unit (S1) that contains an ionic group while the segment (A2) includes a constituent unit (NP1) that contains no ionic group, it is the ratio between the values calculated by dividing the number average molecular weight of each segment by the molecular weight of the corresponding constituent unit (S1) or (NP1). Here, if a segment is a random copolymer, alternate copolymer, or block copolymer, instead of a homopolymer, it is defined as the ratio between the values obtained by dividing the number average molecular weight of the segments by the average molecular weight that takes the molar ratios of the different portions into account.

The ion exchange capacity of an ionic group-containing segment (A1) is preferably high from the viewpoint of the proton conductivity under low humidify conditions, and it is more preferably 2.5 meq/g or more, still more preferably 3 meq/g or more, and most preferably 3.5 meq/g or more. On the other hand, it is preferably 6.5 meq/g or less, still more preferably 5 meq/g or less, and most preferably 4.5 meq/g or less. The proton conductivity under low humidify conditions will not be sufficiently high if the ion exchange capacity of the ionic group-containing segment (A1) is less than 2.5 meq/g while the hot water resistance and physical durability will not be sufficiently high if it is more than 6.5 meq/g.

The ion exchange capacity of an ionic group-free segment (A2) is preferably low from the viewpoint of hot water resistance, mechanical strength, dimensional stability, and physical durability, and it is more preferably 1 meq/g or less, still more preferably 0.5 meq/g or less, and most preferably 0.1 meq/g or less. It is not preferable for an ionic group-free segment (A2) to have an ion exchange capacity of more than 1 meq/g because its hot water resistance, mechanical strength, dimensional stability, and physical durability will not be sufficiently high.

Here, the ion exchange capacity is defined as the number of moles of the sulfonic acid group introduced per unit dry weight of a block copolymer, polymer electrolyte material, and polymer electrolyte membrane, and the degree of sulfonation increases with this capacity. The ion exchange capacity can be determined by methods such as element analysis and neutralization titration. When using the element analysis method, it can be calculated from the S/C ratio, but its determination may be difficult in some cases where, for example, sulfur sources other than sulfonic acid groups are contained. For the present invention, therefore, the ion exchange capacity is defined as one determined by the neutralization titration method. In some embodiments, the polymer electrolyte materials and polymer electrolyte membranes according to the present invention may be in the form of a composite material composed of a block copolymer according to the present invention and other components, as described later. In such cases as well, the ion exchange capacity is calculated based on the total quantity of the composite material.

The neutralization titration method may be performed as follows. Here, three measurements are made and their average is used.

(1) A specimen of electrolyte membrane is subjected to proton substitution, washed adequately with purified water, wiped to remove water from the film surface, vacuum-dried at 100° C. for 12 hours or more, and subjected to dry weight measurement.

(2) A 50 mL amount of a 5 wt % sodium sulfate aqueous solution is added to the electrolyte, which is then left to stand for 12 hours and subjected to ion exchange.

(3) The resulting sulfuric acid is titrated with a 0.01 mol/L sodium hydroxide aqueous solution. A commercial 0.1 w/v % phenolphthalein solution for titration is added as indicator, and the titration is finished when the solution turns to light reddish violet.

(4) The ion exchange capacity is calculated by the equation given blow.

Ion exchange capacity (meq/g)=[concentration of sodium hydroxide aqueous solution (mmol/mL)× titrant quantity (mL)]/dry weight of specimen (g)

A block copolymer according to the present invention thus obtained has a polystyrene equivalent weight average molecular weight of 50,000 to 1,000,000, preferably 100,000 to 500,000. If it is less than 50,000, molded film may suffer cracking, possibly leading to inadequate mechanical strength, physical durability, or solvent resistance. If it is more than 1,000,000, on the other hand, there will be problems such as insufficient solubility and high solution viscosity, leading to poor processability.

The number average molecular weight of an ionic group-containing segment (A1) and that of an ionic group-free segment (A2) are associated with the domain sizes of phase-separated structures, and they are preferably 5,000 or more, more preferably 10,000 or more, and most preferably 15,000 or more, from the viewpoint of the balance between the proton conductivity under low humidify conditions and physical durability. On the other hand, it is preferably 50,000 or less, more preferably 40,000 or less, and most preferably 30,000 or less.

Methods available to introduce an ionic group to produce a block copolymer according to the present invention include carrying out polymerization of monomers that have an ionic group and carrying out a polymer reaction that works to introduce an ionic group.

The above method of carrying out polymerization of monomers that have an ionic group simply uses monomers consisting of repeating units containing an ionic group. An example of the method is described in Journal of Membrane Science, 197, 2002, p. 231-242. This method is particularly preferable because of easy control of the ion exchange capacity of the polymer and high industrial applicability.

The use of a polymer reaction to introduce an ionic group is described below with reference to examples. The introduction of a phosphonate acid group into an aromatic polymer can be carried out by, for example, the process described in Polymer Preprints, Japan, 51, 2002, p. 750. The introduction of a phosphoric acid group into an aromatic polymer can be carried out by, for example, subjecting an aromatic polymer having a hydroxyl group to a phosphate ester forming reaction. The introduction of a carboxylic acid group into an aromatic polymer can be carried out by, for example, oxidizing an aromatic polymer having an alkyl group or hydroxyalkyl group. The introduction of a sulfuric acid group into an aromatic polymer can be carried out by, for example, subjecting an aromatic polymer having a hydroxyl group to a sulfate ester forming reaction. To sulfonate an aromatic polymer, that is, to introduce a sulfonic acid group, the methods proposed, for example, in Japanese Unexamined Patent Publication (Kokai) No. HEI-2-16126 and Japanese Unexamined Patent Publication (Kokai) No. HEI-2-208322 can be used.

Specifically, sulfonation can be achieved by, for example, reacting an aromatic polymer with a sulfonation agent such as chlorosulfonic acid in an appropriate solvent such as chloroform or reacting it in concentrated sulfuric acid or fuming sulfuric acid. There are no specific limitations on the sulfonation agent as long as it serves to sulfonate an aromatic polymer, and others than above include sulfur trioxide. When this method is used to sulfonate an aromatic polymer, the degree of sulfonation can be controlled by changing the amount of the sulfonation agent, reaction temperature, and reaction time. Introduction of a sulfonimide group into an aromatic polymer can be carried out by, for example, reacting a sulfonic acid group and a sulfone amide group.

The sulfonic acid group-containing polymers and block copolymers described above can work favorably as polymer electrolyte materials. These polymer electrolyte materials are favorably used particularly for polymer electrolyte form article. For the present invention, the term "polymer electrolyte form article" refers to a form article, containing a polymer electrolyte material according to the present invention. Polymer electrolyte form article according to the present invention can be in a variety of forms such as films (including films and film-like materials), plates, fibers, hollow yarns, particles, bulky, microporous materials, coatings, and foams, depending intended uses. They can be applied to different uses as they serve to increase the degree of design freedom for polymers and improving various characteristics including mechanical characteristics and solvent resistance. In particular, the polymer electrolyte form article work effectively in the form of film.

When polymer electrolyte materials according to the present invention are used in polymer electrolyte fuel cells, they can work effectively in the form of polymer electrolyte membrane or electrode catalyst layers. In particular, they are used favorably as polymer electrolyte membrane. It is because they are usually used in the form of film to serve as polymer electrolyte membrane and electrode catalyst layer binder when applied to polymer electrolyte fuel cells.

Polymer electrolyte form article according to the present invention can be applied to various uses. For example, they serve in various fields including extracorporeal circulation columns, artificial skin, other medical materials, filters, chlorine-resistant reverse osmosis films, other ion exchange resin materials, various structural members, electrochemical materials, humidification films, fog-resistant films, antistatic films, solar battery films, and gas barriers material. They are also useful for artificial muscles and actuator materials. In particular, they serve favorably for various electrochemical uses. Such electrochemical uses include, for example, fuel cells, redox flow batteries, water electrolytic equipment, and chloroalkali electrolytic equipment, of which fuel cells are the most preferable application.

Methods for producing polymer electrolyte form article according to the present invention are described in detail below.

For example, a polymer electrolyte form article according to the present contains a constituent unit as represented by the general formula (NP2) and is formed of a block copolymer consisting of an ionic group-free segment (A2) and an ionic group-containing segment (A1). Of these, the ionic group-free segment (A2) is a crystalline segment, and therefore, it can be produced at least by introducing protective groups into an ionic group-free segment (A2) to form a block copolymer precursor and removing at least part of the protective groups from the molded material. Compared to random copolymers, block copolymers tend to suffer from poor processability due to crystallization of the domain-forming polymer, and therefore, it is preferable to introduce protective groups at least into the ionic group-free segment (A2) to improve the processability and also preferable to introduce protective groups into the ionic group-containing segment (A1) if the processability is low.

Specific examples of protective groups to be used for the present invention include those protective groups generally used for organic synthesis. These protective groups, which are substituent groups to be introduced temporarily and to be removed in a later step, serve to protect highly reactive functional groups by making them inactive to a subsequent reaction and are removed after the reaction to restore the original functional groups. That is, the protective group is paired with a functional group to be protected. For example, a t-butyl group may be used as protective group for a hydroxyl group, but the t-butyl group is not called a protective group if it is introduced in an alkylene chain. A reaction for introducing a protective group is referred to as protection (reaction) while a reaction for removing it is referred to as deprotection (reaction).

Such protect reactions are described in detail in, for example, Protective Groups in Organic Synthesis, Theodora W. Greene, John Wiley & Sons, Inc., 1981, and they have been used favorably. Appropriate ones can be selected taking into account the reactivity and yield of the protection reaction and deprotection reaction, stability of the protective group-containing compound, production cost, etc. In a polymerization reaction, protective groups may be introduced in different appropriate stages, including monomers, oligomers, and polymers.

Specific examples of protection reaction include protection/deprotection of a ketone portion with a ketal portion and protect/deprotection of a ketone portion with a heteroatom analogue, such as thioketal, in the ketal portion. Such processes are described in Chapter 4 of Protective Groups in Organic Synthesis. Furthermore, they also include protect/deprotection between a sulfonic acid and a soluble ester derivative and protect/deprotection by introducing a t-butyl group as a soluble group into an aromatic ring and then removing the t-butyl group with an acid. However, the invention is not limited to these, and others can also be used preferably as long as they work as protective groups. When it is intended to improve the solubility in common solvents, the use of aliphatic groups, particularly those containing a ring portion, is preferred as protective groups because of their large steric hindrance.

From the viewpoint of reactivity and stability, more preferable examples of protection reaction include protection/deprotection of a ketone portion with a ketal portion and protect/deprotection of a ketone portion with a heteroatom analogue, such as thioketal, in the ketal portion. For the polymer electrolyte materials and polymer electrolyte membranes of the present invention, it is preferable to use a protective group-containing constituent unit that contains at least a portion as represented by either the general formula (U1) or (U2) given below.

[Chemical formula 29]

(U1)

(U2)

(In formulae (U1) and (U2), $Ar_9$ to $AR_{12}$ are each an arbitrarily selected divalent arylene group; $R_1$ and $R_2$ are each at least one group selected from H and alkyl groups; $R_3$ is an arbitrarily selected alkylene group; E is either O or S; and each of them may represent a plurality of groups. The groups represented by the formulae (U1) and (U2) may be substituted arbitrarily. Here, * indicates bonding sites to constituent units as represented by either the general formula (U1) or (U2) or to other constituent units.)

In particular, from the viewpoint of the odors, reactivity, and stability of the compounds, it is most preferable that E in the general formulae (U1) and (U2) be O, that is, the ketone portions be protected/deprotected with ketal portions.

In the general formula (U1), $R_1$ and $R_2$ are preferably an alkyl group, more preferably an alkyl group with a carbon number of 1 to 6, and most preferably an alkyl group with a carbon number of 1 to 3, from the viewpoint of stability. In the general formula (U2), $R_3$ is preferably an alkylene group with a carbon number of 1 to 7, that is a group as represented by $C_{n1}H_{2n1}$ (n1 is an integer of 1 to 7), and most preferably an alkylene group with a carbon number of 1 to 4, from the viewpoint of stability. Specific examples of $R_3$ include, but not limited to, —$CH_2CH_2$—, —$CH(CH_3)CH_2$—, —CH($CH_3$)CH($CH_3$)—, —C($CH_3$)$_2$CH$_2$—, —C($CH_3$)$_2$CH($CH_3$)—, —C($CH_3$)$_2$—O—($CH_3$)$_2$—, —$CH_2CH_2CH_2$—, and —$CH_2C(CH_3)_2CH_2$—. From the viewpoint of stability and the easiness of synthesis, $R_3$ is most preferably at least one selected from —$CH_2CH_2$—, —$CH(CH_3)CH_2$—, and —$CH_2CH_2CH_2$—.

Of the constituent units represented by the general formula (U1) or (U2), those including at least a potion as represented by the general formula (U2) are more preferable from the viewpoint of stability properties such as hydrolysis resistance.

Preferable organic groups as $Ar_9$ to $AR_{12}$ in the general formulae (U1) and (U2) include phenylene groups, naphthylene group, and biphenylene groups. These may be substituted arbitrarily. For the block copolymers according to the present invention, it is more preferable for both $AR_{11}$ and $AR_{12}$ in the general formula (U2) to be a phenylene group, and most preferable for both $AR_{11}$ and $AR_{12}$ to be a p-phenylene group from the viewpoint of solubility and availability of materials.

For the present invention, methods for protecting a ketone portion with a ketal include reacting a precursor compound containing a ketone group with a monofunctional and/or bifunctional alcohol in the presence of an acid catalyst. For example, 4,4'-dihydroxy benzophenone used as ketone precursor is reacted with a monofunctional and/or bifunctional alcohol in a solvent such as an aliphatic or aromatic hydrocarbon in the presence of an acid catalyst such as hydrogen bromide. The above alcohol is an aliphatic alcohol with a carbon number of 1 to 20. The improvement method for producing a ketal monomer to be used for the present invention is by reacting 4,4'-dihydroxy benzophenone used as ketone precursor with a bifunctional alcohol in the presence of an alkyl ortho ester and a solid catalyst.

For the present invention, there are no specific limitations on the method to be used for deprotecting at least part of the ketal-protected ketone portions to restore the original ketone portions. The aforementioned deprotection reaction can be carried out in the presence of water and an acid under non-uniform or uniform conditions, but from the viewpoint of mechanical strength, physical durability, and solvent resistance, it is preferable to mold the material into a film etc. and subsequently subjecting it to acid treatment. Specifically, deprotection can be carried out by immersing a molded film in a hydrochloric acid aqueous solution or sulfuric acid aqueous solution, and the concentration of the acid and the temperature of the aqueous solution may be set appropriately.

The required weight ratio of the acid aqueous solution to the polymer is preferably 1 to 100, but a larger quantity of water may be used additionally. The concentration of the acid catalyst in water is preferably 0.1 to 50 wt %. Preferred acid catalysts include strong mineral acids (strong inorganic acids) such as hydrochloric acid, nitric acid, fluorosulfonic acid, and sulfuric acid and strong organic acids such as p-toluene sulfonic acid and trifluoromethane sulfonic acid. The quantities of the acid catalyst and excess water, reaction pressure, etc. may be set appropriately depending on the film thickness etc. of the polymer.

For a film with a thickness of 25 μm, for example, complete deprotection can be easily achieved by immersion in an acidic aqueous solution such as 6N hydrochloric acid aqueous solution and 5 wt % sulfuric acid aqueous solution and heating at room temperature to 95° C. for 1 to 48 hours. Also, substantially all protective groups can be removed by immersion in 1N hydrochloric acid aqueous solution at 25° C. for 24 hours. However, the deprotection conditions are not limited to these, and deprotection may be performed by using an acidic gas, organic acid, or heat treatment.

Specifically, a precursor of a block copolymer containing a constituent unit as represented by the general formula (U1) or (U2) can be synthesized by, for example, an aromatic nucleophilic substitution reaction of a compound as represented by the general formula (U1-1) or (U2-1) given below, used as divalent phenol compound, with an aromatic active dihalide compound. The constituent unit represented by the general formula (U1) or (U2) may originate from either a divalent phenol compound or an aromatic active dihalide compound, but in view of the reactivity of monomers, it is preferable they originate from a divalent phenol compound.

[Chemical formula 30]

(U1-1)

(U2-1)

(In the general formulae (U1-1) and (U2-1), $Ar_9$ to $AR_{12}$ are each an arbitrarily selected divalent arylene group; $R_1$ and $R_2$ are each at least one group selected from H and alkyl groups; $R_3$ is an arbitrarily selected alkylene group; and E is either O or S. The compounds represented by the general formula (U1-1) or the general formula (U2-1) may be substituted arbitrarily.

Specific examples of particularly preferred divalent phenol compounds used for the present invention include compounds as represented by any of the aforementioned general formulae (r1) to (r10) and derivatives of these divalent phenol compounds. Of these divalent phenol compounds, those compounds as represented by any of the general formulae (r4) to (r10) are more preferable; those as represented by any of the general formula (r4), (r5), and (r9) are still more preferable; and those as represented by any of the general formula (r4) are the most preferable.

In the oligomer synthesis through an aromatic nucleophilic substitution reaction to produce a segment used for the present invention, a mixture of monomers as given above is reacted in the presence of a basic compound to form a polymer. The polymerization can be carried out in the temperature range of 0 to 350° C., but it is more preferably carried out at a temperature of 50 to 250° C. The reaction tends not to progress sufficiently if the temperature is lower than 0° C., while polymer decomposition tends to begin if it is higher than 350° C. The reaction can be carried out under solvent-free conditions, but preferably carried out in a solvent. Usable solvents include, but not limited to, aprotic polar solvents such as N,N-dimethyl acetamide, N,N-dimethyl formamide, N-methyl-2-pyrolidone, dimethyl sulfoxide, sulfolane, 1,3-dimethyl-2-imidazolidinone, and hexamethyl phosphonate triamide, but others that serve as stable solvents in an aromatic nucleophilic substitution reaction will also be usable. These organic solvents can be used singly or as a mixtures of a plurality thereof.

Usable basic compounds include, but not limited to, sodium hydroxide, potassium hydroxide, sodium carbonate, potassium carbonate, sodium hydrogen carbonate, and potassium hydrogen carbonate, but others that serve to convert aromatic diols into active phenoxide structures may also be usable. It is also preferable to add a crown ether such as 18-crown-6 to increase the nucleophilicity of phenoxides. These crown ethers are preferred because they can coordinate with a sodium ion or potassium ion in a sulfonic acid group, serving to improve the solubility in an organic solvent.

In an aromatic nucleophilic substitution reaction, water may result as a by-product. In that case, toluene etc. may be added to the reaction system to allow water to be removed as azeotrope out of the system, regardless of the polymerization solvent used. Other methods to remove water out of the system include the use of a water absorption agent such as molecular sieves.

Generally, azeotropic agents used to remove the reaction water or water introduced during the reaction are arbitrarily selected inactive compounds that substantially do not interfere with the polymerization, can be codistilled with water, and come to a boil in the range of about 25° C. to about 250° C. Common azeotropic agents include benzene, toluene, xylene, chlorobenzene, methylene chloride, dichlorobenzene, trichlorobenzene, and cyclohexane. Needless to say, it will be advantageous to adopt an azeotropic agent having a boiling point that is lower than the boiling point of the dipolar solvent used. An azeotropic agent is commonly used, but it is not always necessary when a high reaction temperature, for example, 200° C. or more, is adopted, and particularly when an inert gas is continuously fed to the reaction mixture. In general, it is desirable to carry out the reaction in an oxygen-free inactive atmosphere.

When the aromatic nucleophilic substitution reaction is to be carried out in a solvent, the quantity of the monomers to be fed is preferably such that the resulting polymer will have a concentration of 3 to 50 wt %. If it is less than 5 wt %, the degree of polymerization tends not to increase adequately. If it is more than 50 wt %, on the other hand, the reaction system tends to become too viscous, making it difficult to perform the post-treatment of the reactants.

After the completion of the polymerization reaction, the solvent is removed by evaporation out of the reaction solution, and if necessary, the residual material is washed, thereby providing an intended polymer. The polymer can also be obtained by adding the reaction solution into a solvent in which the polymer is low in solubility while the inorganic salt by-product is high in solubility, thus allowing the inorganic salt to be removed while precipitating the polymer as solid, followed by collecting the precipitate by filtration. The polymer thus recovered is then dried after being washed in alcohol or other solvents if necessary. If the polymer obtained has a required molecular weight, the halide or phenoxide end groups may be reacted if necessary by introducing a phenoxide or halide end capping agent to form stable end groups.

Here, the chemical structure of a block copolymer according to the present invention can be determined by infrared ray absorption spectrum analysis of the S=O absorption at 1,030 to 1,045 cm$^{-1}$ and 1,160 to 1,190 cm$^{-1}$, C—O—C absorption at 1,130 to 1,250 cm$^{-1}$, and C=O absorption at 1,640 to 1,660 cm$^{-1}$, and the composition ratio can be determined by neutralization titration of the sulfonic acid groups and element analysis. The structure can also be determined from, for example, a 6.8 to 8.0 ppm aromatic proton peak in nuclear magnetic resonance spectra ($^1$H-NMR). Furthermore, the positions and arrangement of the sulfonic acid groups can be determined by solution $^{13}$C-NMR and solid state $^{13}$C-NMR.

Described next are concrete synthesis methods to produce a block copolymer that contains at least a ionic group-containing segment (A1), a ionic group-free segment (A2), and a linker portion connecting the segments. However, note that the present invention is not limited thereto.

A block copolymer according to the present invention can also be produced by synthesizing a precursor of a block copolymer and then removing at least part of the protective groups contained in the precursor.

Specific examples of production methods for a block copolymers according to the present invention and a precursor of the block copolymer include the following:
a. Reacting a dihalide linker with either a segment and/or segment precursor containing a constituent unit as represented by the formula (S1) in which both terminals are OM groups (M's are independently a hydrogen, a metal cation, or an ammonium cation, and this applies hereinafter unless otherwise specified) or a segment and/or segment precursor containing a constituent unit as represented by the formula (NP1) in which both terminals are OM groups, followed by copolymerizing alternately the remaining of the two segment s to produce a block copolymer,
b. Randomly polymerizing a segment and/or segment precursor containing a constituent unit as represented by the formula (S1) in which both terminals are OM groups, a segment and/or segment precursor containing a constituent unit as represented by the formula (NP1) in which both terminals are OM groups, and a dihalide linker to produce a block copolymer,
c. Producing a block copolymer from an unsulfonated segment and/or segment precursor containing a constituent unit as represented by the formula (S1) by method a or method b described above, and then introducing an ionic group selectively to the unsulfonated portions of the segment and/or segment precursor containing a constituent unit as represented by the formula (S1),
d. a combination of methods a to c described above. Of these, method a is the most preferable because alternating copolymerization serves to control the size of the phase-separated domains so that a chemically stable block copolymer can be produced.

Specifically, a production process for a block copolymer according to the present invention preferably includes at least steps (1) to (4) given below: A process containing these steps serves to improve the mechanical strength and durability as a result of an increased molecular weight, which, in combination with the alternating introduction of the two segments, makes it possible to produce a block copolymer having phase-separated structures with accurately controlled domain sizes and high proton conductivity under low humidify conditions.
(1) A step for synthesizing an ionic group-containing segment (A1) that contains a constituent unit as represented by the general formula (S1) and/or a constituent unit helpful as a precursor of a constituent unit as represented by the general formula (S1) and that has an OM group at both terminals,
(2) A step for synthesizing an ionic group-free segment (A2) that contains a constituent unit as represented by the general formula (NP1) and/or a constituent unit helpful as a precursor of a constituent unit as represented by the general formula (NP1) and that has an OM group at both terminals,
(3) A step for introducing a linker portion into each OM group at both terminals of the ionic group-containing segment (A1) or the ionic group-free segment (A2), and
(4) A step for producing a block copolymer and block copolymer precursor by connecting the linker portions at both terminals of the segment synthesized in step (3) to the OM groups at both terminals of the another segment.

For method a, specific examples of the segment represented by the formula (S1) having an OM group at both terminals and those of the segment represented by formula (NP1) having an OM group at both terminals respectively include those as represented by the formulae (H3-1) and (H3-2) given below, and specific examples of the segments reacted with a dihalide linker respectively include those as represented by the formulae (H3-3) and (H3-4) given below. However, note that the present invention is not limited to these examples.

[Chemical formula 31]

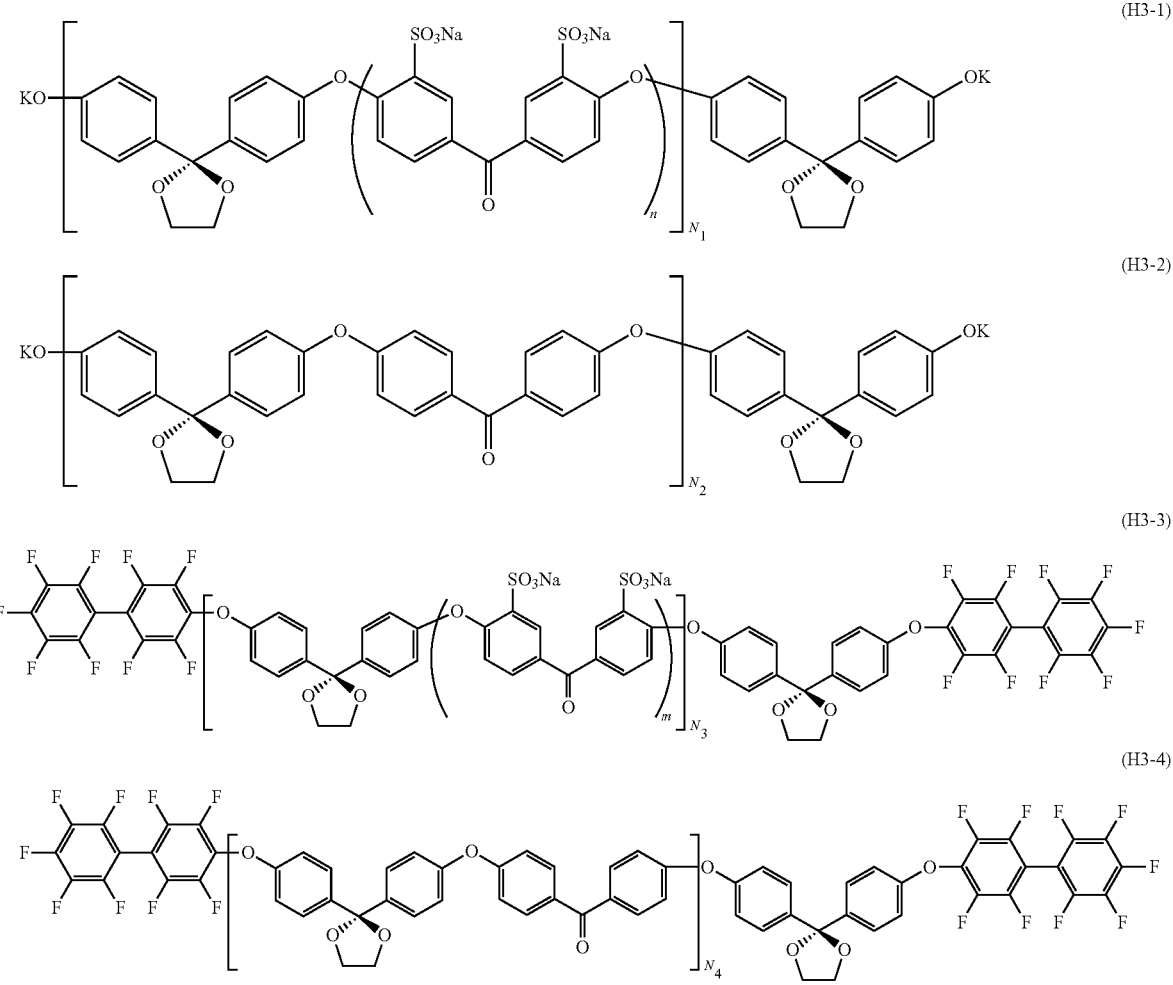

(In the formulae (H3-1) to (H3-4), n1, n2, n3, and n4 are independently an integer of 1 to 150, and m and n are independently an integer of 1 to 3.)

In the formula (H3-1) to (H3-4) given above, a halogen atom is denoted by F and an alkali metal is denoted by Na or K, but the invention is not limited to these. The above formulae are shown only to help the readers understand the invention and do not necessarily show correct examples of the chemical structures, composition, and arrangement of the polymerization units as well as the positions, numbers, and molecular weights of sulfonic acid groups, and the invention are not limited thereto.

In addition, a ketal group is introduced here as a protective group in all the segments represented by the formulae (H3-1) to (H3-4) given above, but for the present invention, what is necessary is to introduce a protective group into a component that is high in crystallizability and low in solubility. The ionic group-containing segments (A1) represented by the formulae (H3-1) and (H3-3) given above do not necessarily have a protective group, and from the viewpoint of durability and dimensional stability, those having no protective group may also be used preferably.

For the blocks represented by the formula (H3-1), oligomers having a controlled molecular weight can be synthesized by reacting a bisphenol component and an aromatic dihalide component at a ratio of $(N_1+1):N_1$. The same applies to the formula (H3-2) given above.

With respect to the reaction temperature for block copolymerization involving a linker, the reaction is carried out preferably under heat conditions of 140° C. or less. It is more preferably 80° C. or more and 120° C. or less. A reaction temperature maintained at 120° C. or less serves to adequately prevent the randomization of polymer structures from being caused by ether exchange during the reaction. If it is 80° C. or more, on the other hand, a polymer having a random molecular structure can be obtained.

The co-continuous phase-separated structure in a block copolymer according to the present invention can be observed by transmission electron microscopy. High proton conductivity under low humidify conditions can be realized by controlling the phase-separated structure in the block copolymer, that is, the state and shape of the aggregates of the ionic group-containing segment (A1) and the ionic group-free segment (A2). The phase-separated structure can be analyzed by transmission electron microscopy (TEM), atomic force microscopy (AFM), etc.

It is preferable for a block copolymer according to the present invention to have a phase-separated structure that is observable by TEM at a magnification of 50,000 and has an average interlayer distance or average interparticle distance of 8 nm or more and 100 nm or less as determined by image processing. In particular, the average interlayer distance or average interparticle distance is preferably 10 nm or more and 50 nm or less and most preferably 15 nm or more and 30 nm or less. If a phase-separated structure is not observed by transmission electron microscopy or if the average interlayer distance or average interparticle distance is less than 8 nm, the material is not preferable because of insufficient ion channel continuity or insufficient conductivity. An interlayer distance of more than 5,000 nm is not preferable because in that case, the mechanical strength and dimensional stability will not be sufficiently high.

The block copolymers according to the present invention are characterized by having a crystallizability while maintaining a phase-separated structure, and the crystallizability can be confirmed by differential scanning calorimetry (DSC) or wide angle X-ray diffraction. Specifically, the block copolymers have a heat of crystallization of 0.1 J/g or more as determined by differential scanning calorimetry and a degree of crystallizability of 0.5% or more as determined by wide angle X-ray diffraction.

For the present invention, a polymer "having crystallizability" has a nature of being able to be crystallized when the polymer is heated, or is already crystallized. On the other hand, an amorphous polymer is a non-crystallizable polymer, that is, a polymer in which crystallization substantially does not progress. Thus, even in a crystallizable polymer, an amorphous polymer state can occur if crystallization has not progressed sufficiently.

There are no specific limitations on the method to be used to process a polymer electrolyte material according to the present invention into a polymer electrolyte membrane, and usable methods include production of a film from a solution state or production of a film from a molten state while a protective group such as ketal is maintained. Examples of the former include, for example, dissolving the polymer electrolyte material in a solvent such as N-methyl-2-pyrolidone and flow-casting the solution on a glass plate etc., followed by removing the solvent to form a film.

Preferable solvents for such film production are those which can dissolve the polymer electrolyte material and can be removed subsequently, and they include, for example, aprotic polar solvents such as N,N-dimethyl acetamide, N,N-dimethyl formamide, N-methyl-2-pyrolidone, dimethyl sulfoxide, sulfolane, 1,3-dimethyl-2-imidazolidinone, and hexamethyl phosphonate triamide; ester based solvents such as γ-butyrolactone and butyl acetate; carbonate based solvents such as ethylene carbonate and propylene carbonate; alkylene glycol monoalkyl ethers such as ethylene glycol monomethyl ether, ethylene glycol monoethyl ether, propylene glycol monomethyl ether, and propylene glycol monoethyl ether; alcohol based solvents such as isopropanol; water; and mixtures thereof; of which aprotic polar solvents are the highest in solubility and therefore the most preferable. Furthermore, it is also preferable to add a crown ether such as 18-crown-6 in order to increase the solubility of an ionic group-containing segment (A1).

For the present invention, when a film is produced from a solution of a block copolymer, it is important to select an appropriate solvent for the phase-separated structure, and it is also preferable to use a mixture of an aprotic polar solvent and a low polarity solvent.

A preferable method to produce a tough film is to prepare a polymer solution having a required solid concentration and subjecting it to filtration under atmospheric pressure or compression filtration to remove foreign objects existing in the polymer electrolyte solution. There are no specific limitations on the filtering material to be used here, but preferred ones include glass filters and metal filters. In this filtration, the smallest pores through which the polymer solution passes preferably have a size of 1 μm or less. If filtration is not performed, foreign objects are allowed to remain, leading to the occurrence of film breakage or insufficient durability, and therefore, it is not preferable.

Subsequently, the resulting polymer electrolyte membrane is preferably subjected to heat treatment while maintaining at least part of the ionic group in the form of metal salts. The polymer electrolyte material to be used is obtained in the form a metal salt from its polymerization process, it is preferably subjected directly to film production and heat treatment. There are no specific limitations on the metal in the metal salt as long as it can form a salt with the sulfonic acid, but from the viewpoint of price and environment load, preferable metals include Li, Na, K, Rb, Cs, Mg, Ca, Sr, Ba, Ti, V, Mn, Fe, Co, Ni, Cu, Zn, Zr, Mo, and W, of which Li, Na, K, Ca, Sr, and Ba more preferable, of which Li, Na, and K still more preferable.

This heat treatment is preferably performed at a temperature of 80 to 350° C., more preferably 100 to 200° C., and particularly preferably 120 to 150° C. The heat treatment period of preferably 10 seconds to 12 hours, more preferably 30 seconds to 6 hours, and particularly preferably 1 minute to 1 hour. An excessively low heat treatment temperature can possibly lead to insufficient mechanical strength and physical durability. If it is too high, on the other hand, chemical decompose can possibly progress in the film material. A heat treatment period of less than 10 seconds will lead to insufficient effect of the heat treatment. If is more than 12 hours, on the other hand, the film material will degrade easily. The polymer electrolyte membrane resulting from the heat treatment may be immersed in an acidic aqueous solution as required for proton substitution. The polymer electrolyte membrane according to the present invention produced by this process can have both proton conductivity and physical durability in a good balance.

To convert the polymer electrolyte material used for the present invention into a film, a film may be produce from the polymer electrolyte material by the process described above, followed by deprotecting at least part of the ketal-protect ketone portions into the original ketone portions. This method makes it possible to produce a film from a solution state of a block copolymer containing a block free of low-solubility ionic groups, leading to high proton conductivity, high mechanical strength, and high physical durability maintained simultaneously.

The polymer electrolyte membrane according to the present invention is preferably has a film thickness of 1 to 2,000 μm for effective use. The thickness is preferably more than 1 μm to ensure adequate mechanical strength and physical durability for practical use, and it is preferably less than 2,000 μm to decrease the film resistance, i.e., improve the power generation performance. The film thickness is more preferably in the range of 3 to 50 μm and particularly preferably in the range of 10 to 30 μm. This film thickness can be controlled by appropriately changing the solution concentration and coating thickness on the substrate.

The polymer electrolyte membrane produced according to the present invention may contain additives that are used for ordinary polymer compounds, including crystal nucleating agent, plasticizer, stabilizer, antioxidant, or mold releasing agent to an extent that does not impair the objectives of the present invention.

In addition, the polymer electrolyte membrane produced according to the present invention may also contain various polymers, elastomers, fillers, fine particles, and other various additives with the aim of improving the mechanical strength, heat stability, and processability, to an extent that will not have adverse influence on the above characteristics. Furthermore, it may be reinforced by a microporous film, nonwoven fabric, mesh, etc.

When using this polymer electrolyte membrane for producing a fuel cell, there are no specific limitations on the method to be adopted to join the polymer electrolyte membrane to an electrode, and generally known methods such as the chemical plating process described in J. Electrochem. Soc., 1985, 53, p. 269, and the heat press bonding process for gas diffusion electrodes described in Electrochemical Science and Technology, 1988, 135, 9, p. 2209 can be applied.

When using a hot press for jointing, an appropriate temperature and pressure may be adopted depending on the thickness of the electrolyte membrane, its moisture content, catalyst layer, and electrode base material. For the present invention, composite production by using a press is possible regardless of whether the electrolyte membrane is in a dried state or contains water. Specific pressing methods include the use of a roll press under specified pressure and clearance conditions and a flat plate press under specified pressure conditions, and they are preferably performed in the range of 0° C. to 250° C. from the viewpoint of industrial productivity and prevention of heat decomposition of polymer materials with ionic groups. From the viewpoint of protection of the electrolyte membrane and electrode, the pressing force is preferably as small as possible, and when using a flat plate press, it is preferably 10 MPa or less. From the viewpoint of preventing a short circuit between the anode and cathode electrodes, it is also a preferable option to simply stacking electrodes and electrolyte membrane to form a fuel cell instead of performing a hot pressing step to form a composite. A fuel cell produced by this process will have a higher fuel cell durability because this structure tends to depress the electrolyte membrane degradation inferred to be attributable to short circuiting taking place as power generation is performed repeatedly.

There are also no specific limitations on the uses of polymer electrolyte fuel cells produced from the polymer electrolyte material and polymer electrolyte membrane according to the present invention, but preferable applications include electric power supply sources for movable devices. In particular, they can be used favorably as electric power supply sources for portable appliances such as portable telephones, personal computers, PDAs, TVs, radios, music players, game consoles, head sets, and DVD players; various humanoid type or animal Type robots for industrial applications; home electric appliances such as cordless cleaners; toys; vehicles such as, power-assisted bicycles, motorcycles, automobiles, buses, and trucks; and movable bodies such as ships and railroad cars; as well as alternatives to conventional primary and secondary batteries such as stationary type power generators and hybrid power sources therewith.

EXAMPLES

The present invention will now be illustrated in more detail with reference to Examples, but it should be understood that the invention is not construed as being limited thereto. The various characteristics described below were measured under the following conditions.
(1) Ion Exchange Capacity
Neutralization titration was performed to determine the ion exchange capacity (meq/g) per gram.
(2) Degree of Proton Conductivity
A film-like specimen was immersed in pure water at 25° C. for 24 hours, then kept in constant temperature and humidity baths at a temperature of 80° C. and a relative humidity of 25 to 95% for 30 minutes in each step, and subjected to measurement of the degree of proton conductivity by the constant-potential alternating current impedance method.

The measuring equipment used was an electrochemical measuring system manufactured by Solartron (Solartron 1287 Electrochemical Interface, and Solartron 1255B Frequency Response Analyzer), and the degree of proton conductivity was calculated from constant-potential alternating current impedance measurements made by the two-terminal method. The alternating current amplitude was 50 mV. The specimens used were in the shape of film with a width of 10 mm and a length of 50 mm. The measure jigs were produced of phenol resin, and the measuring portion was kept in an open state. Two platinum plates (with a thickness of 100 μm) were used as electrodes. A specimen was placed between the electrodes which were disposed parallel to each other with a distance of 10 mm between them and perpendicular to the length direction of the specimen.
(3) Number Average Molecular Weight and Weight Average Molecular Weight The number average molecular weight and weight average molecular weight of polymer specimens was measured by GPC. A built-in type apparatus containing an ultraviolet detector and differential refractometer (HLC-8022GPC, manufactured by Tosoh Corporation) and two GPC columns (inside diameter of 6.0 mm and length of 15 cm, TSK Gel SuperHM-H, manufactured by Tosoh Corporation) were used with an N-methyl-2-pyrolidone solvent (N-methyl-2-pyrolidone solvent containing 10 mmol/L of lithium bromide)

under the measuring conditions of a sample concentration of 0.1 wt %, flow rate of 0.2 mL/min, and temperature of 40° C., and the standard polystyrene equivalent number average molecular weight and weight average molecular weight were determined.

(4) Film Thickness

An ID-C112 apparatus manufactured by Mitutoyo Corporation mounted to a BSG-20 granite comparator stand manufactured by Mitutoyo Corporation was used for measurement.

(5) Observation of Phase-Separated Structure by Transmission Electron Microscopy (TEM)

A specimen was immersed in a 2 wt % lead acetate aqueous solution, used as dyeing agent, and left to stand at 25° C. for 24 hours. The dyed specimen was taken out, embedded in visible light curable resin, and irradiated with visible light for 30 seconds for fixation.

A thin specimen of 100 nm was cut out using an ultramicrotome at room temperature, and the resulting thin specimen was put on a Cu grid and subjected to TEM observation. Observations were made at an accelerating voltage of 100 kV, and photographs were taken at magnifications of ×8,000, ×20,000, and ×100,000. The equipment used was TEM H7100FA (manufactured by Hitachi, Ltd.).

(6) Purity Analysis of Bisphenol Compounds

Quantitative analysis was carried out by gas chromatography (GC) under the conditions given below.
Column. DB-5 (manufactured by J&W) length=30 m, diameter=0.53 mm, depth=1.50 μm
Carrier: helium (linear speed=35.0 cm/sec)
Analysis conditions
Inj. temp.=300° C.
Detct. temp.=320° C.
Oven=50° C. for 1 min
Rate=10° C./min
Final=300° C. for 15 min
SP ratio=50:1

(7) Hot Water Resistance

The hot water resistance of an electrolyte membrane was evaluated based on measurements of its dimensional change rate in hot water at 95° C. A strip with a length of about 5 cm and a width of about 1 cm was cut out of an electrolyte membrane, immersed in water at 25° C. for 24 hours, and then subjected to measurement of length (L1) with a caliper square. The electrolyte membrane was immersed in hot water at 95° C. for 8 hours, and subjected again to measurement of length (L2), followed by visually observing the dimensional change rate.

(8) Nuclear Magnetic Resonance (NMR) Spectrum

The structure was analyzed by $^1$H-NMR under the following measuring conditions to determine the molar fractions of the ionic group-containing segment (A1) and the ionic group-free segment (A2). The molar fractions were calculated from the integral areas of the peaks at 8.2 ppm (originating from disulfonate-4,4'-difluorobenzophenone) and 6.5 to 8.0 ppm (originating from all aromatic protons other than disulfonate-4,4'-difluorobenzophenone).
Equipment: EX-270 manufactured by JEOL Ltd.
Resonance frequency: 270 MHz ($^1$H-NMR)
Measuring temperature: room temperature
Solvent for dissolution: DMSO-d6
Internal reference substance: TMS (0 ppm)
Cumulative number of times of measurement: 16

Solid $^{13}$C-CP/MAS spectrum measurements were made under the following measuring conditions to determine if ketal groups exist.
Equipment: CMX-300 Infinity manufactured by Chemagnetic
Measuring temperature: room temperature
Internal reference substance: Si rubber (1.56 ppm)
Measured nucleus: 75.188829 MHz
Pulse width: 90° pulse, 4.5 nsec
Pulse repeating time: ACQTM=0.03413 sec, PD=9 sec
Spectrum width: 30.003 kHz
Specimen rotation: 7 kHz
Contact time: 4 msec (9) Chemical Stability The chemical stability of an electrolyte membrane was evaluated based on results of immersion of a specimen of about 10 mg in a large excess of a 0.05 wt % hydrogen peroxide solution at 80° C. Its weight average molecular weight was measured before and 100 hours after the immersion to calculate the molecular weight retention rate.

Synthesis Example 1

Synthesis of 2,2-bis(4-hydroxyphenyl)-1,3-dioxolane (K-DHBP) which is Represented by the General Formula (G1) Given Below

[Chemical formula 32]

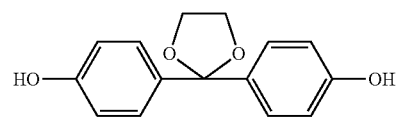

(G1)

In a 500 mL flask equipped with a stirrer, thermometer, and distillation tube, 49.5 g of 4,4'-dihydroxy benzophenone, 134 g of ethylene glycol, 96.9 g of trimethyl orthoformate, and 0.50 g of p-toluene sulfonic acid monohydrate were fed and dissolved. Then, the solution was maintained at 78 to 82° C. for 2 hours under continued stirring. Furthermore, the inner temperature was gradually raised up to 120° C., and heating was continued until the distillation of methyl formate, methanol, and trimethyl orthoformate stopped completely. The reaction solution was cooled to room temperature and diluted with ethyl acetate, and the organic layer was washed with 100 mL of a 5% potassium carbonate aqueous solution and separated, followed by evaporating the solvent. To the residual material, 80 mL of dichloromethane was added to precipitate a crystalline material, which was separated by filtration and dried to obtain 52.0 g of 2,2-bis(4-hydroxyphenyl)-1,3-dioxolane. The crystal material was subjected to GC analysis and found to contain 99.8% of 2,2-bis(4-hydroxyphenyl)-1,3-dioxolane and 0.2% of 4,4'-dihydroxy benzophenone.

Synthesis Example 2

Synthesis of disodium-3,3'-disulfonate-4,4'-difluoro benzophenone which is Represented by the General Formula (G2) Given Below

[Chemical formula 33]

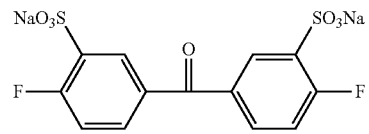

(G2)

First, 109.1 g of 4,4'-difluoro benzophenone (reagent manufactured by Aldrich) was reacted in 150 mL of fuming sulfuric acid (50% $SO_3$) (reagent manufactured by Wako Pure Chemical Industries, Ltd.) at 100° C. for 10 hours. Subsequently, the solution was added little by little to a large amount of water and neutralized with NaOH, and 200 g of sodium chloride was added to precipitate the synthesized material. The resulting precipitate was separated by filtration, and recrystallized with ethanol aqueous solution to obtain disodium-3,3'-disulfonate-4,4'-difluorobenzophenone, which is represented by the general formula (G2). It had a purity of 99.3%. Its structure was confirmed by $^1$H-NMR. The quantities of impurities were analyzed by capillary electrophoresis (for organic substances) and ion chromatography (for inorganic substances).

Example 1

Synthesis of an Aromatic Sulfonic Acid Derivative as Represented by the Formula (G3) Given Below of 4-fluorobenzoyl chloride was dropped at 0° C., followed by gradual heating to room temperature and reaction for 4 hours. The solution was diluted with dichloromethane and washed with water, methanol, and hexane to obtain 350 g of a difluoro compound. Then, 350 g of the resulting difluoro compound was reacted in 1,130 g fuming sulfuric acid (30% $SO_3$) (reagent manufactured by Wako Pure Chemical Industries, Ltd.) at 115° C. for 20 hours. The solution was added little by little to a large amount of water and neutralized with NaOH, followed by precipitating sodium sulfate with ethanol three times to remove it, thereby obtaining an aromatic sulfonic acid derivative as represented by the formula (G3) given above. Its structure was confirmed by $^1$H-NMR.

[Chemical formula 34]

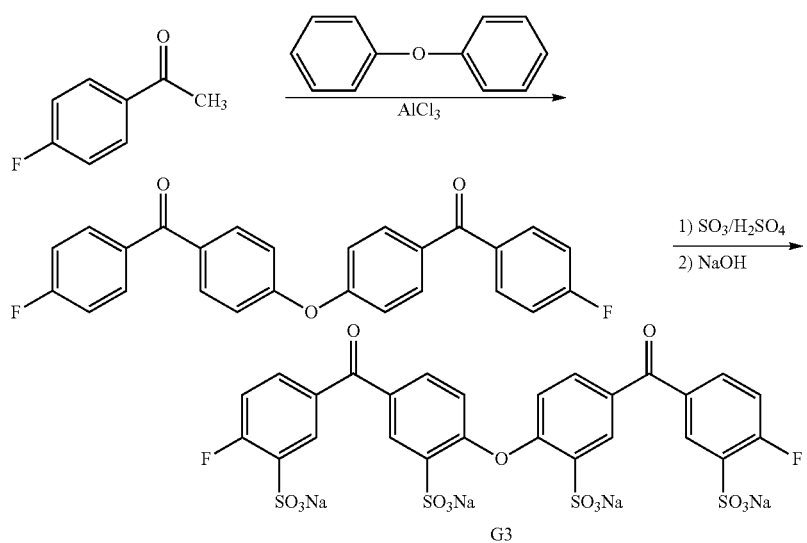

First, 160 g diphenyl ether (reagent manufactured by Tokyo Chemical Industry Co., Ltd.) and 317 g of aluminum chloride were dissolved in 800 mL of dichloromethane, and then a dichloromethane solution (200 mL) containing 358 g Example 2

Synthesis of an Aromatic Sulfonic Acid Derivative as Represented by the Formula (G4) Given Below

[Chemical formula 35]

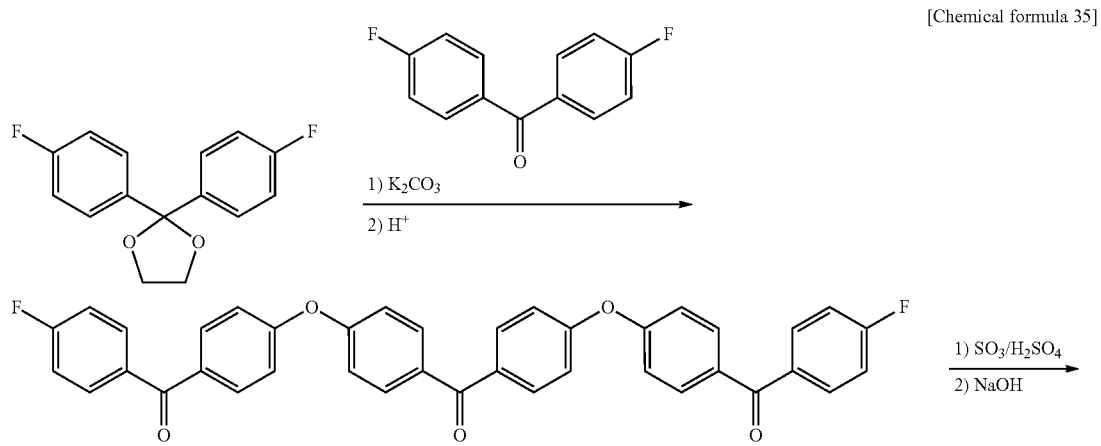

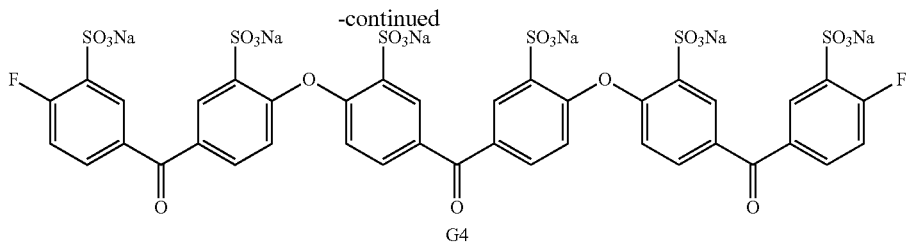

In a flask equipped with a stirrer, thermometer, and distillation tube, 148 g of 4-fluoro-4'-hydroxybenzophenone, 400 g of ethylene glycol, 286 g of trimethyl orthoformate, and 1.5 g of p-toluene sulfonic acid monohydrate were fed and dissolved. Then, the solution was maintained at 80° C. for 2 hours under continued stirring. Furthermore, the inner temperature was gradually raised up to 120° C., and heating was continued until the distillation of methyl formate, methanol, and trimethyl orthoformate stopped completely. The reaction solution was cooled to room temperature and diluted with ethyl acetate, and the organic layer was washed with 100 mL of a 5% potassium carbonate aqueous solution and separated, followed by evaporating the solvent. To the residual material, 80 mL of dichloromethane was added to precipitate a crystalline material, which was separated by filtration and dried to obtain 150 g of 2-(4-hydroxyphenyl)-2-(4-fluorophenyl)-1,3-dioxolane.

To a three-neck flask equipped with a stirrer, nitrogen supply tube, and Dean-Stark trap, 26.6 g of potassium carbonate (reagent manufactured by Aldrich), 40 g of the 2-(4-hydroxyphenyl)-2-(4-fluorophenyl)-1,3-dioxolane synthesized above, and 16 g of 4,4'-difluorobenzophenone (reagent manufactured by Aldrich) were fed, followed by nitrogen purge, dehydration in 150 mL of N,N-dimethyl acetamide (DMAc) and 80 mL of toluene at 150° C., heating to remove toluene, and reaction at 165° C. for 2 hours. The resulting material was deprotected by separation and extraction with chloroform/diluted hydrochloric acid, washed with methanol, and dried to obtain a difluoro compound.

Then, 50 g of the resulting difluoro compound was reacted in 138 g of fuming sulfuric acid (30% SO₃) (reagent manufactured by Wako Pure Chemical Industries, Ltd.) at 115° C. for 20 hours. The solution was added little by little to a large amount of water and neutralized with NaOH, followed by precipitating sodium sulfate with ethanol three times to remove it, thereby obtaining an aromatic sulfonic acid derivative as represented by the formula (G4) given above. Its structure was confirmed by $^1$H-NMR.

Example 3

Synthesis of an Aromatic Sulfonic Acid Derivative as Represented by the Formula (G5) Given Below

[Chemical formula 36]

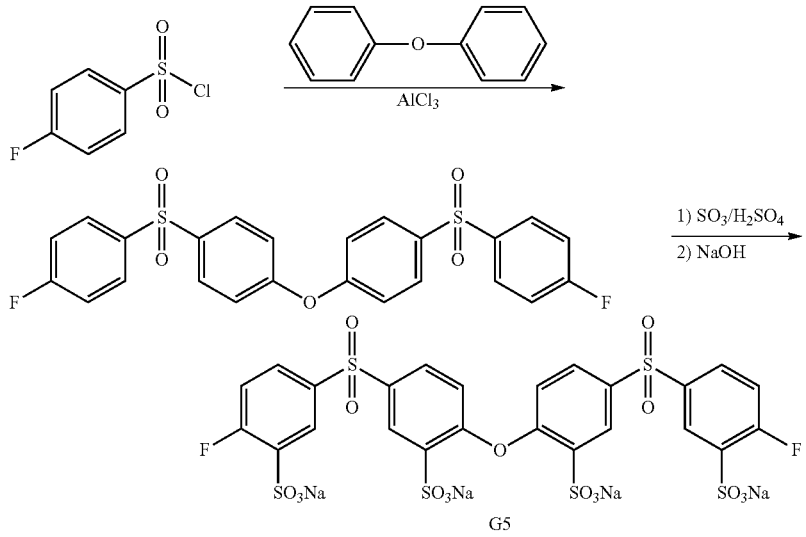

First, 160 g of diphenyl ether (reagent manufactured by Tokyo Chemical Industry Co., Ltd.) and 317 g of aluminum chloride were dissolved in 800 mL of dichloromethane, and then a dichloromethane solution (200 mL) containing 439 g of 4-fluorobenzenesulfonyl chloride was dropped at 0° C., followed by gradual heating to room temperature and reaction for 4 hours. The solution was diluted with dichloromethane and washed with water, methanol, and hexane to obtain 410 g of a difluoro compound. Then, 410 g of the resulting difluoro compound was reacted in 1,130 g of fuming sulfuric acid (30% SO₃) (reagent manufactured by Wako Pure Chemical Industries, Ltd.) at 115° C. for 20 hours. The solution was added little by little to a large amount of water and neutralized with NaOH, followed by precipitating sodium sulfate with ethanol three times to remove it, thereby obtaining an aromatic sulfonic acid derivative as represented by the formula (G5) given above. Its structure was confirmed by $^1$H-NMR.

Example 4

Synthesis of an Aromatic Sulfonic Acid Derivative as Represented by the Formula (G6) Given Below

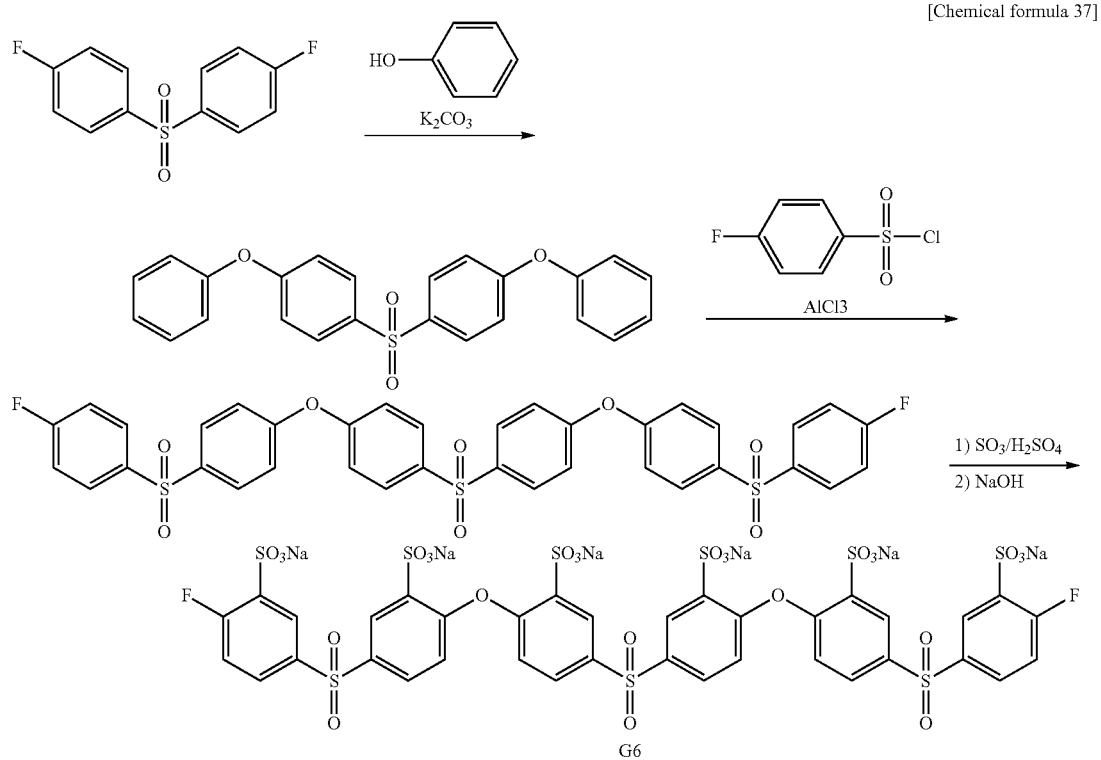

[Chemical formula 37]

To a three-neck flask equipped with a stirrer, nitrogen supply tube, and Dean-Stark trap, 228 g of potassium carbonate (reagent manufactured by Aldrich), 200 g of 4,4'-difluorodiphenyl sulfone, and 155 g of phenol were fed, followed by nitrogen purge, dehydration in 500 mL of N,N-dimethyl acetamide (DMAc) and 200 mL of toluene at 150° C., heating to remove toluene, and reaction at 165° C. for 2 hours. The resulting material was separated and extracted with chloroform/water, washed with methanol, and dried to obtain 221 g of a tetraphenyl compound.

First, 221 g of the resulting tetraphenyl compound and 227 g of aluminum chloride were dissolved in 570 mL of dichloromethane, and then a dichloromethane solution (100 mL) containing 224 g of 4-fluorobenzenesulfonyl chloride was dropped at 0° C., followed by gradual heating to room temperature and reaction for 4 hours. The solution was diluted with dichloromethane and washed with water, methanol, and hexane to obtain 268 g of a difluoro compound. Then, 268 g of the resulting difluoro compound was reacted in 740 g of fuming sulfuric acid (30% $SO_3$) (reagent manufactured by Wako Pure Chemical Industries, Ltd.) at 115° C. for 20 hours. The solution was added little by little to a large amount of water and neutralized with NaOH, followed by precipitating sodium sulfate with ethanol three times to remove it, thereby obtaining an aromatic sulfonic acid derivative as represented by the formula (G6) given above. Its structure was confirmed by $^1$H-NMR.

Example 5

Sulfonic Acid Group-Containing Polymer as Represented by the General Formula (G7) Given Below

[Chemical formula 28]

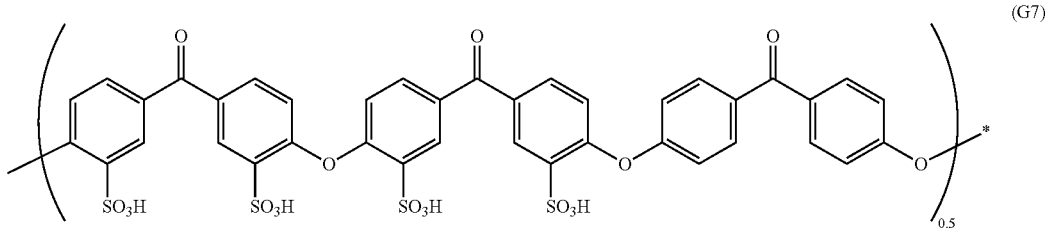

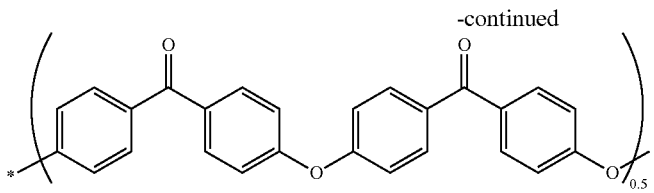

(In the general formula, * represents the position where the upper part of the general formula and the lower part of the general formula are bonded to each other.)

To a 500 mL three-neck flask equipped with a stirrer, nitrogen supply tube, and Dean-Stark trap, 5.5 g of potassium carbonate, 5.2 g of the 2,2-bis(4-hydroxyphenyl)-1,3-dioxane mixture obtained in Synthesis example 1, 2.2 g of 4,4'-difluorobenzophenone, 8.4 g of the aromatic sulfonic acid derivative represented by the formula (G3) obtained in Example 1, and 2.6 g of 18-crown-6-ether were fed, followed by dehydration with 50 mL of N-methylpyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 310,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G7) given above. The resulting film had a sulfonic acid group density of 3.0 meq/g.

The resulting film had a film thickness of 25 μm, a high degree of proton conductivity of 310 mS/cm at 80° C. and a relative humidity of 85%, and an excellent dimensional stability in hot water. Furthermore, NMR analysis showed the absence of ketal groups.

Example 6

Sulfonic Acid Group-Containing Polymer as Represented by the General Formula (G8) Given Below

[Chemical formula 39]

(In the general formula, * represents the position where the upper part of the general formula and the lower part of the general formula are bonded to each other.)

To a 500 mL three-neck flask equipped with a stirrer, nitrogen supply tube, and Dean-Stark trap, 4.4 g of potassium carbonate, 5.2 g of the 2,2-bis(4-hydroxyphenyl)-1,3-dioxane mixture obtained in Synthesis example 1, 3.1 g of 4,4'-difluorobenzophenone, 5.0 g of the aromatic sulfonic acid derivative represented by the formula (G3) given above obtained in Example 1, and 1.6 g of 18-crown-6-ether were fed, followed by dehydration with 50 mL of N-methyl pyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 330,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G8) given above. The resulting film had a sulfonic acid group density of 2.2 meq/g.

The resulting film had a film thickness of 25 μm, a high degree of proton conductivity of 220 mS/cm at 80° C. and a relative humidity of 85%, and an excellent dimensional stability in hot water. Furthermore, NMR analysis showed the absence of ketal groups.

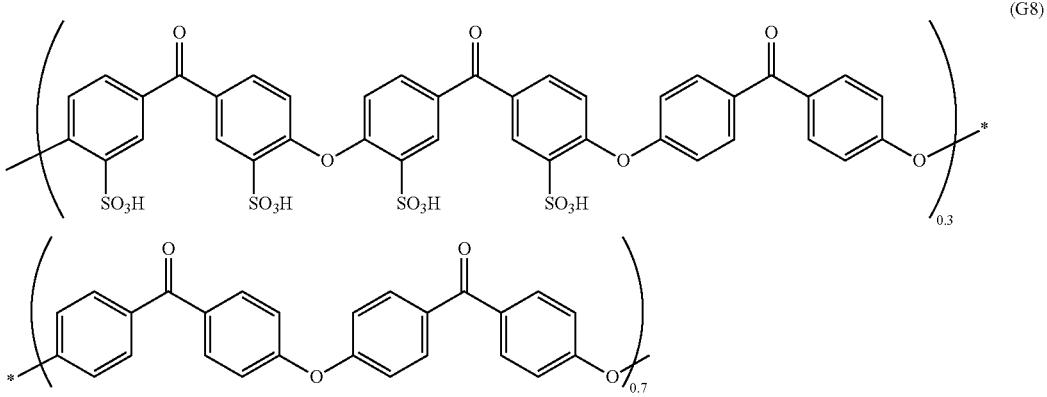

Example 7

Sulfonic Acid Group-Containing Polymer as Represented by the General Formula (G9) Given Below

[Chemical formula 40]

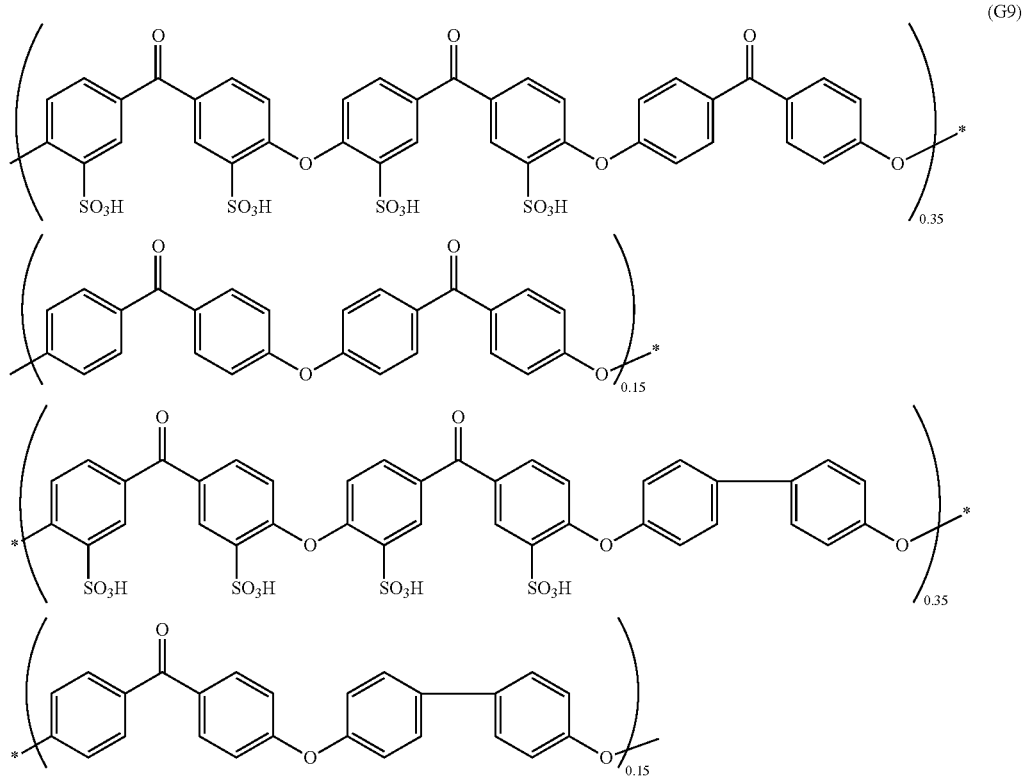

(In the general formula, * represents the position where the upper part of the general formula and the lower part of the general formula are bonded to each other.)

To a 500 mL three-neck flask equipped with a stirrer, nitrogen supply tube, and Dean-Stark trap, 6.6 g of potassium carbonate, 2.6 g of the 2,2-bis(4-hydroxyphenyl)-1,3-dioxane mixture obtained in Synthesis example 1, 1.9 g of 4,4'-biphenol, 1.3 g of 4,4'-difluorobenzophenone, 11.7 g of the aromatic sulfonic acid derivative represented by the formula (G3) given above obtained in Example 1, and 3.7 g of 18-crown-6-ether were fed, followed by dehydration with 50 mL of N-methylpyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 290,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G9) given above. The resulting film had a high sulfonic acid group density of 3.7 meq/g.

The resulting film had a film thickness of 27 μm and a very high degree of proton conductivity of 400 mS/cm at 80° C. and a relative humidity of 85%. Furthermore, NMR analysis showed the absence of ketal groups.

Example 8

[Chemical formula 41]

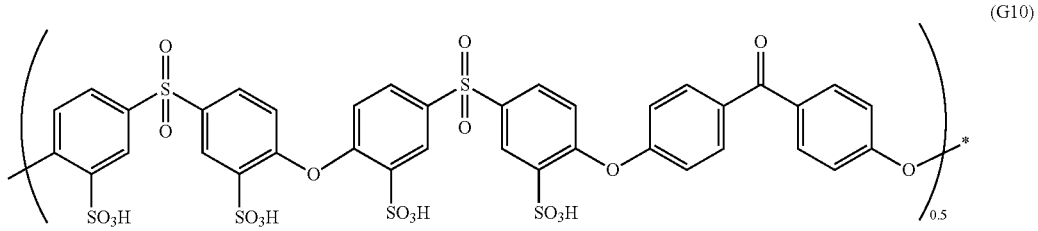

-continued

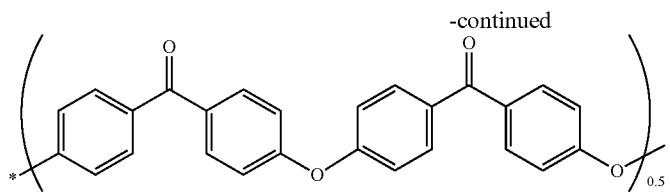

Except that 9.1 g of the aromatic sulfonic acid derivative obtained in Example 3 was used instead of the aromatic sulfonic acid derivative obtained in Example 1, the same polymerization procedure as in Example 5 was carried out to produce a ketal-containing precursor polymer. It had a weight average molecular weight of 320,000.

[Chemical formula 42]

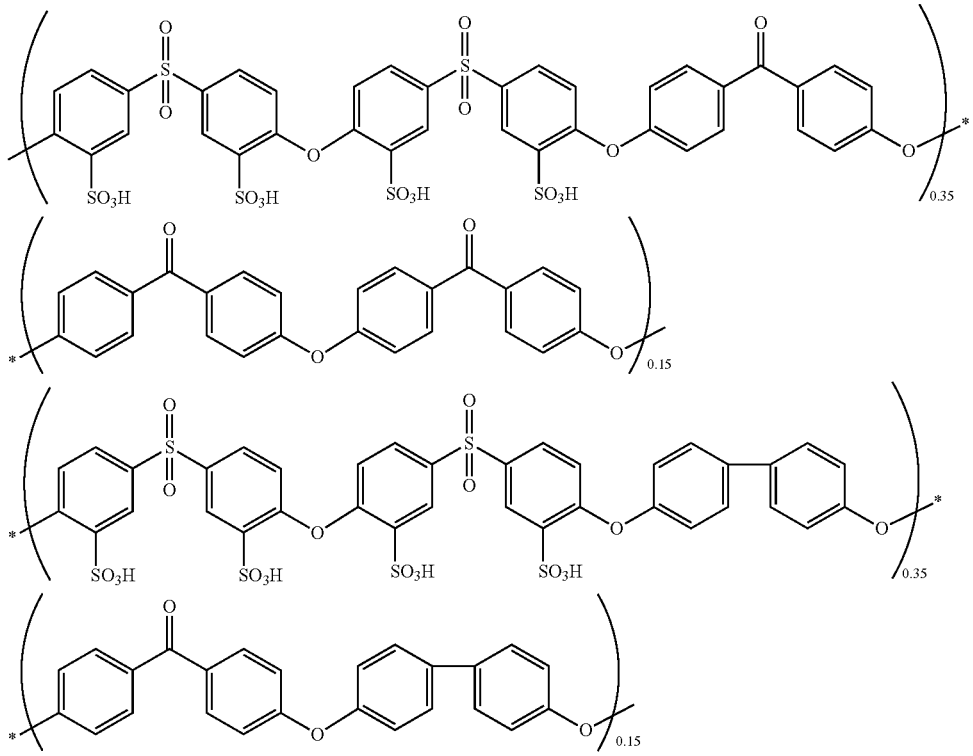

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G10) given above. The resulting film had a sulfonic acid group density of 3.1 meq/g.

The resulting film had a film thickness of 25 μm and a high degree of proton conductivity of 280 mS/cm at 80° C. and a relative humidity of 85%. The dimensional stability in hot water was inferior compared to Example 5. Furthermore, NMR analysis showed the absence of ketal groups.

Example 9

Except that 12.7 g of the aromatic sulfonic acid derivative obtained in Example 3 was used instead of the aromatic sulfonic acid derivative obtained in Example 1, the same polymerization procedure as in Example 7 was carried out to produce a ketal-containing precursor polymer. It had a weight average molecular weight of 300,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G11) given above. The resulting film had a sulfonic acid group density of 3.7 meq/g.

The resulting film had a film thickness of 25 μm and a degree of proton conductivity of 360 mS/cm at 80° C. and a relative humidity of 85%. Furthermore, NMR analysis showed the absence of ketal groups.

Comparative Example 1

Various characteristics were evaluated by using a commercial film of Nafion (registered trademark) 111 (manufactured by DuPont). Nafion (registered trademark) 111 film was immersed in a 5% hydrogen peroxide solution at 100° C. for 30 minutes and then in a 5% dilute sulfuric acid at 100° C. for 30 minutes, followed by adequate washing with deionized water at 100° C. The degree of proton conductivity was 100 mS/cm at 80° C. and a relative humidity of 85%.

Example 10

A Sulfonic Acid Group-Containing Polymer as Represented by the General Formula (G12) Given Below obtained in Example 2, and 2.6 g of 18-crown-6-ether were fed, followed by dehydration with 50 mL of N-methyl pyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 340,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G12) given above. The resulting film had a sulfonic acid group density of 3.6 meq/g.

The resulting film had a film thickness of 25 μm, a high degree of proton conductivity of 390 mS/cm at 80° C. and a

[Chemical formula 43]

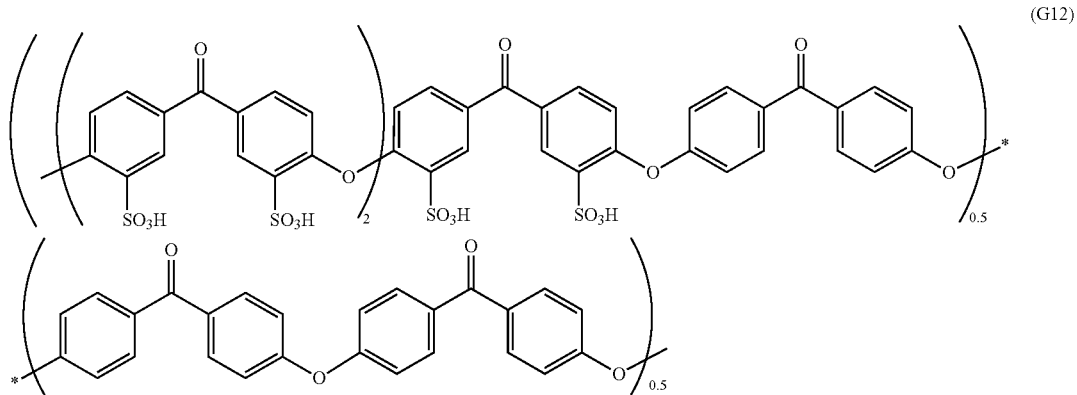

(G12)

(In the general formula, * represents the position where the upper part of the general formula and the lower part of the general formula are bonded to each other.)

To a 500 mL three-neck flask equipped with a stirrer, nitrogen supply tube, and Dean-Stark trap, 5.5 g of potassium carbonate, 5.2 g of the 2,2-bis(4-hydroxyphenyl)-1,3-dioxane mixture obtained in Synthesis example 1, 2.2 g of 4,4'-difluorobenzophenone, 12.5 g of the aromatic sulfonic acid derivative represented by the formula (G4) given above relative humidity of 85%, and an excellent dimensional stability in hot water. Furthermore, NMR analysis showed the absence of ketal groups.

Example 11

A Sulfonic Acid Group-Containing Polymer as Represented by the General Formula (G13) Given Below

[Chemical formula 44]

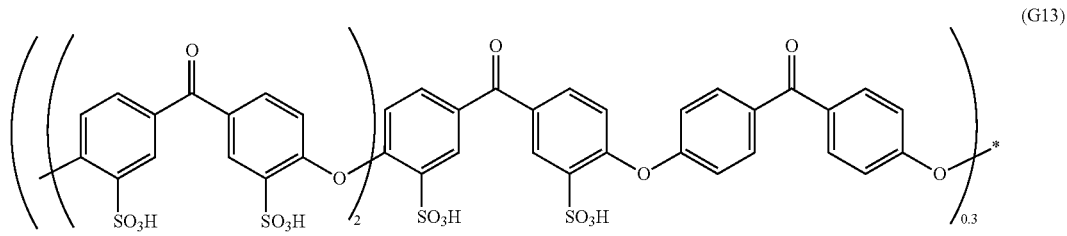

(G13)

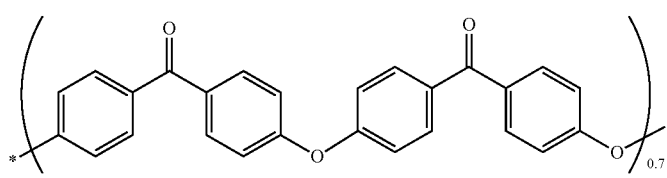

(In the general formula, * represents the position where the upper part of the general formula and the lower part of the general formula are bonded to each other.)

To a 500 mL three-neck flask equipped with a stirrer, nitrogen supply tube, and Dean-Stark trap, 4.4 g of potassium carbonate, 5.2 g of the 2,2-bis(4-hydroxyphenyl)-1,3-dioxane mixture obtained in Synthesis example 1, 3.1 g of 4,4'-difluorobenzophenone, 7.5 g of the aromatic sulfonic acid derivative represented by the formula (G4) given above obtained in Example 2, and 1.6 g of 18-crown-6-ether were fed, followed by dehydration with 50 mL of N-methyl pyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 310,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G13) given above. The resulting film had a sulfonic acid group density of 2.7 meq/g.

The resulting film had a film thickness of 24 nm, a high degree of proton conductivity of 270 mS/cm at 80° C. and a relative humidity of 85%, and an excellent dimensional stability in hot water. Furthermore, NMR analysis showed the absence of ketal groups.

Example 12

A Sulfonic Acid Group-Containing Polymer as Represented by the General Formula (G14) Given Below

[Chemical formula 45]

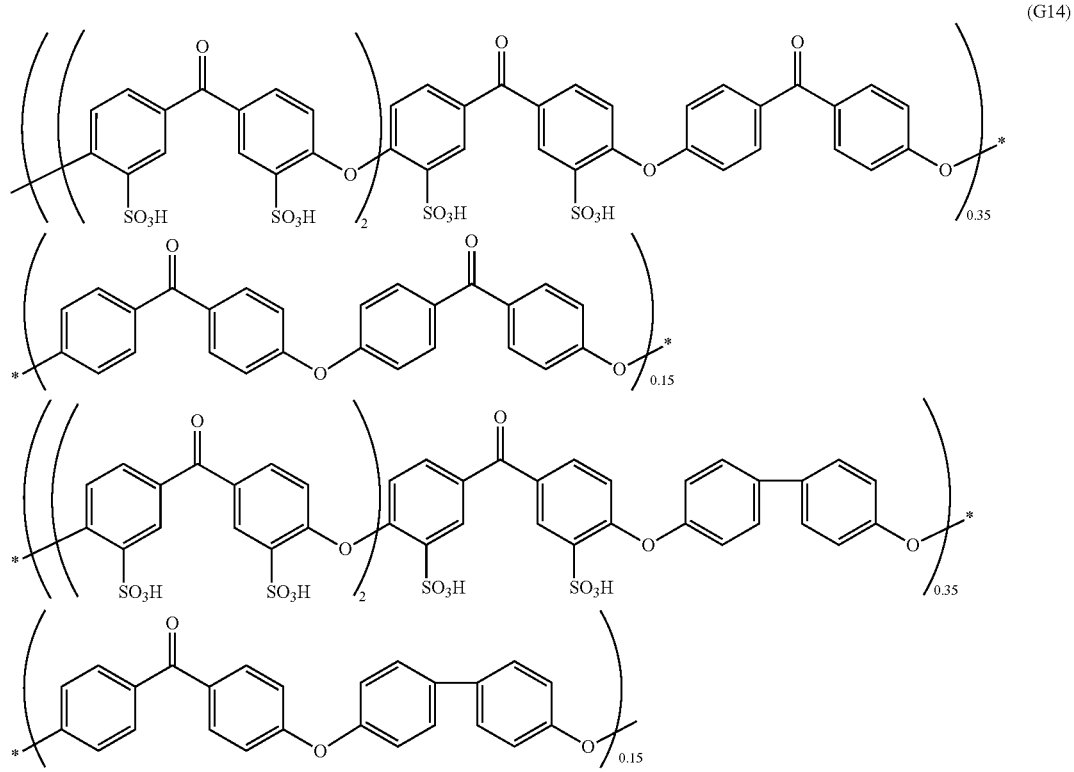

(In the general formula, * represents the position where the upper part of the general formula and the lower part of the general formula are bonded to each other.)

To a 500 mL three-neck flask equipped with a stirrer, nitrogen supply tube, and Dean-Stark trap, 6.6 g of potassium carbonate, 2.6 g of the 2,2-bis(4-hydroxyphenyl)-1,3-dioxane mixture obtained in Synthesis example 1, 1.9 g of 4,4'-biphenol, 1.3 g of 4,4'-difluorobenzophenone, 17.4 g of the aromatic sulfonic acid derivative represented by the formula (G4) given above obtained in Example 2, and 3.7 g of 18-crown-6-ether were fed, followed by dehydration with 50 mL of N-methylpyrolidone (NMP) and 40 mL of toluene at 180° C., heating to remove toluene, and polymerization at 200° C. for 3 hours. The material was purified by reprecipitation with a large amount of water to obtain a precursor polymer having a ketal group. It had a weight average molecular weight of 250,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G14) given above. The resulting film had a high sulfonic acid group density of 4.1 meq/g.

The resulting film had a film thickness of 27 μm and a very high degree of proton conductivity of 450 mS/cm at 80° C. and a relative humidity of 85%. Furthermore, NMR analysis showed the absence of ketal groups.

sulfonic acid derivative obtained in Example 2, the same polymerization procedure as in Example 10 was carried out to produce a ketal-containing precursor polymer. It had a weight average molecular weight of 360,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G15) given above. The resulting film had a sulfonic acid group density of 3.7 meq/g.

The resulting film had a film thickness of 25 μm and a degree of proton conductivity of 360 mS/cm at 80° C. and a relative humidity of 85%. The dimensional stability in hot water was inferior compared to Example 10. Furthermore, NMR analysis showed the absence of ketal groups.

Example 13

[Chemical formula 46]

Example 14

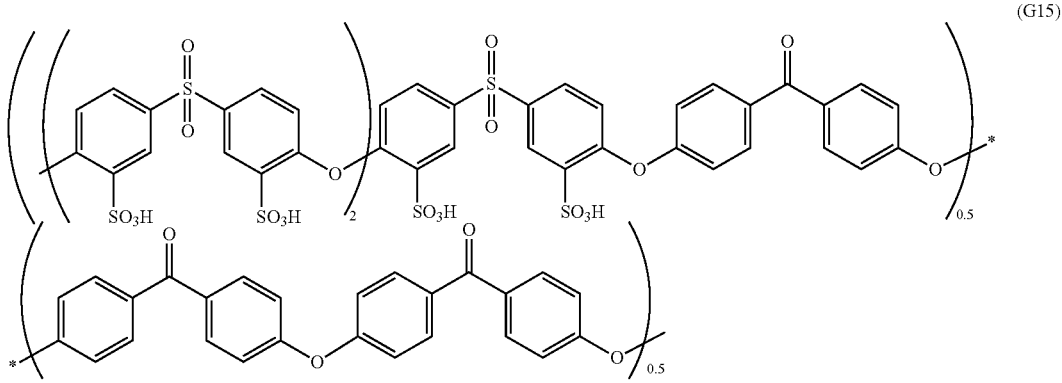

(G15)

Except that 13.6 g of the aromatic sulfonic acid derivative obtained in Example 4 was used instead of the aromatic

[Chemical formula 47]

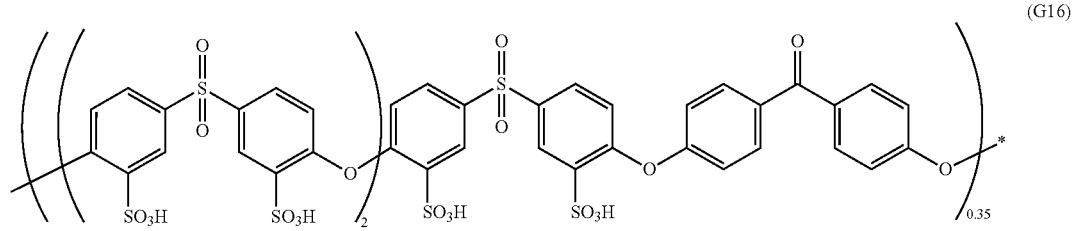

(G16)

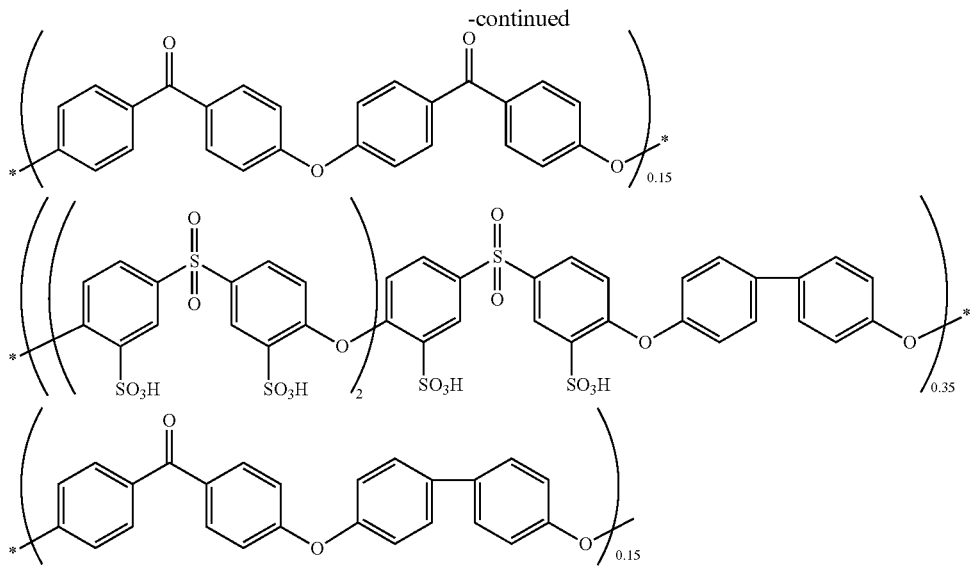

-continued

Except that 19.0 g of the aromatic sulfonic acid derivative obtained in Example 4 was used instead of the aromatic sulfonic acid derivative obtained in Example 2, the same polymerization procedure as in Example 12 was carried out to produce a ketal-containing precursor polymer. It had a weight average molecular weight of 270,000.

A 25 wt % N-methylpyrolidone (NMP) solution of the resulting precursor polymer was flow-cast on a glass substrate, dried at 100° C. for 4 hours, and heat-treated in nitrogen at 150° C. for 30 minutes to obtain a film. Before molding, the sulfonic acid group-containing polymer had a very high solubility. The material was immersed in a 10 wt % sulfuric acid aqueous solution at 25° C. for 24 hours for proton substitution and deprotection reaction and then immersed in a large excess of pure water for 24 hours to ensure adequate washing to obtain a polymer electrolyte membrane of a sulfonic acid group-containing polymer as represented by the formula (G16) given above. The resulting film had a sulfonic acid group density of 4.2 meq/g.

The resulting film had a film thickness of 25 μm and a degree of proton conductivity of 400 mS/cm at 80° C. and a relative humidity of 85%. Furthermore, NMR analysis showed the absence of ketal groups.

Example 15

Synthesis of an Ionic Group-Free Oligomer a1' as Represented by the General Formula (G17) Given Below (In the formula, m represents a positive integer.)

To a 1,000 mL three-neck flask equipped with a stirrer, nitrogen supply tube, and Dean-Stark trap, 16.59 g of potassium carbonate (reagent manufactured by Aldrich, 120 mmol), 25.8 g of the 2,2-bis(4-hydroxyphenyl)-1,3-dioxane (K-DHBP) obtained in Synthesis example 1 (100 mmol), and 20.3 g of 4,4'-difluorobenzophenone (reagent manufactured by Aldrich, 93 mmol) were fed, followed by nitrogen purge, dehydration in 300 mL of N-methylpyrolidone (NMP) and 100 mL of toluene at 160° C., heating to remove toluene, and polymerization at 180° C. for 1 hour. The material was purified by reprecipitation with a large amount of methanol to obtain an ionic group-free oligomer a1 (with terminal OM groups). Here, M represents Na or K, and this will apply hereinafter. It had a number average molecular weight of 10,000.

To a 500 mL three-neck flask equipped with a stirrer, nitrogen supply tube, and Dean-Stark trap, 1.1 g of potassium carbonate (reagent manufactured by Aldrich, 8 mmol) and 20.0 g (2 mmol) of the ionic group-free oligomer a1 (with terminal OM groups) were fed, followed by nitrogen purge, dehydration in 100 mL of N-methylpyrolidone (NMP) and 30 mL of cyclohexane at 100° C., heating to remove cyclohexane, addition of 4.0 g of Decafluorobiphenyl (reagent manufactured by Aldrich, 12 mmol) and reaction at 105° C. for 1 hour. The material was purified by reprecipitation with a large amount of isopropyl alcohol to obtain an ionic group-free oligomer a1' (with terminal fluoro groups) as represented by

[Chemical formula 48]

(G17)

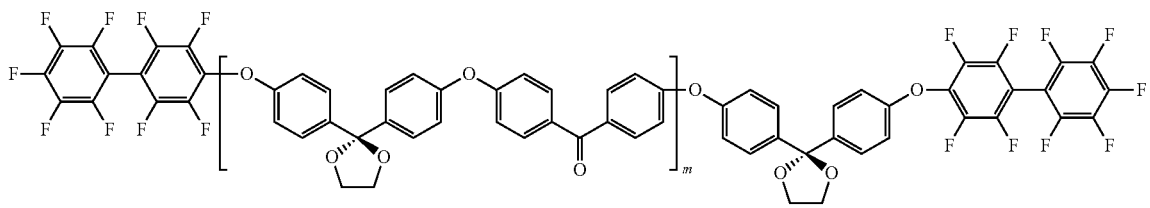

the formula (G17) given above. It had a number average molecular weight of 11,000, and the number average molecular weight of the ionic group-free oligomer a1 was calculated at 10,400 by subtracting a value corresponding to the linker portion (molecular weight 630).

Synthesis of an Ionic Group-Containing Oligomer a2 as Represented by the General Formula (G18) Given Below

[Chemical formula 49]

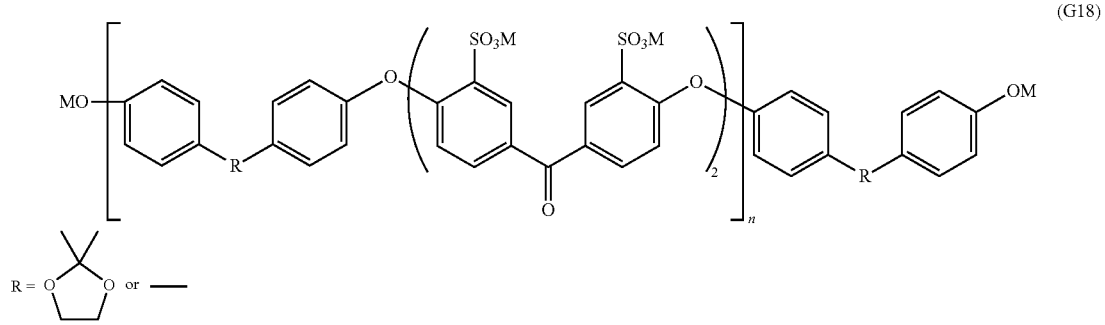

(G18)

(In the formula (G18), M represents Na or K, and n represents a positive integer.)

To a 1,000 mL three-neck flask equipped with a stirrer, nitrogen supply tube, and Dean-Stark trap, 41.5 g of potassium carbonate (reagent manufactured by Aldrich, 300 mmol), 12.9 g (50 mmol) of the 2,2-bis(4-hydroxyphenyl)-1,3-dioxane (K-DHBP) obtained in Synthesis example 1, 9.3 g of 4,4'-biphenol (reagent manufactured by Aldrich, 50 mmol), 76.5 g (93 mmol) of the aromatic sulfonic acid derivative obtained in Example 1, and 49.1 g of 18-crown-6-ether (manufactured by Wako Pure Chemical Industries, Ltd., 186 mmol) were fed, followed by nitrogen purge, dehydration in 400 mL of N-methylpyrolidone (NMP) and 150 mL of toluene at 170° C., heating to remove toluene, and polymerization at 180° C. for 1 hour. The material was purified by reprecipitation with a large amount of isopropyl alcohol to obtain an ionic group-containing oligomer a2 as represented by the formula (G18) given above (with terminal OM groups). It had a number average molecular weight of 16,000.

Synthesis of Block Copolymer b1 Containing Oligomer a2 as Ionic Group-Containing Segment (A1), Oligomer a1 as Ionic Group-Free Segment (a2), and Octafluorobiphenylene as Linker Portion To a 500 mL three-neck flask equipped with a stirrer, nitrogen supply tube, and Dean-Stark trap, 0.56 g of potassium carbonate (reagent manufactured by Aldrich, 4 mmol) and 16 g (1 mmol) of the ionic group-containing oligomer a2 (with terminal OM groups) were fed, followed by nitrogen purge, dehydration in 100 mL of N-methylpyrolidone (NMP) and 30 mL of cyclohexane at 100° C., heating to remove cyclohexane, addition of 11 g (1 mmol) of the ionic group-free oligomer a1' (terminal fluoro group), and reaction at 105° C. for 24 hour. The material was purified by reprecipitation with a large amount of isopropyl alcohol to obtain a block copolymer b1. It had a weight average molecular weight of 290,000.

In the block copolymer b1, the constituent units as represented by the general formula (51) accounted for 33 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 33 mol %, 0 mol %, 0 mol %, and 67 mol %, respectively, meeting the relation $0 \leq Y < X < Z < 1$ (T1).

A 25 wt % N-methylpyrolidone (NMP) solution of the resulting block copolymer b1 was subjected to pressure filtration through a glass fiber filter and flow-cast on a glass substrate, dried at 100° C. for 4 hours, and heat-treated in nitrogen at 150° C. for 10 minutes to obtain a polyketal ketone film (film thickness 25 μm). The polymer had a very high solubility. The material was immersed in a 10 wt % sulfuric acid aqueous solution at 95° C. for 24 hours for proton substitution and deprotection reaction and then immersed in a large excess of pure water for 24 hours to ensure adequate washing to obtain a polymer electrolyte membrane.

Its ion exchange capacity was determined to be 2.2 meq/g from neutralization titration, and the molar content ratio (A1/A2) was determined to be 1.18 (66/56) from $^1$H-NMR, with no ketal groups found to remain. The electrolyte membrane was very tough as well as transparent and uniform from visual observation. It had a degree of proton conductivity of 500 mS/cm at 80° C. and a relative humidity of 85% and 20 mS/cm at 80° C. and a relative humidity of 25%, and had a high proton conductivity under low humidify conditions. It showed only a small dimensional change rate of 11% and a high hot water resistance. It had a molecular weight retention rate of 81% and high chemical stability.

In addition, co-continuous phase-separated structures with a domain size of 20 nm were confirmed by TEM observation. It was found that both ionic group-containing domains and ionic group-free domains formed continuous phases.

Example 16

Synthesis of an Ionic Group-Free Oligomer a3' as Represented by the General Formula (G17) Given Above Except for feeding 20.7 g of 4,4'-difluorobenzophenone (reagent manufactured by Aldrich, 95 mmol), the same procedure as described in Example 15 was carried out to synthesize an ionic group-free oligomer a3 (with terminal OM groups). It had a number average molecular weight of 15,000.

In addition, except for feeding 30.0 g (2 mmol) of the ionic group-free oligomer a3 (with terminal OM groups) instead of the ionic group-free oligomer a1 (with terminal OM groups), the same procedure as described in Example 15 was carried out to synthesize an ionic group-free oligomer a3' (with terminal fluoro groups) as represented by the formula (G17) given above. It had a number average molecular weight of 16,000, and the number average molecular weight of the ionic group-free oligomer a3' was calculated at 15,400 by subtracting a value corresponding to the linker portion (molecular weight 630).

Synthesis of an Ionic Group-Containing Oligomer a4 as Represented by the General Formula (G18) Given Above Except for feeding 78.1 g (95 mmol) of the aromatic sulfonic acid derivative obtained in Example 1 and feeding 25.8 g (100 mmol) of 2,2-bis(4-hydroxyphenyl)-1,3-dioxane (K-DHBP) as a bisphenol, the same procedure as described in Example 15 was carried out to produce an ionic group-containing oligomer a4 (with terminal OM groups) as represented by the formula (G18) given above. It had a number average molecular weight of 21,000.

Synthesis of Block Copolymer b2 Containing Oligomer a4 as Ionic Group-Containing Segment (A1), Oligomer a3 as Ionic Group-Free Segment (a2), and Octafluorobiphenylene as Linker Portion Except for feeding 21 g (1 mmol) of an ionic group-containing oligomer a4 (with terminal OM groups) instead of an ionic group-containing oligomer a2 (with terminal OM groups) and feeding 16 g (1 mmol) of an ionic group-free oligomer a3' (with terminal fluoro groups) instead of an ionic group-free oligomer a1' (with terminal fluoro groups), the same procedure as described in Example 15 was carried out to produce a block copolymer b2. It had a weight average molecular weight of 420,000.

In the block copolymer b2, the constituent units as represented by the general formula (S1) accounted for 33 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 33 mol %, 0 mol %, 0 mol %, and 67 mol %, respectively, meeting the relation $0 \leq Y < X < Z < 1$ (T1).

Using a 25 wt % N-methylpyrolidone (NMP) solution of the resulting block copolymer b2, the procedure described in Example 15 was carried out to produce a polymer electrolyte membrane.

Its ion exchange capacity was determined to be 2.0 meq/g from neutralization titration, and the molar content ratio (A1/A2) was determined to be 1 (66/66) from $^1$H-NMR, with no ketal groups found to remain. The electrolyte membrane was very tough as well as transparent and uniform from visual observation. It had a degree of proton conductivity of 400 mS/cm at 80° C. and a relative humidity of 85% and 10 mS/cm at 80° C. and a relative humidity of 25%, and had a high proton conductivity under low humidify conditions. It showed only a small dimensional change rate of 8% and a high hot water resistance. It had a molecular weight retention rate of 90% and high chemical stability.

In addition, co-continuous phase-separated structures with a domain size of 30 nm were confirmed by TEM observation. It was found that both ionic group-containing domains and ionic group-free domains formed continuous phases.

Example 17

Synthesis of an Ionic Group-Free Oligomer a1' as Represented by the General Formula (G17) Given Above The same procedure as described in Example 15 was carried out to obtain an ionic group-free oligomer a1' as represented by the formula (G17) given above (with terminal fluoro groups). It had a number average molecular weight of 11,000, and the number average molecular weight of the ionic group-free oligomer a1 was calculated at 10,400 by subtracting a value corresponding to the linker portion (molecular weight 630).

Synthesis of an Ionic Group-Containing Oligomer a5 as Represented by the General Formula (G19) Given Below

[Chemical formula 50]

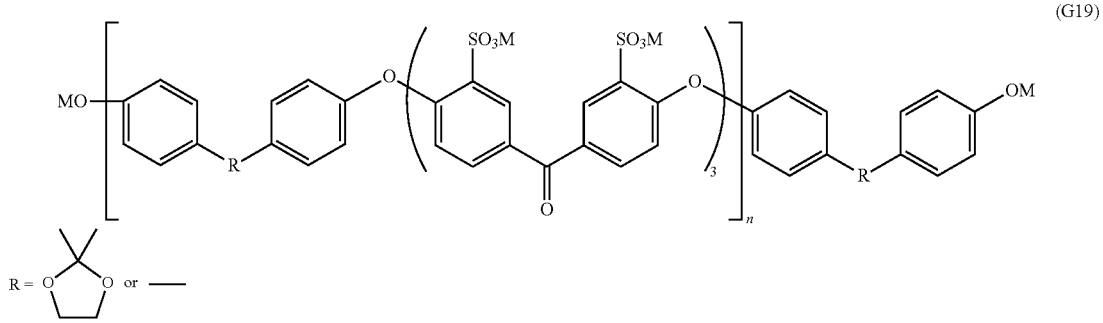

(G19)

(In the formula (G19), M represents Na or K, and n represents a positive integer.)

To a 1,000 mL three-neck flask equipped with a stirrer, nitrogen supply tube, and Dean-Stark trap, 41.5 g of potassium carbonate (reagent manufactured by Aldrich, 300 mmol), 12.9 g (50 mmol) of the 2,2-bis(4-hydroxyphenyl)-1,3-dioxane (K-DHBP) obtained in Synthesis example 1, 9.3 g of 4,4'-biphenol (reagent manufactured by Aldrich, 50 mmol), 113.7 g (93 mmol) of the aromatic sulfonic acid derivative obtained in Example 2, and 73.7 g of 18-crown-6- ether (manufactured by Wako Pure Chemical Industries, Ltd., 279 mmol) were fed, followed by nitrogen purge, dehydration in 500 mL of N-methylpyrolidone (NMP) and 200 mL of toluene at 170° C., heating to remove toluene, and polymerization at 180° C. for 1 hour. The material was purified by reprecipitation with a large amount of isopropyl alcohol to obtain an ionic group-containing oligomer a5 (with terminal OM groups) as represented by the formula (G19) given above. It had a number average molecular weight of 16,000.

Synthesis of Block Copolymer b3 Containing an Oligomer a5 as Ionic Group-Containing Segment (a1), Oligomer a1' as Ionic Group-Free Segment (a2), and Octafluorobiphenylene as Linker Portion To a 500 mL three-neck flask equipped with a stirrer, nitrogen supply tube, and Dean-Stark trap, 0.56 g of potassium carbonate (reagent manufactured by Aldrich, 4 mmol) and 16 g (1 mmol) of the ionic group-containing oligomer a5 (with terminal OM groups) were fed, followed by nitrogen purge, dehydration in 120 mL of N-methylpyrolidone (NMP) and 30 mL of cyclohexane at 100° C., heating to remove cyclohexane, addition of 11 g (1 mmol) of the ionic group-free oligomer a1' (terminal fluoro group), and reaction at 105° C. for 24 hour. The material was purified by reprecipitation with a large amount of isopropyl alcohol to obtain a block copolymer b3. It had a weight average molecular weight of 310,000.

In the block copolymer b3, the constituent units as represented by the general formula (S1) accounted for 50 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 25 mol %, 0 mol %, 0 mol %, and 75 mol %, respectively, meeting the relation $0 \le Y < X < Z < 1$ (T1).

A 25 wt % N-methylpyrolidone (NMP) solution of the resulting block copolymer b3 was subjected to pressure filtration through a glass fiber filter and flow-cast on a glass substrate, dried at 100° C. for 4 hours, and heat-treated in nitrogen at 150° C. for 10 minutes to obtain a polyketal ketone film (film thickness 25 μm). The polymer had a very high solubility. The material was immersed in a 10 wt % sulfuric acid aqueous solution at 95° C. for 24 hours for proton substitution and deprotection reaction and then immersed in a large excess of pure water for 24 hours to ensure adequate washing to obtain a polymer electrolyte membrane.

Its ion exchange capacity was determined to be 2.4 meq/g from neutralization titration, and the molar content ratio (A1/A2) was determined to be 1.57 (88/56) from $^1$H-NMR, with no ketal groups found to remain. The electrolyte membrane was very tough as well as transparent and uniform from visual observation. It had a degree of proton conductivity of 900 mS/cm at 80° C. and a relative humidity of 85% and 50 mS/cm at 80° C. and a relative humidity of 25%, and had a high proton conductivity under low humidify conditions. It showed only a small dimensional change rate of 13% and a high hot water resistance. It had a molecular weight retention rate of 83% and high chemical stability.

In addition, co-continuous phase-separated structures with a domain size of 20 nm were confirmed by TEM observation. It was found that both ionic group-containing domains and ionic group-free domains formed continuous phases.

Example 18

Synthesis of an Ionic Group-Free Oligomer a3' as Represented by the General Formula (G17) Given Above The same procedure as described in Example 16 was carried out to synthesize an ionic group-free oligomer a3' as represented by the formula (G17) given above (with terminal fluoro groups). It had a number average molecular weight of 16,000, and the number average molecular weight of the ionic group-free oligomer a3 was calculated at 15,400 by subtracting a value corresponding to the linker portion (molecular weight 630).

Synthesis of an Ionic Group-Containing Oligomer a6 as Represented by the General Formula (G20) Given Below

[Chemical formula 51]

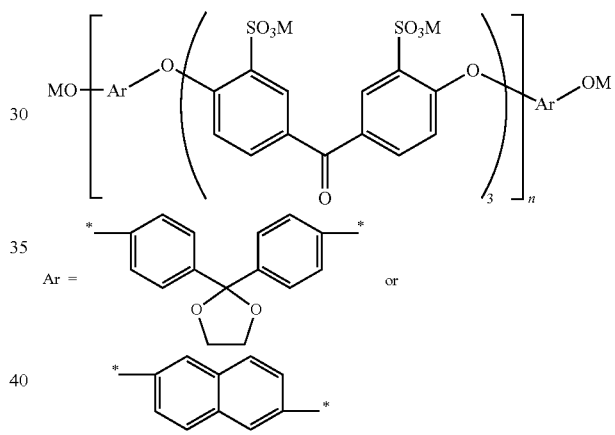

(In the formula (G20), * represents bonding positions; M represents Na or K; and n represents a positive integer.)

Except for feeding 116.2 g (95 mmol) of the aromatic sulfonic acid derivative obtained in Example 2, feeding 12.9 g (50 mmol) of 2,2-bis(4-hydroxyphenyl)-1,3-dioxane (K-DHBP) as a bisphenol, and feeding 8.0 g of 1,5-dihydroxy naphthalene (reagent manufactured by Aldrich, 50 mmol), the same procedure as described in Example 16 was carried out to produce an ionic group-containing oligomer a6 (with terminal OM groups) as represented by the formula (G20) given above. It had a number average molecular weight of 21,000.

Synthesis of Block Copolymer b4 Containing Oligomer a6 as Ionic Group-Containing Segment (A1), Oligomer a3 as Ionic Group-Free Segment (a2), and Octafluorobiphenylene as Linker Portion Except for feeding 21 g (1 mmol) of an ionic group-containing oligomer a6 (with terminal OM groups) instead of an ionic group-containing oligomer a2 (with terminal OM groups) and feeding 16 g (1 mmol) of an ionic group-free oligomer a3' (with terminal fluoro groups) instead of an ionic group-free oligomer a1' (with terminal fluoro groups), the same procedure as described in Example 16 was carried out to produce a block copolymer b4. It had a weight average molecular weight of 450,000.

In the block copolymer b4, the constituent units as represented by the general formula (S1) accounted for 50 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 12.5 mol %, 12.5 mol %, 0 mol %, and 75 mol %, respectively, meeting the relation 0≤Y<X<Z<1 (T1).

Using a 25 wt % N-methylpyrrolidone (NMP) solution of the resulting block copolymer b4, the procedure described in Example 15 was carried out to produce a polymer electrolyte membrane.

Its ion exchange capacity was determined to be 2.3 meq/g from neutralization titration, and the molar content ratio (A1/A2) was determined to be 1.33 (80/60) from $^1$H-NMR, with no ketal groups found to remain. The electrolyte membrane was very tough as well as transparent and uniform from visual observation. It had a degree of proton conductivity of 700 mS/cm at 80° C. and a relative humidity of 85% and 35 mS/cm at 80° C. and a relative humidity of 25%, and had a high proton conductivity under low humidify conditions. It showed only a small dimensional change rate of 10% and a high hot water resistance. It had a molecular weight retention rate of 93% and high chemical stability.

In addition, co-continuous phase-separated structures with a domain size of 40 nm were confirmed by TEM observation. It was found that both ionic group-containing domains and ionic group-free domains formed continuous phases.

Example 19

Synthesis of Ionic Group-Containing Oligomer e2

[Chemical formula 52]

Of the ionic group-containing oligomers synthesized in Example 15, the aromatic sulfonic acid derivatives obtained in Example 1 was replaced with 83.2 g (93 mmol) of the aromatic sulfonic acid derivative obtained in Example 3 was used, and except for this, the same oligomer synthesis procedure as in Example 15 was carried out to produce an ionic group-containing oligomer e2 (with terminal OM groups) as represented by the formula (G21). It had a number average molecular weight of 16,000.

Synthesis of Block Copolymer f1 Containing the Oligomer e2 as Ionic Group-Containing Segment (a1), Oligomer a1 as Ionic Group-Free Segment (a2), and Octafluorobiphenylene as Linker Portion Of the oligomers used in Example 15, the ionic group-containing oligomer a2 (with terminal OM groups) was replaced with 16 g (1 mmol) of the ionic group-containing oligomer e2 (with terminal OM groups), and except for this, the same procedure as in Example 15 was carried out for perform polymerization. A block copolymer f1 was obtained. It had a weight average molecular weight of 300,000.

In the block copolymer f1, the constituent units as represented by the general formula (S1) accounted for 33 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 33 mol %, 0 mol %, 0 mol %, and 67 mol %, respectively, meeting the relation 0≤Y<X<Z<1 (T1).

A 25 wt % N-methylpyrrolidone (NMP) solution of the resulting block copolymer f1 was subjected to pressure filtration through a glass fiber filter and flow-cast on a glass substrate, dried at 100° C. for 4 hours, and heat-treated in nitrogen at 150° C. for 10 minutes to obtain a polyketal ketone film (film thickness 25 μm). The polymer had a very high solubility. The material was immersed in a 10 wt % sulfuric acid aqueous solution at 95° C. for 24 hours for proton substitution and deprotection reaction and then immersed in a large excess of pure water for 24 hours to ensure adequate washing to obtain a polymer electrolyte membrane.

Its ion exchange capacity was determined to be 2.2 meq/g from neutralization titration, and the molar content ratio (A1/A2) was determined to be 1.16 (65/56) from $^1$H-NMR, with no ketal groups found to remain. It had a degree of proton conductivity of 480 mS/cm at 80° C. and a relative humidity of 85% and 10 mS/cm at 80° C. and a relative humidity of 25% and had a small dimensional change rate of 16%, showing that it had a high proton conductivity under low humidify

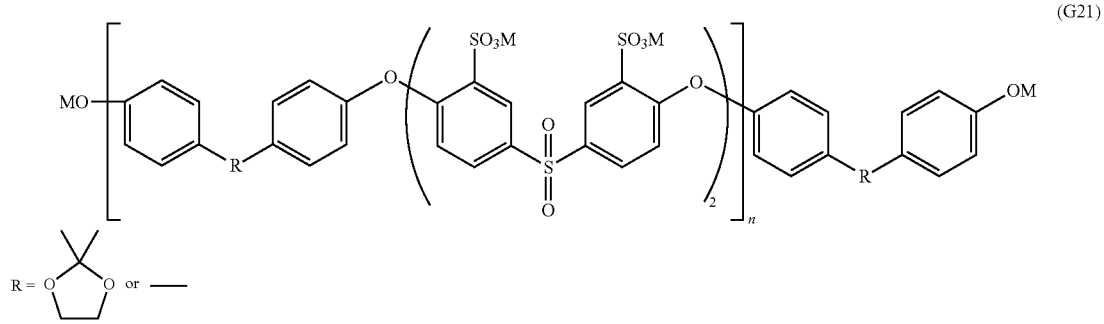

conditions and a high hot water resistance though inferior compared to Example 15. It had a molecular weight retention rate of 82% and high chemical stability.

In addition, co-continuous phase-separated structures with a domain size of 22 nm were confirmed by TEM observation. It was found that both ionic group-containing domains and ionic group-free domains formed continuous phases.

Example 20

Synthesis of Ionic Group-Containing Oligomer e3 by Post-Sulfonation

[Chemical formula 53]

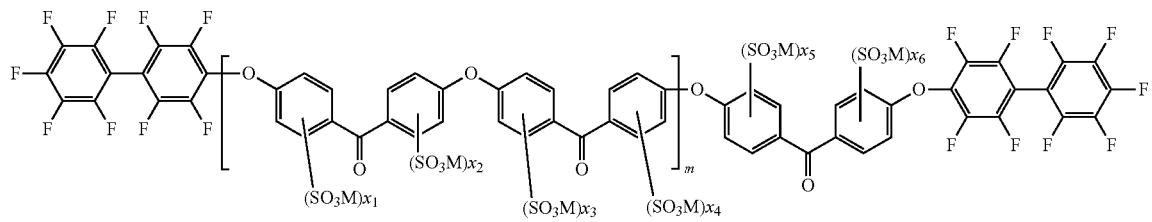

(G22)

(In the above formula, M represents Na or K; m represents an integer; and x1 to x6 each represent an integer of 0 or greater.)

First, 20 g of the ionic group-free oligomer a1' (with terminal fluoro groups and a number average molecular weight of 16,000) represented by the general formula (G17) synthesized by the same procedure as in Example 15 was reacted in 55 g of fuming sulfuric acid (30% $SO_3$) (reagent manufactured by Wako Pure Chemical Industries, Ltd.) at 120° C. for 24 hours. The solution was added little by little to a large amount of water and neutralized with NaOH, followed by precipitating sodium sulfate with ethanol three times to remove it, thereby obtaining an ionic group-containing oligomer e3 as represented by the formula (G22) given above. It had a molecular weight of 21,000.

Synthesis of Block Copolymer f2 Containing the Oligomer e3 as Ionic Group-Containing Segment (a1), Oligomer a3 as Ionic Group-Free Segment (a2), and Octafluorobiphenylene as Linker Portion Except for feeding 21 g (1 mmol) of an ionic group-containing oligomer e3 (with terminal fluoro groups) instead of an ionic group-containing oligomer a2 (with terminal OM groups) and feeding 16 g (1 mmol) of an ionic group-free oligomer a3 (with terminal OM groups and a number average molecular weight of 15,000) synthesized in Example 16 instead of an ionic group-free oligomer a1' (with terminal fluoro groups), the same procedure as described in Example 15 was carried out to produce a block copolymer f2. It had a weight average molecular weight of 380,000.

In the block copolymer f2, the constituent units as represented by the general formula (S1) accounted for 33 mol % of the ionic group-containing segments (A1), and the constituent units as represented by the general formula (NP1) accounted for 100 mol % of the ionic group-free segments (A2). In the ionic group-containing segments (A1), the constituent units as represented by the general formulae (Q1), (Q2), (Q3), and (Q4) accounted for molar fractions of 33 mol %, 0 mol %, 0 mol %, and 67 mol %, respectively, meeting the relation $0 \leq Y < X < Z < 1$ (T1).

A 25 wt % N-methylpyrolidone (NMP) solution of the resulting block copolymer f2 was subjected to pressure filtration through a glass fiber filter and flow-cast on a glass substrate, dried at 100° C. for 4 hours, and heat-treated in nitrogen at 150° C. for 10 minutes to obtain a polyketal ketone film (film thickness 25 μm). The polymer had a very high solubility. The material was immersed in a 10 wt % sulfuric acid aqueous solution at 95° C. for 24 hours for proton substitution and deprotection reaction and then immersed in a large excess of pure water for 24 hours to ensure adequate washing to obtain a polymer electrolyte membrane.

Its ion exchange capacity was determined to be 2.1 meq/g from neutralization titration, and the molar content ratio (A1/A2) was determined to be 1.12 (56/50) from $^1$H-NMR, with no ketal groups found to remain. The electrolyte membrane was very tough as well as transparent and uniform from visual observation. It had a degree of proton conductivity of 390 mS/cm at 80° C. and a relative humidity of 85% and 9 mS/cm at 80° C. and a relative humidity of 25%, and had a high proton conductivity under low humidify conditions. It showed only a small dimensional change rate of 9% and a high hot water resistance. It had a molecular weight retention rate of 92% and high chemical stability.

In addition, co-continuous phase-separated structures with a domain size of 32 nm were confirmed by TEM observation. It was found that both ionic group-containing domains and ionic group-free domains formed continuous phases.

Comparative Example 2

Various characteristics were evaluated by using a commercial film of Nafion (registered trademark) NRE211CS (manufactured by DuPont). Its ion exchange capacity was determined to be 0.9 meq/g from neutralization titration. It was a transparent, uniform film from visual observation, and distinct phase-separated structures were not found in TEM observation. It had a degree of proton conductivity of 100 mS/cm at 80° C. and a relative humidity of 85% and 3 mS/cm at 80° C. and a relative humidity of 25%. Furthermore, it violently swelled when immersed in hot water, and it was so difficult to handle that it sometimes broke when held.

Comparative Example 3

Synthesis of an Ionic Group-Containing Oligomer a7 as Represented by the General Formula (G23) Given Below To a 1,000 mL three-neck flask equipped with a stirrer, nitrogen supply tube, and Dean-Stark trap, 27.6 g of potassium carbonate (reagent manufactured by Aldrich, 200 mmol), 12.9 g (50 mmol) of the 2,2-bis(4-hydroxyphenyl)-1,3-dioxane mixture obtained in Synthesis example 1, 9.3 g of 4,4'-biphenol (reagent manufactured by Aldrich, 50 mmol), 39.3 g (93 mmol) of the disodium-3,3'-disulfonate-4,4'-difluorobenzophenone obtained in Synthesis example 2 given above, and 17.9 g of 18-crown-6-ether (manufactured by Wako Pure Chemical Industries, Ltd., 82 mmol) were fed, followed by nitrogen purge, dehydration in 300 mL of N-methylpyrolidone (NMP) and 100 mL of toluene at 170° C., heating to remove toluene, and polymerization at 180° C. for 1 hour. The material was purified by reprecipitation with a large amount of isopropyl alcohol to obtain an ionic group-containing oligomer a7 (with terminal OM groups) as represented by the formula (G23) given below. It had a number average molecular weight of 16,000.

nitrogen at 150° C. for 10 minutes to obtain a polyketal ketone film (film thickness 25 μm). The polymer had a very high solubility. The material was immersed in a 10 wt % sulfuric acid aqueous solution at 95° C. for 24 hours for proton substitution and deprotection reaction and then immersed in a large excess of pure water for 24 hours to ensure adequate washing to obtain a polymer electrolyte membrane.

Its ion exchange capacity was determined to be 1.7 meq/g from neutralization titration, and the molar content ratio (A1/A2) was determined to be 54 moles/46 moles=1.17 from $^1$H-NMR, with no ketal groups found to remain. The electrolyte membrane was very tough as well as transparent and uniform from visual observation. It had a high degree of proton conductivity of 240 mS/cm at 80° C. and a relative humidity of 85% and 2 mS/cm at 80° C. and a relative humid-

[Chemical formula 54]

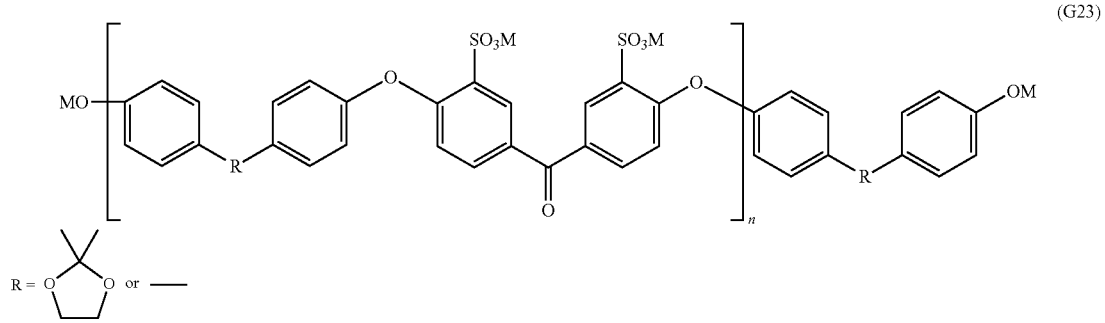

(In the formula (G23), M represents Na or K, and n represents a positive integer.)

Synthesis of Block Copolymer b5 Containing an Oligomer a7 as Ionic Group-Containing Segment (a1), Oligomer a1' as Ionic Group-Free Segment (a2), and Octafluorobiphenylene as Linker Portion To a 500 mL three-neck flask equipped with a stirrer, nitrogen supply tube, and Dean-Stark trap, 0.56 g of potassium carbonate (reagent manufactured by Aldrich, 4 mmol) and 16 g (1 mmol) of the ionic group-containing oligomer a7 (with terminal OM groups) were fed, followed by nitrogen purge, dehydration in 100 mL of N-methylpyrolidone (NMP) and 30 mL of cyclohexane at 100° C., heating to remove cyclohexane, addition of 11 g (1 mmol) of the ionic group-free oligomer a1' (terminal fluoro group), and reaction at 105° C. for 24 hour. The material was purified by reprecipitation in a large amount of isopropyl alcohol to obtain a block copolymer b5. It had a weight average molecular weight of 290,000.

In the block copolymer b5, no constituent units as represented by the general formula (S1) were contained as ionic group-containing segments (A1), and constituent units as represented by the general formula (NP1) were contained at 100 mol % as ionic group-free segments (A2). In the ionic group-containing segments (A1), the constituent units as represented by the general formulae (Q1), (Q2), (Q3), and (Q4) accounted for molar fractions of 50 mol %, 0 mol %, 0 mol %, and 50 mol %, respectively, failing to meet the relation 0≤Y<X<Z<1 (T1).

A 25 wt % N-methylpyrolidone (NMP) solution of the resulting block copolymer b5 was subjected to pressure filtration through a glass fiber filter and flow-cast on a glass substrate, dried at 100° C. for 4 hours, and heat-treated in ity of 25%, though inferior compared to Examples 15 to 20 where the sulfonation density is high. It showed only a small dimensional change rate of 9% and a high hot water resistance. It had a molecular weight retention of 82% and high chemical stability.

In addition, co-continuous phase-separated structures with a domain size of 18 nm were confirmed by TEM observation. It was found that both ionic group-containing domains and ionic group-free domains formed continuous phases.

Comparative Example 4

Synthesis of Ionic Group-Free and Ketal Group-Free Polyether Ketone Oligomer c1

Except for feeding 21.4 g (100 mmol) of 4,4'-dihydroxy benzophenone (DHBP) instead of 25.8 g (100 mmol) of 2,2-bis(4-hydroxyphenyl)-1,3-dioxane (K-DHBP), the same procedure as described in Example 15 was carried out to synthesize an ionic group-free polyether ketone oligomer. Polymerization was difficult because polymer precipitation started in the initial stage of the polymerization. it was difficult to polymerize a block copolymer because of its insolubility in solvents, and it was impossible to evaluate it as electrolyte membrane.

Comparative Example 5

A polyethersulfone based block copolymer was synthesized by a method described in Journal of Polymer Science A Polymer Chemistry, 48, 2757, 2010. Specifically, 4,4-dichlorodiphenyl sulfone was first reacted in fuming sulfuric acid, and after the completion of the reaction, sodium chloride was used to perform salt precipitation to produce 3,3'-sodium disulfonate-4,4'-dichlorodiphenyl sulfone (hereinafter referred to as SDCDPS). Then, in a nitrogen atmosphere, 3.16 g (6.0 mmol) of the SDCDPS, 1.34 g (7.2 mmol) of 4,4'-biphenol, 1.49 g (10.8 mmol) of potassium carbonate, 23 mL of NMP, and 20 mL of toluene were fed in a single neck eggplant shaped flask equipped with a Dean-Stark trap and maintained at 150° C. for 2 hours to remove moisture out of the system by azeotropic distillation. Subsequently, the material was heated to 180° C., and reacted for 16 hours. After leaving it to stand to cool, the reaction solution was poured into water, and potassium chloride was added. The precipitate was recovered by filtration and dried at 60° C. under reduced pressure to produce a hydrophilic oligomer with OM groups at both terminals.

Then, in a nitrogen atmosphere, 4.31 g (15.0 mmol) of 4,4'-dichlorodiphenyl sulfone, 3.05 g (16.4 mmol) of 4,4'-biphenol, 3.39 g (24.5 mmol) of potassium carbonate, 35 mL of NMP, and 20 mL of toluene were fed in a single neck eggplant shaped flask equipped with a Dean-Stark trap and maintained at 150° C. for 2 hours to remove moisture out of the system by azeotropic distillation. Subsequently, the material was heated to 180° C., and reacted for 12 hours. After leaving it to stand to cool, the reaction solution was poured into water and the resulting precipitate was filtered and washed with methanol. Then, it was dried at 100° C. under reduced pressure to produce a hydrophobic oligomer with OM groups at both terminals.

In a nitrogen atmosphere, 0.45 g of the hydrophilic oligomer, 0.20 g of the hydrophobic oligomer, and 5.5 mL of NMP were fed to a single neck eggplant shaped flask equipped with a three way cock and dissolve the hydrophilic oligomer and hydrophobic oligomer at 80° C. After air-cooling it, 0.02 g (0.06 mmol) of decafluorobiphenyl and 0.01 g (0.07 mmol) of potassium carbonate were added and reacted at 120° C. for 18 hours. After leaving it to stand to cool, the reaction solution was diluted with NMP and poured into isopropanol, and the resulting precipitate was filtered and washed with water. Subsequently, the resulting polymer was subjected to acid treatment. The resulting polymer was stirred in a 1.0M sulfuric acid aqueous solution at room temperature for 2 days, and the polymer was recovered by filtration. Then, the polymer was washed adequately with pure water and dried at 60° C. for 10 hours to produce a light brown polymer material. It had a weight average molecular weight of 150,000 and it was difficult to polymerize to a higher molecular weight.

Furthermore, the resulting polymer was reacted in concentrated sulfuric acid at 45° C. for 6 hours to sulfonate the biphenyl units, followed by adequate washing with pure water.

Its ion exchange capacity was determined to be 2.7 meq/g from neutralization titration. The electrolyte membrane was hard and brittle as well as opaque and nonuniform from visual observation. It had a degree of proton conductivity of 200 mS/cm at 80° C. and a relative humidity of 85% and 0.1 mS/cm at 80° C. and a relative humidity of 25%, and had a poor proton conductivity under low humidify conditions compared to Examples 15 to 20. In addition, it had a large dimensional change rate L2/L1 of 150% and inferior in hot water resistance. Its molecular weight retention rate was 10%, and the chemical stability was low because of a smaller number of constituent units as represented by the general formula (S1) or (NP1).

Furthermore, lamellar phase-separated structures with a domain size of 30 nm were found in TEM observation. It was found that both ionic group-containing domains and ionic group-free domains formed continuous phases.

Comparative Example 6

Synthesis of an Ionic Group-Free Oligomer c2' as Represented by the Formula (G24) Given Below

[Chemical formula 55]

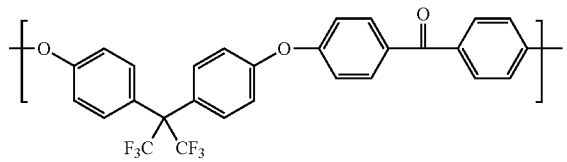

(G24)

Except for feeding 33.6 (100 mmol) of 2,2-bis(4-hydroxyphenyl) hexafluoropropane instead of 25.8 g (100 mmol) of 2,2-bis(4-hydroxyphenyl)-1,3-dioxane (K-DHBP), the same procedure as described in Example 15 was carried out to synthesize an ionic group-free oligomer c2 (with terminal hydroxyl groups). It had a number average molecular weight of 13,000.

In addition, except for feeding the above ionic group-free oligomer c2 (with terminal hydroxyl groups) (2 mmol) instead of the above ionic group-free oligomer a1 (with terminal hydroxyl groups), the same procedure as in described in Example 15 was carried out to synthesize an ionic group-free oligomer c2' (with terminal fluoro groups) as represented by the formula (G24) given above. It had a number average molecular weight of 14,000, and the number average molecular weight of the ionic group-free oligomer c2' was calculated at 13,400 by subtracting a value corresponding to the linker portion (molecular weight 630).

Synthesis of an Ionic Group-Containing Oligomer c3 as Represented by the General Formula (G25) Given Below

[Chemical formula 56]

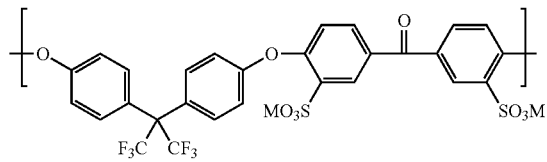

(G25)

(In the formula, M represents Na or K.)

Except for feeding 33.6 (100 mmol) of 2,2-bis(4-hydroxyphenyl) hexafluoropropane instead of 12.9 g (50 mmol) of 2,2-bis(4-hydroxyphenyl)-1,3-dioxane (K-DHBP) and 9.3 g of 4,4'-biphenol (reagent manufactured by Aldrich, 50 mmol), the same procedure as described in Example 15 was carried out to synthesize an ionic group-containing oligomer c3 (with OM groups) as represented by the formula (G25). It had a number average molecular weight of 19,000.

Synthesis of Block Copolymer d1

Except for feeding 19 g (1 mmol) of an ionic group-containing oligomer c3 (with terminal OM groups) instead of an ionic group-containing oligomer a2 (with terminal OM groups) and feeding 14 g (1 mmol) of an ionic group-free oligomer c2' (with terminal fluoro groups) instead of an ionic group-free oligomer a1' (with terminal fluoro groups), the same procedure as described in Example 15 was carried out to produce a block copolymer d1. It had a weight average molecular weight of 160,000.

In the block copolymer d1, no constituent units as represented by the general formula (S1) were contained as ionic group-containing segments (A1), and no constituent units as represented by the general formula (NP1) were contained as ionic group-free segments (A2). Furthermore, it contained no constituent units as represented by the general formula (Q1) or (Q2), which are contained in the ionic group-containing segment (A1).

Using a 25 wt % N-methylpyrolidone (NMP) solution of the resulting block copolymer d1, the procedure described in Example 15 was carried out to produce a polymer electrolyte membrane.

Its ion exchange capacity was determined to be 2.3 meq/g from neutralization titration. Furthermore, it violently swelled when immersed in hot water, and it was so difficult to handle that it sometimes broke when held.

INDUSTRIAL APPLICABILITY

The polymer electrolyte materials and polymer electrolyte membranes according to the present invention can be applied to various electrochemical devices (for example, fuel cells, water electrolytic equipment, and chloroalkali electrolytic equipment). Among others, they serve effectively for fuel cells, particularly for fuel cells operating on hydrogen.

The polymer electrolyte fuel cells according to the present invention can serve for uses including, but not limited to, electric power supply sources for portable appliances such as portable telephones, personal computers, PDA (Personal Digital Assistant), camcorders, and digital cameras; home electric appliances such as cordless cleaners; toys; vehicles such as, power-assisted bicycles, motorcycles, automobiles, buses, and trucks; and movable bodies such as ships and railroad cars; as well as alternatives to conventional primary and secondary batteries such as stationary type power generators and hybrid power sources therewith.

The invention claimed is:

1. A sulfonic acid group-containing polymer produced by polymerization of a compound comprising an aromatic sulfonic acid derivative as represented by formula (M1), wherein a sulfonic acid group is contained in more than 50% of all phenyl groups:

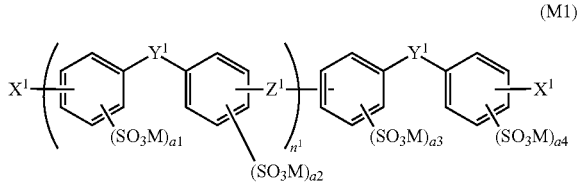

(M1)

wherein, in the formula (M1), $n^1$ is an integer of 1 or greater: $a_1$ to $a_4$ are each an integer of 0 or greater; M's are independently a hydrogen, a metal cation, an ammonium cation, or a hydrocarbon group with a carbon number of 1 to 20; $X^1$'s are independently a halogen atom: $Y^1$ is an electron-withdrawing group; and $Z^1$ is an electron-withdrawing group, —O—, —S—, or direct bonding.

2. The sulfonic acid group-containing polymer as claimed in claim 1, wherein the formula (M1) is as represented by formula (M2):

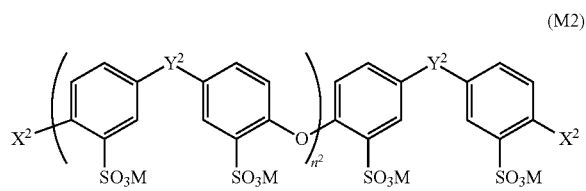

(M2)

wherein, in the formula (M2), $n^2$ is an integer of 1 or greater; M's are independently a hydrogen, a metal cation, an ammonium cation, or a hydrocarbon group with a carbon number of 1 to 20; X's are independently F or Cl; and Y is —CO— or —SO$_2$—.

3. The sulfonic acid group-containing polymer as claimed in claim 2, wherein the formula (M2) is as represented by formula (M3):

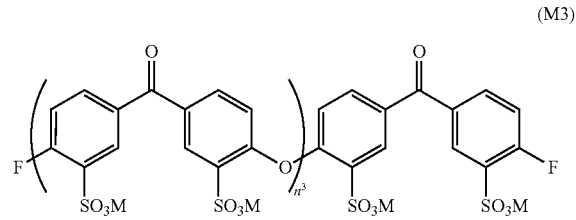

(M3)

wherein, in the formula (M3), $n^3$ is an integer of 1 to 3, and M's are independently a hydrogen, a metal cation, an ammonium cation, or a hydrocarbon group with a carbon number of 1 to 20.

4. The sulfonic acid group-containing polymer of claim of 1, the sulfonic acid group-containing polymer is produced by polymerization of at least a compound comprising an aromatic sulfonic acid derivative as represented by formula (M1) and a divalent phenol compound.

5. A sulfonic acid group-containing polymer comprising constituent units as represented by formula (P1) or formula (P2), wherein a sulfonic acid group is contained in more than 50% of all phenyl groups in the formula (P1) or the formula (P2):

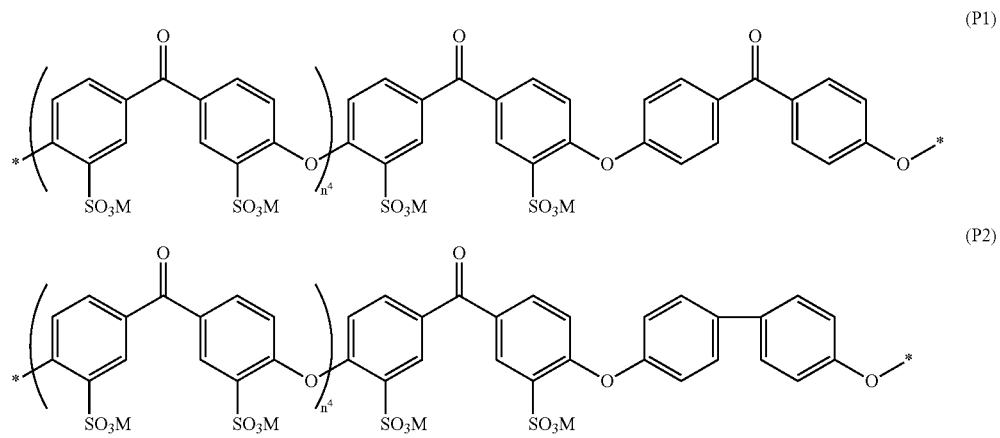

wherein, in the formulae (P1) and (P2), $n^4$ is an integer of 1 to 3; M's are independently a hydrogen, a metal cation, an ammonium cation, or a hydrocarbon group with a carbon number of 1 to 20; and * indicates bonding sites to constituent units as represented by either the formula (P1) or the formula (P2) or to other constituent units.

6. The sulfonic acid group-containing polymer as claimed in claim 5, wherein the sulfonic acid group-containing polymer comprises a block copolymer comprising a segment containing at least a constituent unit as represented by either the formula (P1) or the formula (P2) and a segment substantially not containing a sulfonic acid group.

7. The sulfonic acid group-containing polymer of claim of 5, wherein a content of formula (P1) or formula (P2) is 20 wt % or more.

* * * * *